(12) United States Patent
Vaka et al.

(10) Patent No.: US 11,000,471 B2
(45) Date of Patent: *May 11, 2021

(54) PROGRAMMABLE PHARMACEUTICAL COMPOSITIONS FOR CHRONO DRUG RELEASE

(71) Applicant: KASHIV SPECIALTY PHARMACEUTICALS, LLC, Bridgewater, NJ (US)

(72) Inventors: Siva Ram Kiran Vaka, Piscataway, NJ (US); Paras Jariwala, Somerset, NJ (US); Jaydeep Vaghashiya, Franklin park, NJ (US); Atsawin Thongsukmak, Basking Ridge, NJ (US); Dipen Desai, Whippany, NJ (US); Wantanee Phuapradit, Montville, NJ (US); Navnit H. Shah, Clifton, NJ (US)

(73) Assignee: KASHIV SPECIALTY PHARMACEUTICALS, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/975,493

(22) PCT Filed: Mar. 5, 2019

(86) PCT No.: PCT/US2019/020815
§ 371 (c)(1),
(2) Date: Aug. 25, 2020

(87) PCT Pub. No.: WO2019/173384
PCT Pub. Date: Sep. 12, 2019

(65) Prior Publication Data
US 2021/0030685 A1 Feb. 4, 2021

Related U.S. Application Data

(60) Provisional application No. 62/638,667, filed on Mar. 5, 2018, provisional application No. 62/760,771, filed on Nov. 13, 2018.

(51) Int. Cl.
| | | |
|---|---|---|
| *A61K 9/00* | (2006.01) | |
| *A61K 9/20* | (2006.01) | |
| *A61K 31/138* | (2006.01) | |
| *A61K 31/155* | (2006.01) | |
| *A61K 31/165* | (2006.01) | |
| *A61K 31/4045* | (2006.01) | |
| *A61K 31/4178* | (2006.01) | |
| *A61K 31/4458* | (2006.01) | |

(Continued)

(52) U.S. Cl.
CPC .......... *A61K 9/0004* (2013.01); *A61K 9/2027* (2013.01); *A61K 9/2031* (2013.01); *A61K 9/2054* (2013.01); *A61K 9/2086* (2013.01); *A61K 31/138* (2013.01); *A61K 31/155* (2013.01); *A61K 31/165* (2013.01); *A61K 31/4045* (2013.01); *A61K 31/4178* (2013.01); *A61K 31/4458* (2013.01); *A61K 31/573* (2013.01); *A61K 45/06* (2013.01)

(58) Field of Classification Search
CPC ...... A61K 9/20; A61K 9/2004; A61K 9/2013; A61K 9/2009; A61K 9/286; A61K 9/2866; A61K 9/2886; A61K 9/288; A61K 9/48; A61K 9/4816; A61K 9/50; A61K 9/5005; A61K 9/5042; A61K 9/5073
See application file for complete search history.

(56) References Cited

U.S. PATENT DOCUMENTS

| | | | | |
|---|---|---|---|---|
| 5,156,850 A | * | 10/1992 | Wong | A61K 9/0004 424/473 |
| 10,898,431 B2 | * | 1/2021 | Vaka | A61K 31/138 |
| 2003/0232082 A1 | * | 12/2003 | Li | A61K 9/284 424/473 |

OTHER PUBLICATIONS

Kerthikeyan et al (Development and Evaluation of Osmotically Controlled Glipizide Extended Release Tablet; Thesis Paper, The Tamil Nadu Dr.M.G.R. Medical University, 2017). (Year: 2017).*

* cited by examiner

Primary Examiner — Micah Paul Young
(74) Attorney, Agent, or Firm — Kashiv Specialty Pharmaceuticals, LLC; Vandana Awasthi

(57) ABSTRACT

The present disclosure provides programmable osmotic-controlled oral compositions providing delayed release of a therapeutically acceptable amount of a drug. In certain embodiments, the programmable osmotic-controlled compositions of the disclosure provide a lag time that is independent of the presence or absence of food, type of food, pH, gastric emptying, and volume of gastric fluid. The programmable osmotic-controlled oral compositions of the disclosure comprise a multilayer core comprising a drug for controlled release, wherein the core is coated with a semipermeable membrane comprising an orifice and, optionally, an immediate release coating, comprising a drug for immediate release, over the semipermeable membrane. The multilayered core comprises a pull layer containing the drug and a push layer. The pull layer comprises at least two layers: a placebo layer for providing a desired lag time for the drug release; and an active layer containing the drug and providing a delayed controlled release of the drug. The compositions of the disclosure can be programmed to provide a desired and precise lag time, and release drug, after the lag time, at a rhythm, e.g., that matches the human circadian rhythm of a condition's symptoms and/or of the individual being treated in the application of the therapy to optimize therapeutic outcome and minimize side effects.

19 Claims, 25 Drawing Sheets

Figure 1:
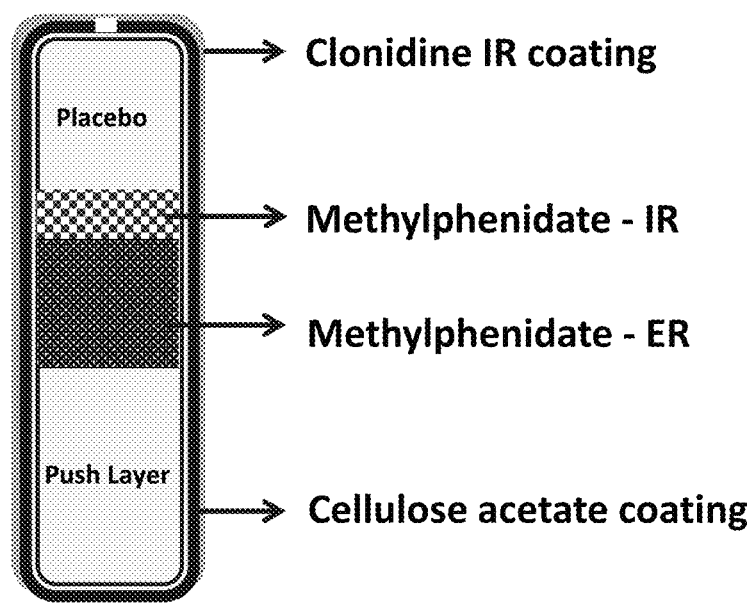

(51) Int. Cl.
*A61K 31/573* (2006.01)
*A61K 45/06* (2006.01)

PROGRAMMABLE PHARMACEUTICAL COMPOSITIONS FOR CHRONO DRUG RELEASE

1. RELATED APPLICATIONS

This application is a U.S. National Stage Patent Application under 35 U.S.C. § 371 of International Application No. PCT/US2019/020815, filed on Mar. 5, 2019, which claims priority to U.S. Provisional Patent Application Nos. 62/638,667, filed Mar. 5, 2018, and 62/760,771, filed Nov. 13, 2018, the disclosures of which are hereby incorporated by reference in their entireties.

2. TECHNICAL FIELD

The presently disclosed subject matter relates to programmable osmotic-controlled oral compositions providing delayed controlled release of a drug. The osmotic-controlled oral compositions of the disclosure can be programmed to provide a desired and precise lag time, thereby releasing drug, after the lag time, at a rhythm, e.g., that matches the human circadian rhythm of a condition's symptoms and/or of the individual being treated in the application of the therapy, to optimize therapeutic outcome and minimize side effects. The programmable osmotic-controlled compositions of the disclosure can provide a lag time that is independent of the presence or absence of food, type of food, pH, gastric emptying, and volume of gastric fluid.

3. BACKGROUND

Attention deficit disorders, e.g., ADHD, are among the most common developmental disorders in children and are characterized by symptoms such as impulsiveness, hyperactivity, and inattentiveness. Hyperactivity is common in children with ADHD. Stimulant medications are widely used as a pharmacological treatment for ADHD/ADD. Stimulant medications approved by the FDA include methylphenidate, and salts and isomers of amphetamine. One major challenge of treating ADHD and other stimulant-responsive conditions is delivering and maintaining an effective stimulant concentration in patients, particularly children, throughout the day, in particular during the morning hours when cognitive abilities and concentration are needed for school, work, or extracurricular activities, and during the late afternoon or evening when students often do homework. Early morning symptom control, including getting the children ready for school, is a major challenge for parents and caregivers of children suffering from ADHD/ADD. Typically, stimulant-based medications are dosed two hours prior to beginning an early morning routine, with an onset of treatment effect usually about two hours after administration. Such medications require twice-daily administration and cause compliance issues. JORNAY PM™, a commercially available product of methylphenidate (Ironshore Pharmaceuticals and Development Inc., NDA #209311), has been approved by the FDA for the treatment of ADHD in patients six years and older. JORNAY PM™ is a methylphenidate formulation that is to be administered in the evening in an attempt to improve ADHD symptoms in the early morning and throughout the day. However, drug release from the formulation can be affected by pH, food, and gastric transit time, with a potential for variable drug release during the night and predawn hours, leading to insomnia.

Extended release of a drug from an oral dosage form can be affected by hydrodynamic conditions in the GI tract that are associated with, e.g., pH and presence of food in the stomach. Osmotic-controlled oral drug delivery systems (OROS) known in the art provide controlled extended release of a drug with zero-order kinetics. The OROS drug delivery system is an advanced drug delivery technology that uses osmotic pressure as a driving force for controlled delivery of active agents. Such systems provide a constant release rate of a drug over an extended period of time. OROS delivery systems utilize osmotic pressure to generate a driving force for imbibing fluid into a compartment enclosed partially or completely by a semipermeable membrane that permits free diffusion of a fluid but not solutes, including active or osmotic agents.

Osmotic-controlled compositions comprising a drug in a mixture with osmotically active agents/osmotic agents are known in the art (e.g., U.S. Pat. Nos. 4,327,725; 4,612,008; 4,783,337; 5,082,668). These compositions comprise a bilayer tablet core surrounded by a semipermeable membrane with an orifice. The first component layer, the pull layer, comprises a drug(s) in a mixture of excipients that forms a deliverable drug formulation within the compartment. A second component layer, the push layer, comprises osmotic agents, e.g., swellable hydrophilic polymers and osmogens. The swellable hydrophilic polymers in the second component layer comprise one or more high molecular weight hydrophilic polymers that swell as fluid is imbibed. The second component layer is referred to as "push layer" because as fluid is imbibed, the hydrophilic polymer swells and pushes against the deliverable drug formulation in the first component layer, thereby facilitating release of drug formulation from the first layer through an orifice in the semipermeable membrane at a substantially constant rate.

Although suitable for providing a controlled release of drugs with various solubilities, osmotic-controlled compositions known in the art are not entirely suitable for being programmed as controlled release compositions that 1) delay the release of a drug/provide a lag time for at least about 4 hours, 2) provide a lag time that is independent of the presence or absence of food, type of food, pH, gastric emptying, and volume of gastric fluid, 3) provide a plasma concentration of the active pharmaceutical ingredient during the lag time that is less than about 10% of a maximum concentration (Cmax), 4) provide pH-independent drug release, after the lag time, at a rhythm that matches the human circadian rhythm of a condition's symptoms and/or of the individual being treated in the application of the therapy, and 5) provide complete drug recovery at a desired time. A typical osmotic-controlled system known in the art provides a short lag time of about 30-120 minutes during which the system hydrates before zero-order delivery from the system is obtained.

Accordingly, there remains a need to develop osmotic-controlled systems that can provide controlled release of a drug at a desired rate and time, while providing complete drug recovery. There remains a need to develop compositions that can be programmed for treating conditions that require delayed controlled release of a drug, e.g., compositions for treating central nervous system (CNS) disorders, asthma, arthritis, congestive heart failure, myocardial infarction, stroke, cancer, peptic ulcer, narcolepsy, epilepsy, migraine, pain, etc., wherein the risk and symptoms of the disease vary predictably over time. In particular, there remains a need to develop compositions that can be programmed to control attention disorders, which require improvement in symptoms in the early morning and throughout the day.

4. SUMMARY

The presently disclosed subject matter provides an osmotic-controlled oral pharmaceutical composition providing delayed release of a therapeutically effective amount of an active pharmaceutical ingredient, the composition comprising a multilayered core comprising the active pharmaceutical agent and an osmogen, and a semipermeable membrane, containing an orifice, over the core. In certain embodiments, when the composition is placed in a dissolution medium comprising about 900 ml of aqueous solution of about 0.01N HCl at a pH of about 2.0, for up to 24 hours, the composition provides a lag time of at least about 6 hours during which the composition releases no more than 10% of the active pharmaceutical ingredient, followed by extended release of the active pharmaceutical agent for about 10-16 hours, as measured in USP Apparatus II at 37° C. and agitation at 50 rpm. In certain embodiments, the composition provides a drug recovery of at least about 90% at about 22 hours from the time of administration into the dissolution medium, and exhibits minimal variability in the lag time with variations in pH, volume of the dissolution medium, and/or the viscosity of the dissolution medium.

In certain embodiments, the multilayered core comprises a placebo layer, an active layer, and a push layer, and the placebo layer is substantially free of osmogen and disintegrant.

In certain embodiments, the placebo layer comprises at least one low molecular weight polyethylene oxide polymer and is substantially free of osmogen and disintegrant.

In certain embodiments, the active layer comprises an active pharmaceutical agent and at least one low molecular weight polyethylene oxide polymer.

In certain embodiments, the push layer comprises at least one high molecular weight polyethylene oxide polymer and an osmogen.

In certain embodiments, the semipermeable membrane comprises a pH-independent water-insoluble polymer and a pH-independent pore former at a polymer to pore former ratio of between about 80:20 and about 99.5:0.5.

In certain embodiments, the semipermeable membrane comprises a pH-independent water-insoluble polymer and a pH-independent pore former at a polymer to pore former ratio of between about 90:10 and 99.5:0.5.

In certain embodiments, the semipermeable membrane is applied with a coating weight gain of about 12.5 wt % of the multilayered core.

In certain embodiments, the pH-independent water-insoluble polymer in the semipermeable membrane comprises polymers selected from the group consisting of cellulose acetate, cellulose acetate butyrate, and cellulose triacetate.

In certain embodiments, the pH-independent water-insoluble polymer is cellulose acetate.

In certain embodiments, the pore former is selected from the group comprising polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

In certain embodiments, the pore former is polyethylene glycol and/or poloxamer.

In certain embodiments, the semipermeable membrane further comprises at least one plasticizer selected from the group consisting of polyethylene glycols, triethyl citrate, triacetin, diethyl tartrate, and combinations thereof.

In certain embodiments, the water-insoluble polymer is cellulose acetate and the pore former is polyethylene glycol or poloxamer.

In certain embodiments, the delayed release comprises a delayed extended release or a delayed chrono release.

In certain embodiments, the active layer comprises an immediate release layer and an extended release layer to provide a delayed chrono release of the active pharmaceutical ingredient.

In certain embodiments, the layers in the multilayered core are arranged in the following order: a placebo layer in fluid communication with the orifice in the semipermeable membrane, the active layer, and the push layer, wherein the push layer is facing away from the orifice.

In certain embodiments, the low molecular weight polyethylene oxide polymer in the placebo layer has an average molecular weight of about 100K, about 200K, about 300K, about 600K, about 900K, or intermediate values thereof.

In certain embodiments, the low molecular weight polyethylene oxide polymer in the placebo layer has an average molecular weight of at least about 600K.

In certain embodiments, the low molecular weight polyethylene oxide polymer in the placebo layer has an average molecular weight of about 900K.

In certain embodiments, the low molecular weight polyethylene oxide polymer in the active layer has an average molecular weight of about 100K, about 200K, about 300K, about 600K, about 900K, or intermediate values thereof.

In certain embodiments, the low molecular weight polyethylene oxide polymer in the active layer has an average molecular weight of about 200K.

In certain embodiments, the placebo layer comprises polyethylene oxide polymer having a molecular weight of about 900K and the active layer comprises polyethylene oxide polymer having a molecular weight of about 200K.

In certain embodiments, the active pharmaceutical ingredient and the polyethylene oxide polymer in the active layer are present in a ratio of between about 20:80 and about 40:60.

In certain embodiments, the active layer further includes an osmogen selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, or combinations thereof.

In certain embodiments, the osmogen in the active layer is sodium chloride.

In certain embodiments, the active layer comprises the osmogen in an amount of between about 2 wt % and about 20 wt % of the active layer.

In certain embodiments, any of the placebo layer, the active layer, and the push layer further comprise a binder, a stabilizer, and/or a lubricant.

In certain embodiments, the high molecular weight polyethylene oxide polymer in the push layer has a molecular weight of at least about 1M, about 2M, about 4M, about 5M, about 7M, or intermediate values thereof.

In certain embodiments, the high molecular weight polyethylene oxide polymer in the push layer has a molecular weight of at least about 4M.

In certain embodiments, the osmogen in the push layer is selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, or combinations thereof.

In certain embodiments, the osmogen is sodium chloride.

In certain embodiments, the osmogen in the push layer is present in an amount of between about 5 wt % and about 30 wt % of the push layer.

In certain embodiments, the stabilizer is succinic acid, butylated hydroxytoluene, or a combination thereof.

The presently disclosed subject matter also provides an oral osmotic-controlled composition providing an immediate release of a therapeutically acceptable amount of a sedative and a delayed release of a therapeutically acceptable amount of a stimulant, the composition comprising a multilayered core comprising the stimulant and an osmogen, a semipermeable membrane containing an orifice, over the core, and an immediate release layer, comprising the sedative, over the semipermeable membrane. In certain embodiments, when the composition is placed in a dissolution medium comprising 900 ml of aqueous solution of 0.01N HCl, at a pH of about 2.0, for up to 24 hours, the composition provides an immediate release of the sedative, followed by a lag time of at least about 6 hours during which the composition releases no more than 10% of the stimulant, followed by extended release of the stimulant for about 10-16 hours, as measured in USP Apparatus II, at 37° C. and agitation at 50 rpm. In certain embodiments, the composition provides a drug recovery of at least about 90% at about 22 hours from the time of administration into the dissolution medium, and exhibits minimal variability in the lag time with variations in pH, volume of the dissolution medium, and/or the viscosity of the dissolution medium.

In certain embodiments, the sedative is selected from the group consisting of clonidine, guanfacine, diphenhydramine, and melatonin.

In certain embodiments, the stimulant is methylphenidate hydrochloride or mixed amphetamines.

In certain embodiments, the multilayered core comprises a placebo layer, an active layer, and a push layer, and the placebo layer is substantially free of osmogen and disintegrant.

In certain embodiments, the placebo layer comprises at least one low molecular weight polyethylene oxide polymer and is substantially free of osmogen and disintegrant.

In certain embodiments, the active layer comprises a stimulant and at least one low molecular weight polyethylene oxide polymer.

In certain embodiments, the push layer comprises at least one high molecular weight polyethylene oxide polymer and an osmogen.

In certain embodiments, the semipermeable membrane comprises a pH-independent water-insoluble polymer and a pH-independent pore former in a polymer to pore former ratio of between about 80:20 and about 99.5:0.5.

In certain embodiments, the semipermeable membrane comprises a pH-independent water-insoluble polymer and a pH-independent pore former in a polymer to pore former ratio of between about 90:10 and about 99.5:0.5.

In certain embodiments, the semipermeable membrane is applied with a coating weight gain of about 12.5 wt % of the multilayered core.

In certain embodiments, the pH-independent water-insoluble polymer in the semipermeable membrane comprises polymers selected from the group consisting of cellulose acetate, cellulose acetate butyrate, cellulose triacetate, and combinations thereof.

In certain embodiments, the pH-independent water-insoluble polymer is cellulose acetate.

In certain embodiments, the pore former is selected from the group consisting of polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

In certain embodiments, the pore former is polyethylene glycol or poloxamer.

In certain embodiments, the semipermeable membrane further comprises at least one plasticizer selected from the group consisting of polyethylene glycols, triethyl citrate, triacetin, diethyl tartrate, and combinations thereof.

In certain embodiments, the water-insoluble polymer is cellulose acetate and the pore former is polyethylene glycol.

In certain embodiments, the cellulose acetate and polyethylene glycol are present in a ratio of about 95:5 or about 98:2.

In certain embodiments, the water-insoluble polymer is cellulose acetate and the pore former is poloxamer.

In certain embodiments, the cellulose acetate and poloxamer are present in a ratio of between about 80:20 and about 99.5:0.5.

In certain embodiments, the delayed release comprises a delayed extended release or a delayed chrono release.

In certain nonlimiting embodiments the active layer comprises an immediate release layer and an extended release layer to provide a delayed chrono release of the stimulant.

In certain embodiments, the layers in the multilayered core are arranged in the following order: a placebo layer in fluid communication with the orifice in the semipermeable membrane, the active layer, and the push layer, wherein the push layer is facing away from the orifice.

In certain embodiments, the low molecular weight polyethylene oxide polymer in the placebo layer has an average molecular weight of about 100K, about 200K, about 300K, about 600K, about 900K, or intermediate values thereof.

In certain embodiments, the low molecular weight polyethylene oxide polymer in the placebo layer has an average molecular weight of at least about 600K.

In certain embodiments, the low molecular weight polyethylene oxide polymer in the placebo layer has an average molecular weight of about 900K.

In certain embodiments, the low molecular weight polyethylene oxide polymer in the active layer has an average molecular weight of about 100K, about 200K, about 300K, about 600K, about 900K, or intermediate values thereof.

In certain embodiments, the low molecular weight polyethylene oxide polymer in the active layer has an average molecular weight of about 200K.

In certain embodiments, the placebo layer comprises polyethylene oxide polymer having a molecular weight of about 900K and the active layer comprises polyethylene oxide polymer having a molecular weight of about 200K.

In certain embodiments, the stimulant and the low molecular weight polyethylene oxide polymer in the active layer are present in a ratio of between about 20:80 and about 40:60.

In certain embodiments, the active layer further includes an osmogen selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, or combinations thereof.

In certain embodiments, the osmogen in the active layer is sodium chloride.

In certain embodiments, the active layer comprises the osmogen in an amount of between about 2 wt % and about 20 wt % of the active layer.

In certain embodiments, any of the placebo layer, the active layer, and the push layer further comprises a binder, a stabilizer, and/or a lubricant.

In certain embodiments, the high molecular weight polyethylene oxide polymer in the push layer has an average molecular weight of at least about 1M, about 2M, about 4M, about 5M, about 7M, or any intermediate values thereof.

In certain embodiments, the high molecular weight polyethylene oxide polymer in the push layer has an average molecular weight of at least about 4M.

In certain embodiments, the osmogen in the push layer is selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, or combinations thereof.

In certain embodiments, the osmogen is sodium chloride.

In certain embodiments, the osmogen in the push layer is present in an amount of between about 5 wt % and about 30 wt % of the push layer.

In certain embodiments, the stabilizer is succinic acid, butylated hydroxytoluene, or a combination thereof.

The presently disclosed subject matter also provides an osmotic-controlled oral pharmaceutical composition providing delayed release of a therapeutically effective amount of an active pharmaceutical ingredient, the composition comprising a multilayered core comprising the active pharmaceutical agent and an osmogen, and a semipermeable membrane, containing an orifice, over the core. In certain embodiments, the multilayered core comprises a placebo layer, an active layer, and a push layer, the placebo layer is substantially free of osmogen and disintegrant, and the composition exhibits minimal variability in lag time when tested for dissolution in 900 ml of 0.01 N HCl, using USP Type II apparatus with a paddle speed of 50 rpm, or when tested for dissolution in 250 ml of 0.01 N HCl, using USP Type III apparatus with a speed of 25 dpm.

The presently disclosed subject matter additionally provides a method for treating ADHD in a subject, the method comprising orally administering to the subject an osmotic-controlled pharmaceutical composition providing a delayed extended release dose of a therapeutically acceptable amount of methylphenidate hydrochloride. In certain embodiments, the composition is administered to the subject, with or without food, before bedtime, and the delayed release dose of methylphenidate keeps the subject active and focused throughout the day, the composition comprises a multilayered core comprising the active pharmaceutical agent and an osmogen, and a semipermeable membrane, containing an orifice, over the core, the multilayered core comprises a placebo layer, an active layer, and a push layer, and the placebo layer is substantially free of osmogen and disintegrant.

Furthermore, the presently disclosed subject matter provides a method for improving patient compliance and convenience during treatment of ADHD, the method comprising orally administering to a patient a composition comprising a therapeutically acceptable amount of a stimulant before bedtime to provide a delayed release dose of the stimulant that keeps the subject alert and focused during the day. In certain embodiments, the composition delays the release of the stimulant to provide a lag time of at least about 6 hours, and during the lag time the plasma concentration of the stimulant is less than about 10% of the maximum concentration (Cmax). In certain embodiments the composition comprises a multilayered core comprising the stimulant and an osmogen, and a semipermeable membrane, containing an orifice, over the core, the multilayered core comprises a placebo layer, an active layer, and a push layer, and the placebo layer is substantially free of osmogen and disintegrant.

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

5. BRIEF DESCRIPTION OF THE DRAWINGS

FIG. 1 depicts a cross-section view of a four-layer osmotic dosage form comprising an IR clonidine coating, a cellulose acetate coating, containing an orifice, below the clonidine IR coating, a placebo layer in fluid communication with the orifice, a delayed immediate release layer containing methylphenidate and placed below the placebo layer, a delayed extended release layer containing methylphenidate and placed below the delayed immediate release layer, and a push layer placed below the delayed extended release layer, the push layer being furthest from the orifice (i.e., facing away from the orifice).

Figure 2:
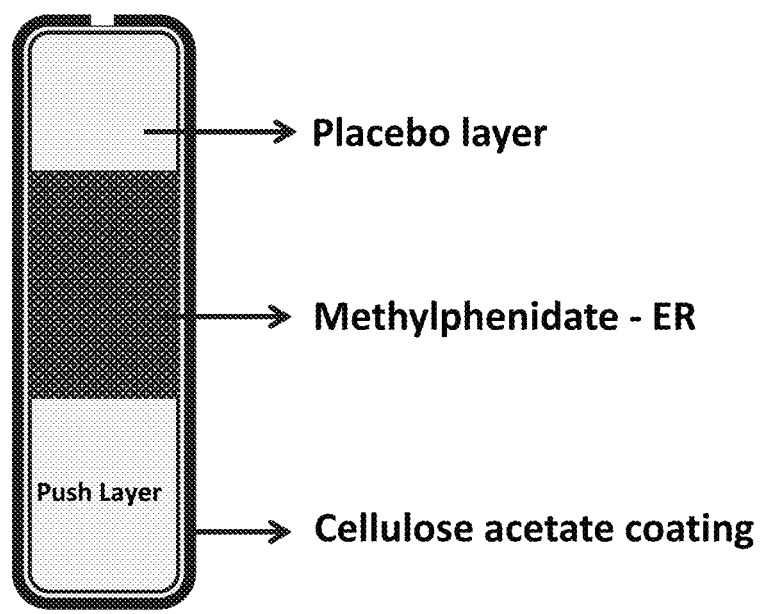

FIG. 2 depicts a cross-section view of a three-layer osmotic dosage form comprising a cellulose acetate coating containing an orifice, a placebo layer in fluid communication with the orifice, a delayed extended release layer containing methylphenidate and placed below the placebo layer, and a push layer placed below the delayed extended release layer and facing away from the orifice.

Figure 3:
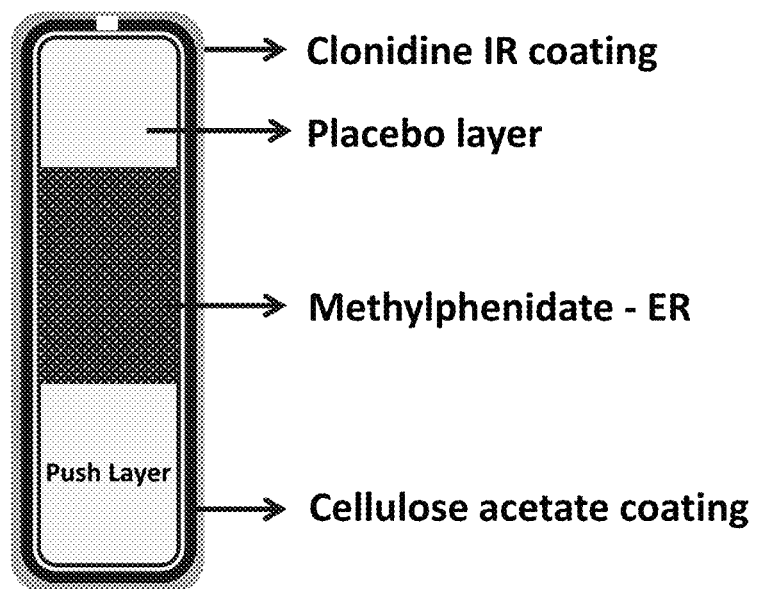

FIG. 3 depicts a cross-section view of a three-layer osmotic dosage form comprising an IR clonidine coating, a cellulose acetate coating containing an orifice below the clonidine IR coating, a placebo layer in fluid communication with the orifice, a delayed extended release layer containing methylphenidate and placed below the placebo layer, and a push layer placed below the delayed extended release layer and facing away from the orifice.

Figure 4:
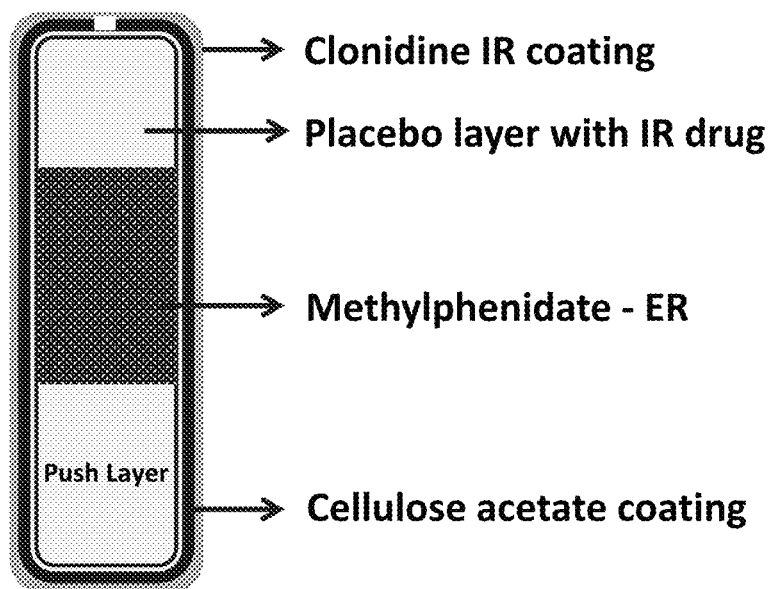

FIG. 4 depicts a cross-section view of a three-layer osmotic dosage form comprising an IR clonidine coating, a cellulose acetate coating containing an orifice below the clonidine IR coating, a "placebo" layer containing small amounts of a drug for IR and in fluid communication with the orifice, a delayed extended release layer containing methylphenidate and placed below the placebo layer, and a push layer placed below the delayed extended release layer and facing away from the orifice.

Figure 5:
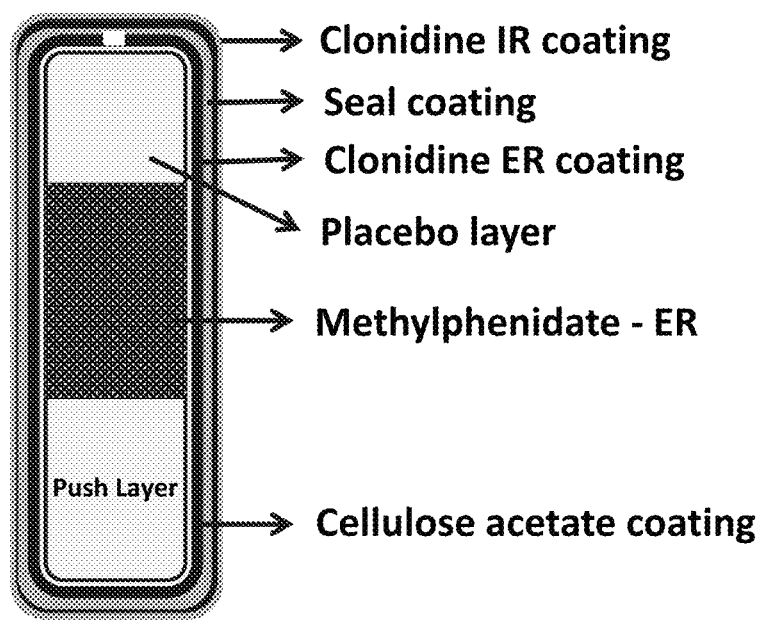

FIG. 5 depicts a cross-section view of a three-layer osmotic dosage form comprising an IR clonidine coating, a seal coating below the IR clonidine coat, a clonidine ER coating below the seal coating, a cellulose acetate coating containing an orifice below the ER clonidine coating, a "placebo" layer in fluid communication with the orifice, a delayed extended release layer containing methylphenidate and placed below the placebo layer, and a push layer placed below the delayed extended release layer and facing away from the orifice.

Figure 6:
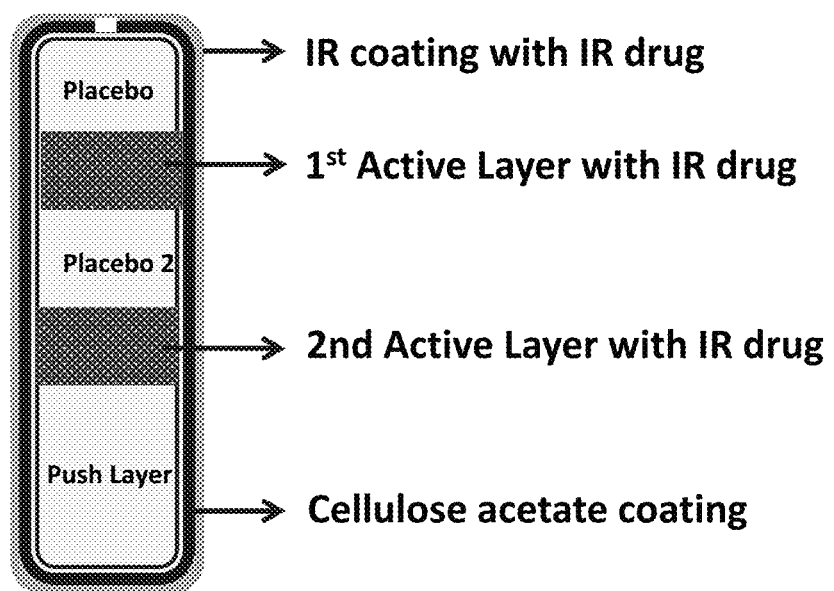

FIG. 6 depicts a cross-section view of a five-layer osmotic dosage form comprising an IR coating containing a drug for IR, a cellulose acetate coating containing an orifice below the IR coating, a first placebo layer in fluid communication with the orifice, a first IR drug layer below the first placebo layer, a second placebo layer below the first IR drug layer, a second IR drug layer below the second placebo layer, and a push layer placed below the second IR drug layer and facing away from the orifice.

Figure 7:
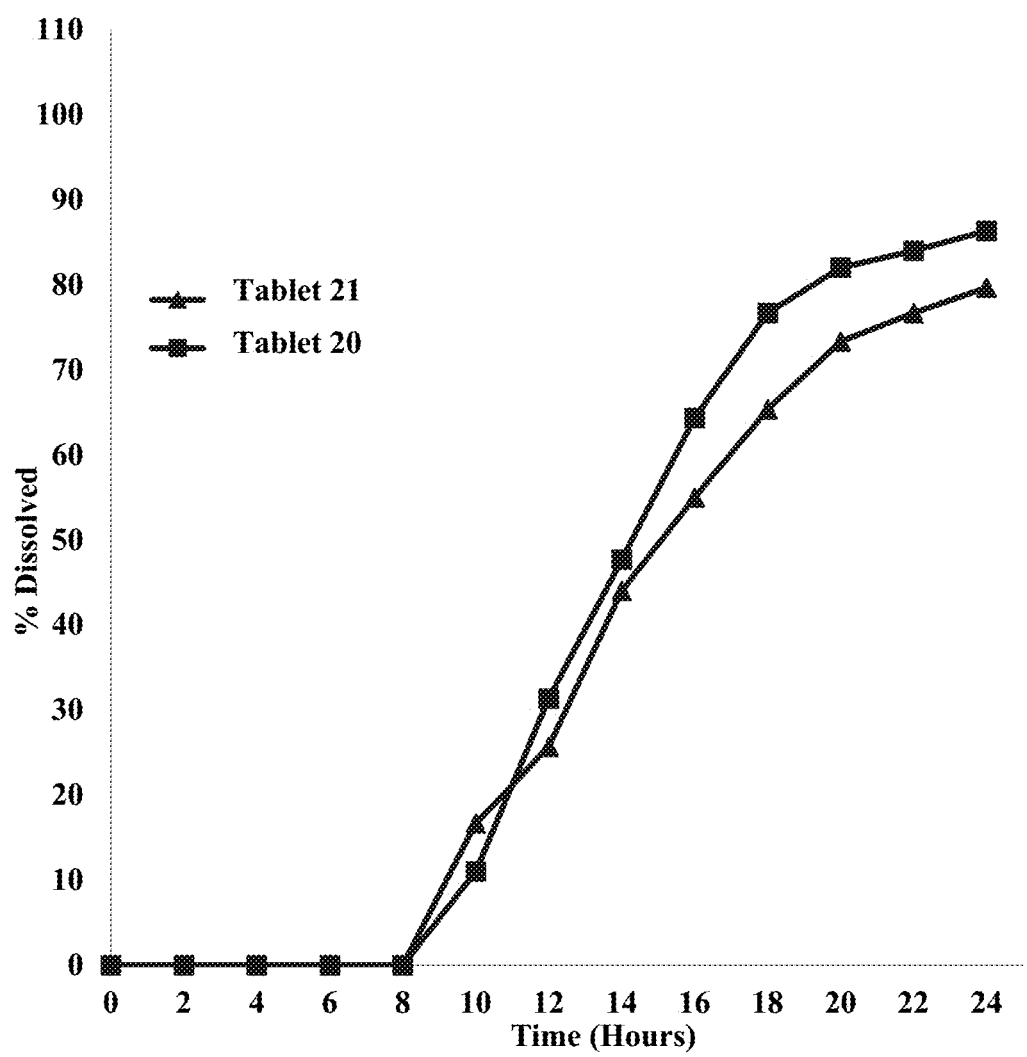

FIG. 7 shows the effect of the amount of POLYOX® in the placebo layer on the dissolution rate of the tablet in about 900 ml of about 0.01N HCl. Tablet 20 contained about 150 mg/dose of POLYOX® WSR 1105, Tablet 21 contained about 75 mg/dose of POLYOX® WSR 1105 in the placebo layer. Percent dissolved is plotted over time (hours).

Figure 8:
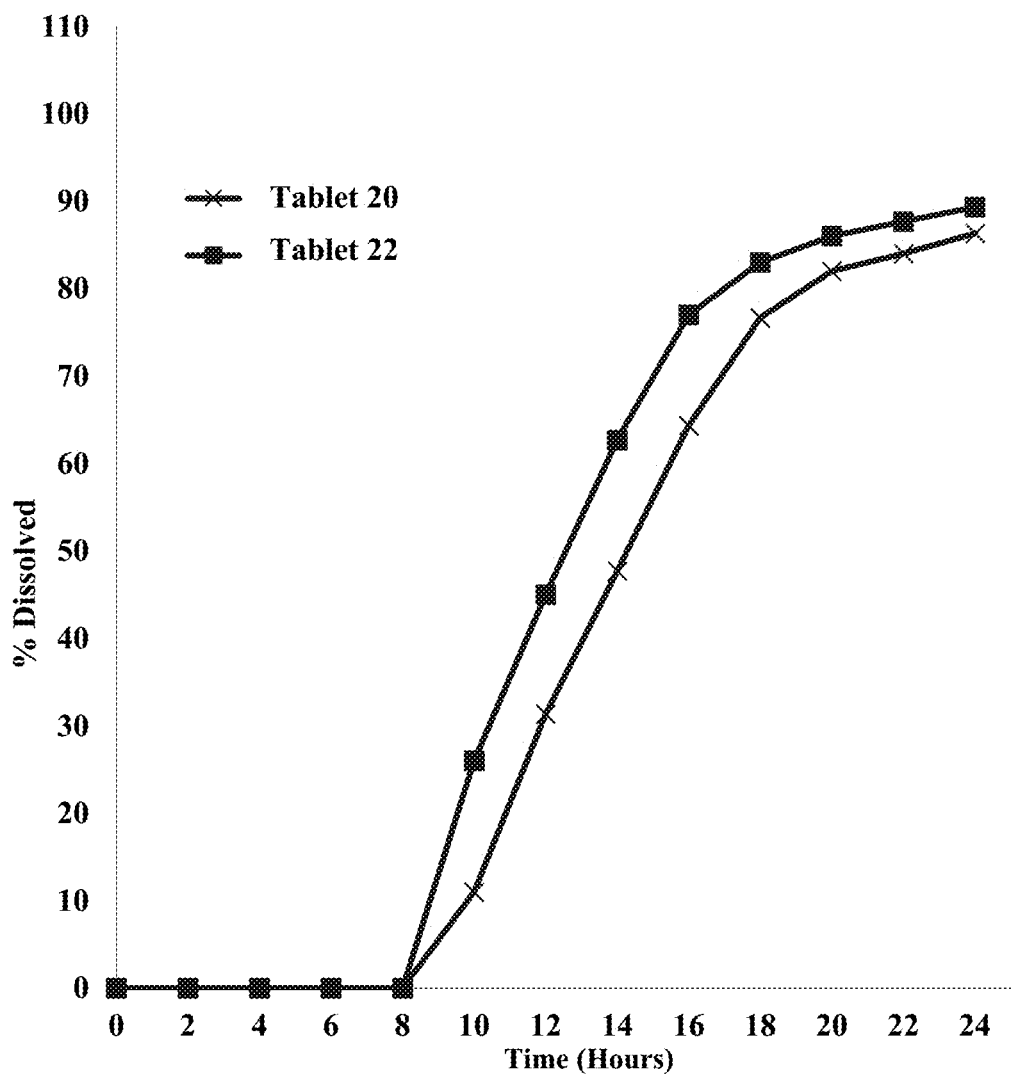

FIG. 8 compares dissolution profiles in about 900 ml of about 0.01N HCl of tablets containing POLYOX® 1105 and POLYOX® 205 in the placebo layer. Tablet 20 contained POLYOX® WSR 1105, Tablet 22 contained POLYOX® 205 in the placebo layer. Percent dissolved is plotted over time (hours).

Figure 9:
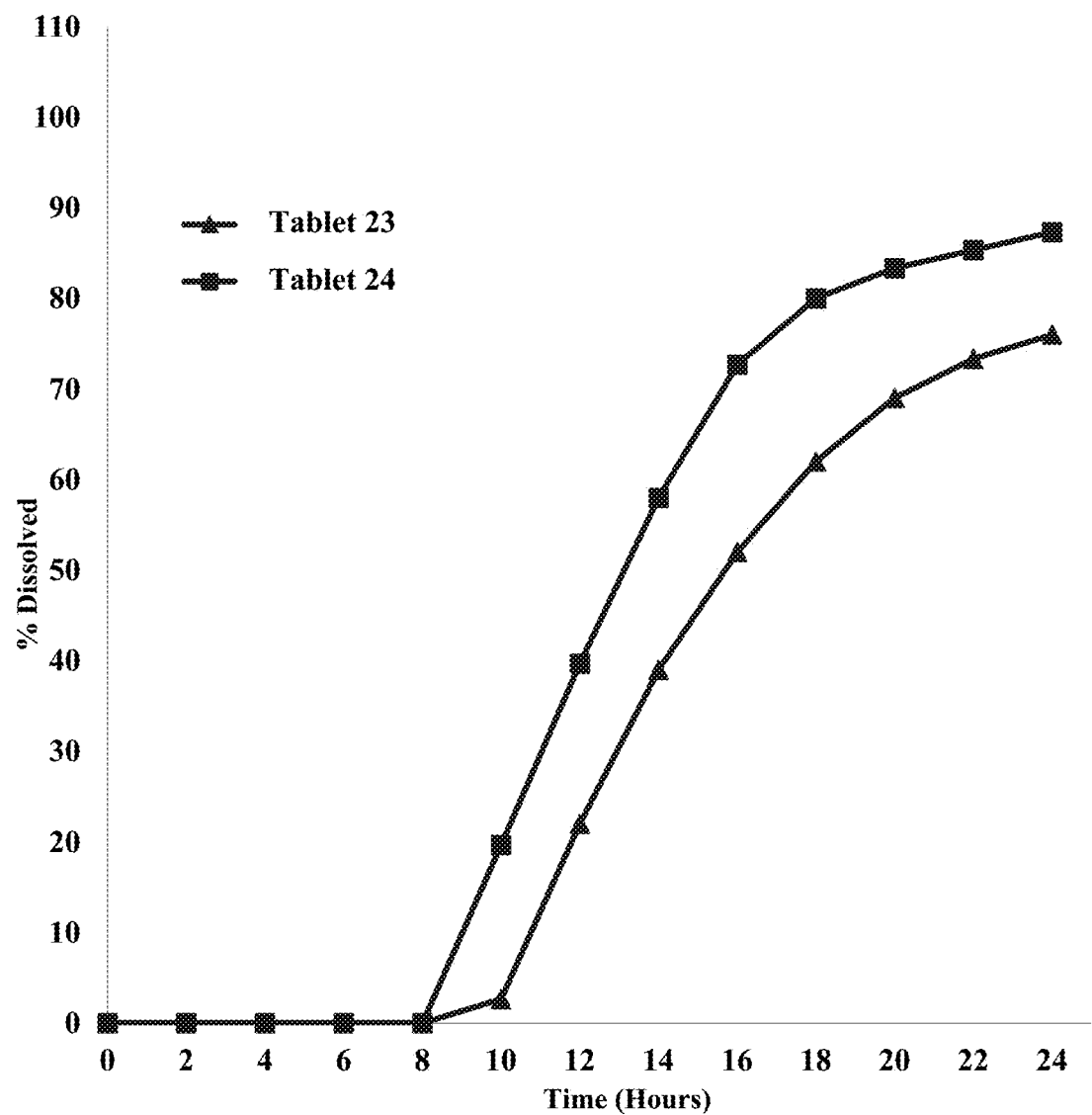

FIG. 9 compares dissolution profiles in about 900 ml of about 0.01N HCl of tablets containing active layers with drug to polymer ratio of about 20:80 (Tablet 23) and drug to polymer ratio of about 28:72 (Tablet 24). Percent dissolved is plotted over time (hours). The Figure demonstrates that lag time is reduced with increasing drug to polymer ratio.

Figure 10:
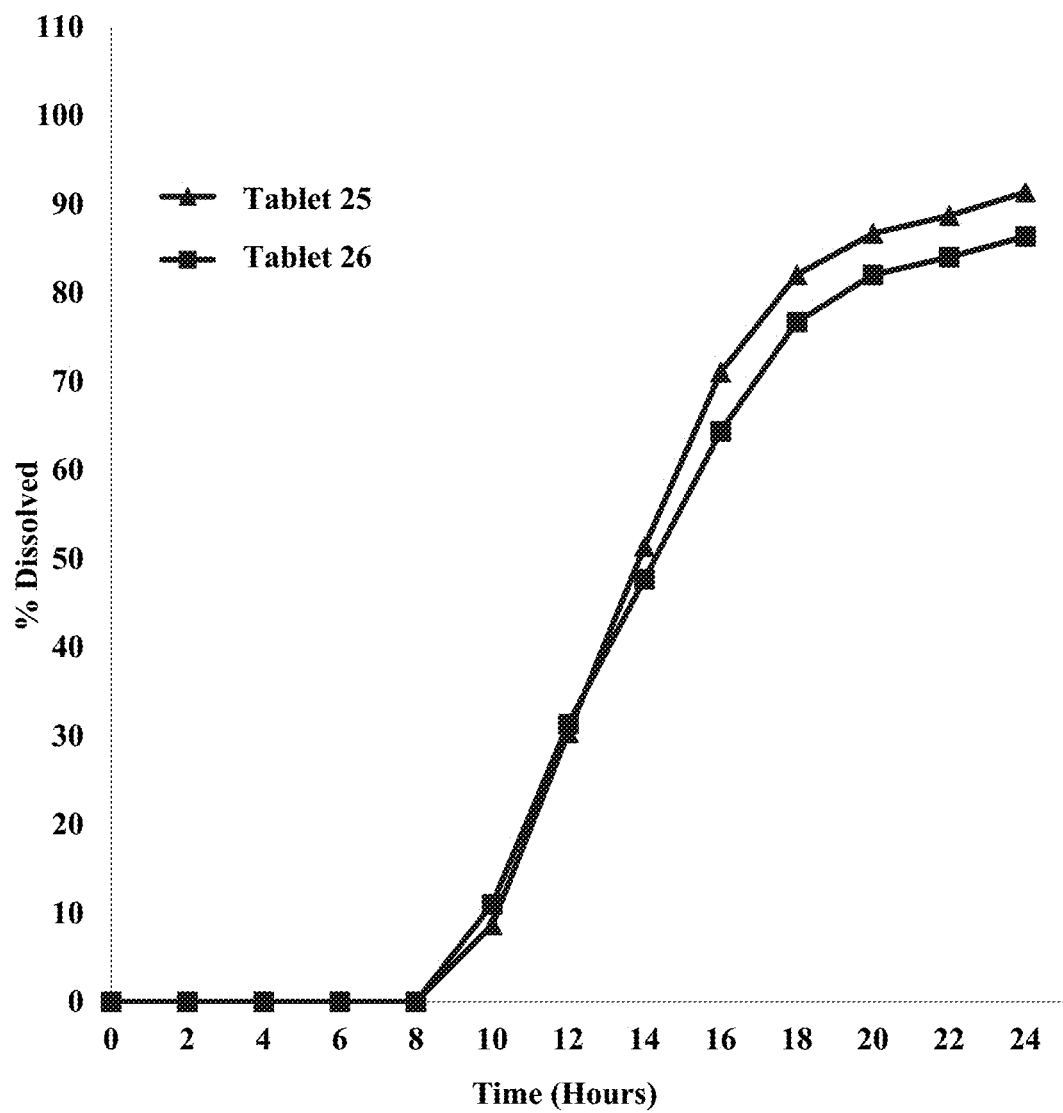

FIG. 10 compares dissolution profile in about 900 ml of about 0.01N HCl of tablets containing sodium chloride in the active layer (Tablet 25) and tablets containing no sodium chloride in the active layer (Table 26). Percent dissolved is plotted over time (hours). The Figure demonstrates that presence of sodium chloride in the active layer improves drug recovery by about 5%, compared to tablets without sodium chloride in the active layer.

Figure 11:
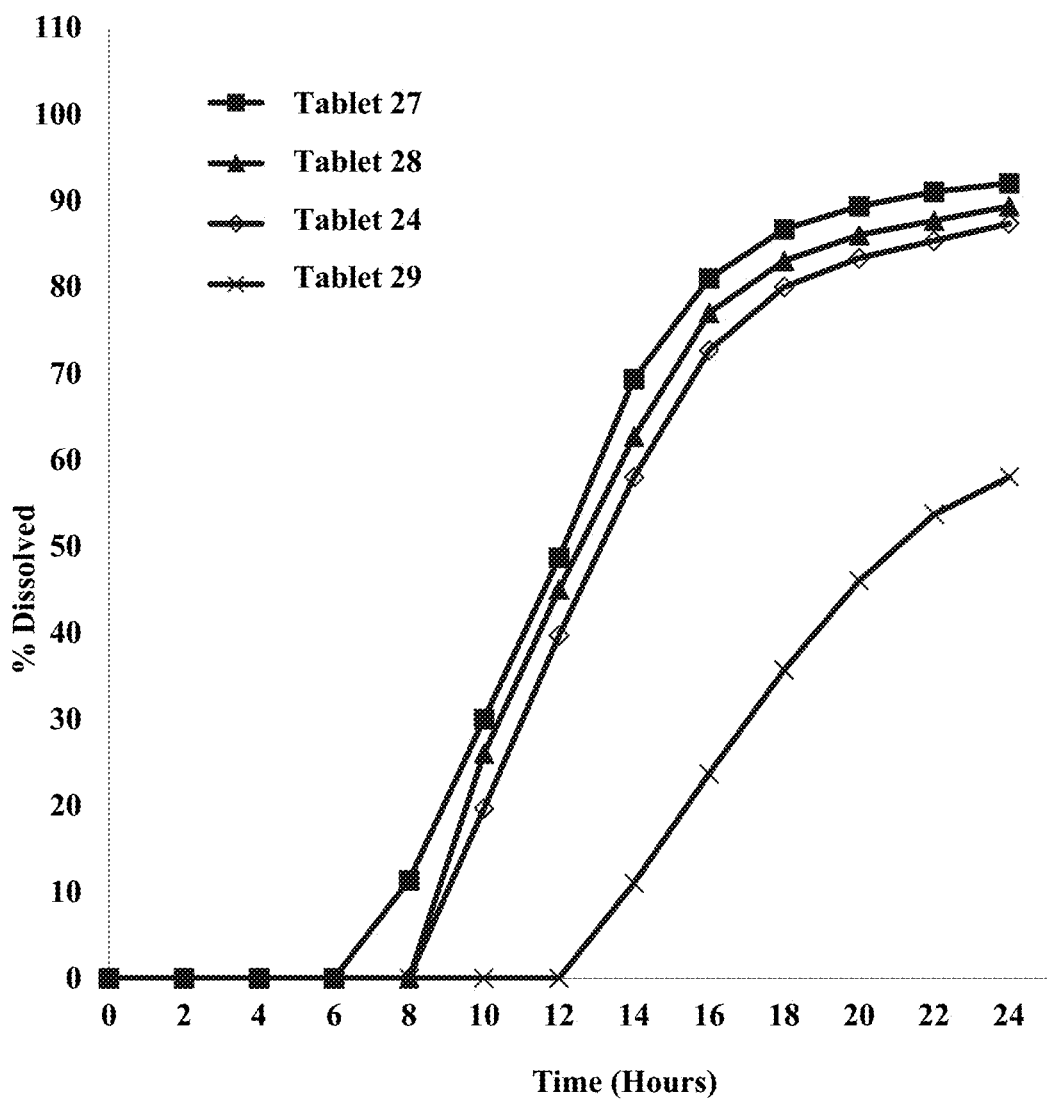

FIG. 11 shows the effect of sodium chloride in the push layer on lag time and drug recovery. The Figure compares dissolution profiles in about 900 ml of about 0.01N HCl of tablets containing about 0 wt % (Tablet 29), about 10 wt % (Tablet 24), about 18 wt %, (Tablet 28) and about 25 wt % (Tablet 27) of sodium chloride in push layer. Percent dissolved is plotted over time (hours). The Figure demonstrates that presence of sodium chloride in push layer improves release rate and drug recovery, when compared with compositions without any sodium chloride in push layer.

Figure 12:
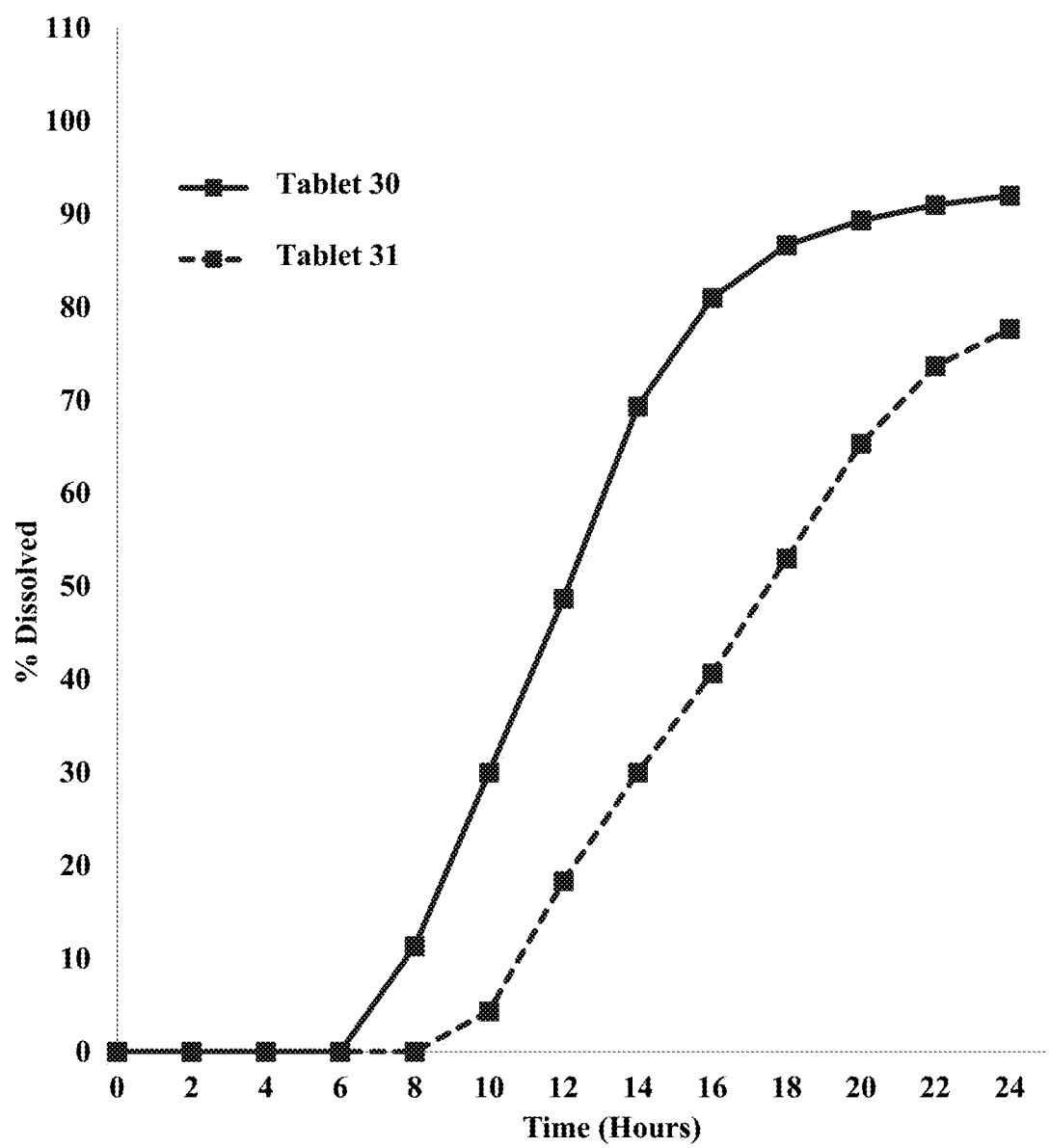

FIG. 12 shows the effect of the cellulose acetate to polyethylene glycol ratio in the semipermeable membrane on lag time and drug recovery of the tablets with a 15% coating weight gain. The Figure compares dissolution profiles in about 900 ml of about 0.01N HCl of tablets containing OPADRY® CA with CA:PEG ratio of about 95:5 (Tablet 30) and OPADRY® CA with CA:PEG ratio of about 98:2 (Tablet 31). Percent dissolved is plotted over time (hours). The Figure demonstrates that the lag time increases with increasing amount of cellulose acetate in the membrane.

Figure 13:
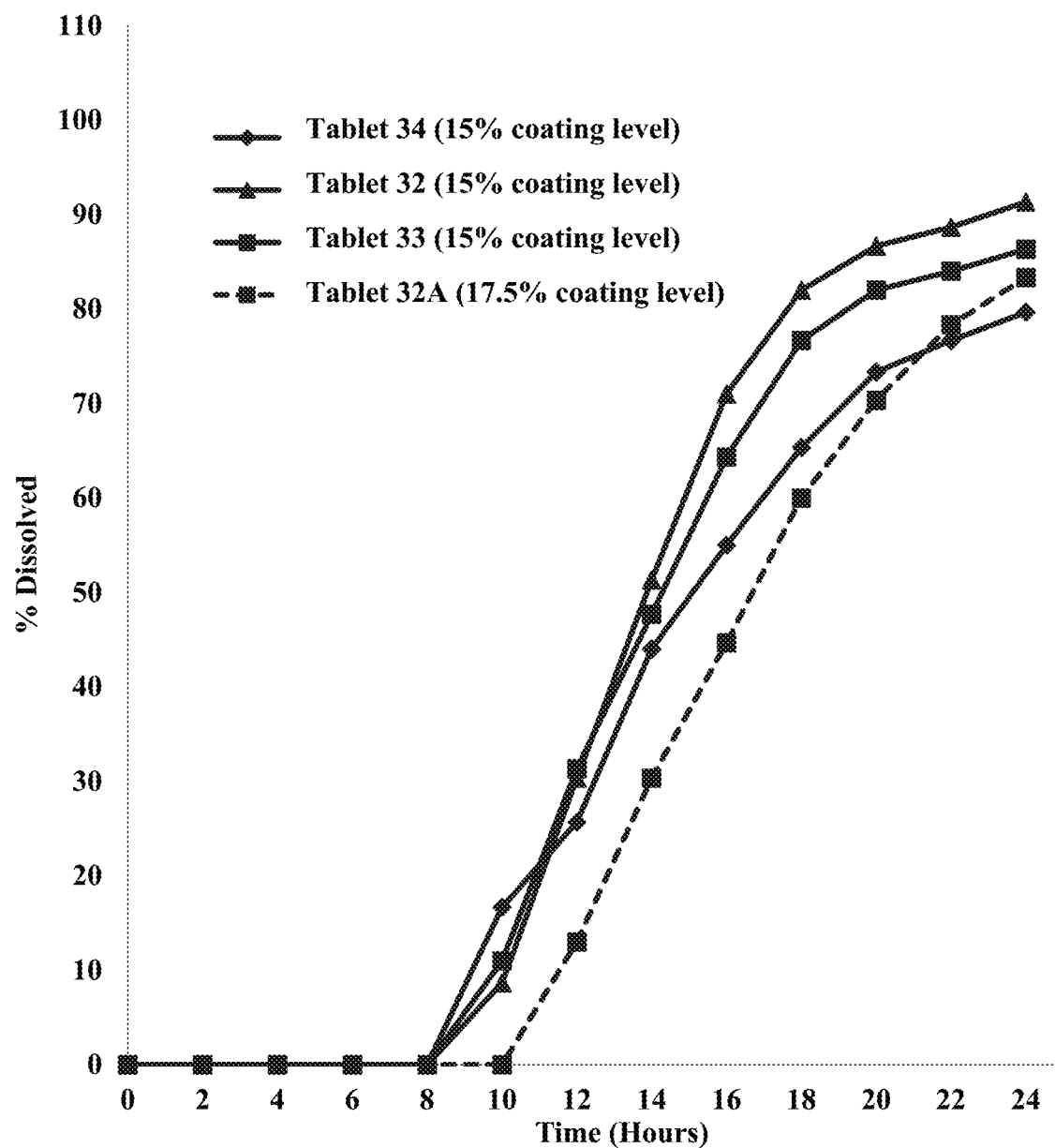

FIG. 13 shows the effect of the presence of sodium chloride in the active layer and the effect of the coating weight gain/coating level of the semipermeable membrane on lag time and drug recovery. The Figure compares dissolution profiles in about 900 ml of about 0.01N HCl of Tablets 32, 33, and 34. Percent dissolved is plotted over time (hours). The Figure demonstrates that lag time increases with increasing coating level of the semipermeable membrane. The Figure further demonstrates that presence of sodium chloride in active layer improves drug recovery.

Figure 14:
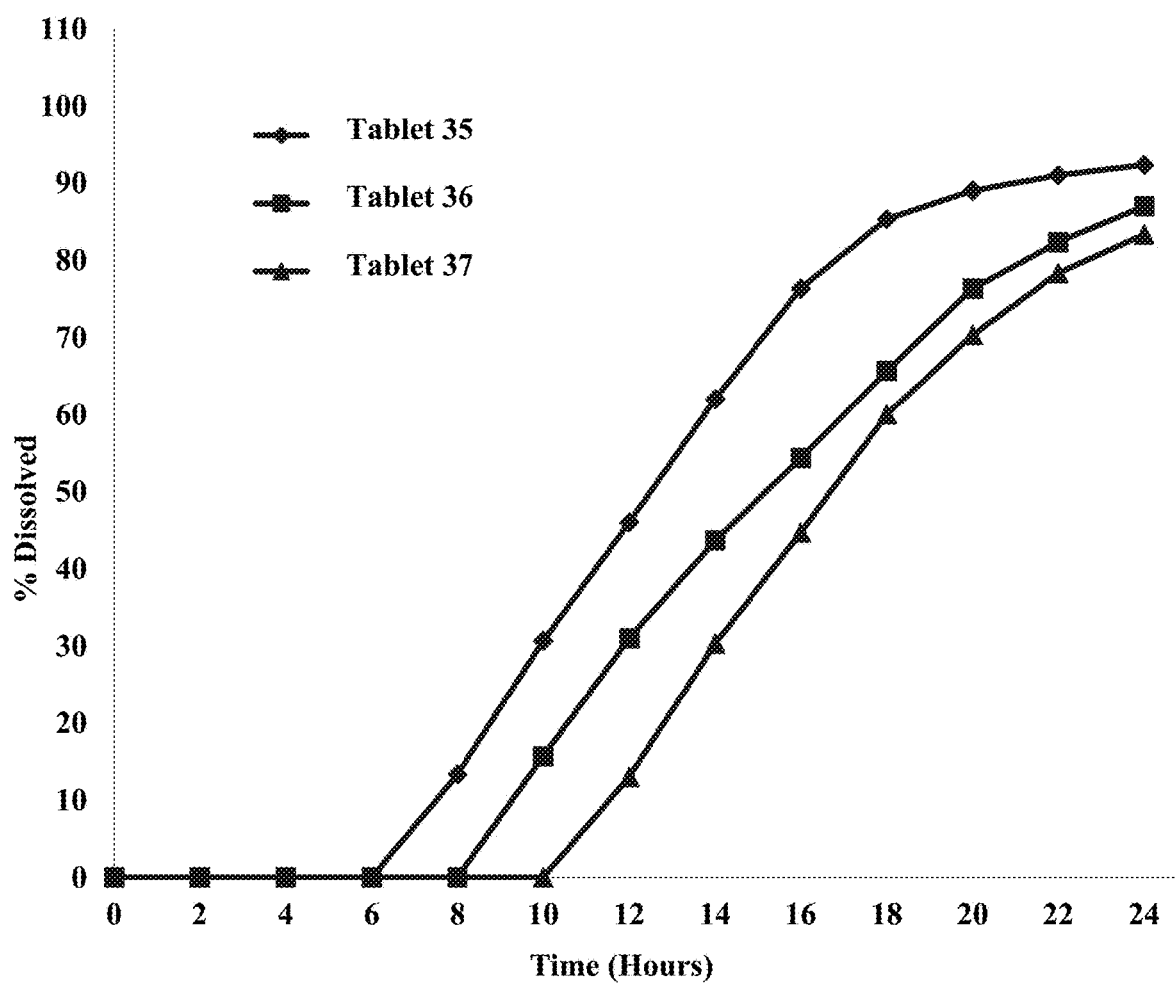

FIG. 14 compares the drug recovery between tablets containing different amounts of sodium chloride in the active layer and/or different grades of POLYOX® in the placebo layer. The Figure compares dissolution profiles in about 900 ml of about 0.01N HCl of tablets containing about 20 mg/dose of sodium chloride in the active layer and POLYOX® 205 in the placebo layer (Tablet 35), about 10 mg/dose of sodium chloride in the active layer and POLYOX® 205 in the placebo layer (Tablet 36), and about 10 mg/dose of sodium chloride in the active layer and POLYOX® 1105 in the placebo layer (Tablet 37). Percent dissolved is plotted over time (hours). The Figure demonstrates that drug recovery increases with increasing the amount of sodium chloride in active layer and reducing the molecular weight of POLYOX® in placebo layer.

Figure 15:
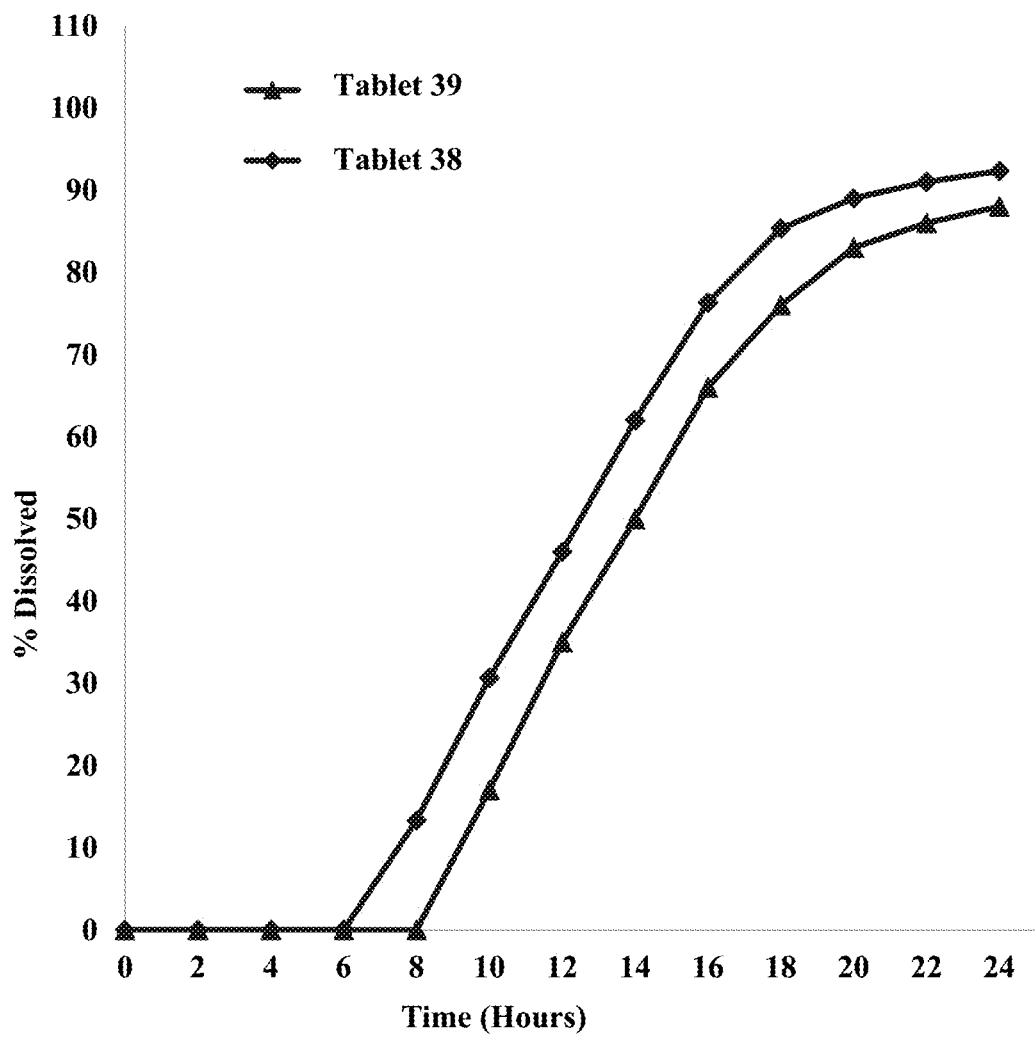

FIG. 15 shows the effect of the amount of POLYOXR in the push layer on lag time. The Figure compares dissolution profiles in about 900 ml of about 0.01N HCl of tablets containing various amounts of POLYOX® (Tablet 38, and Tablet 39). Percent dissolved is plotted over time (hours). The Figure demonstrates that lag time decreases with increasing the amount of POLYOX® in push layer.

Figure 16:
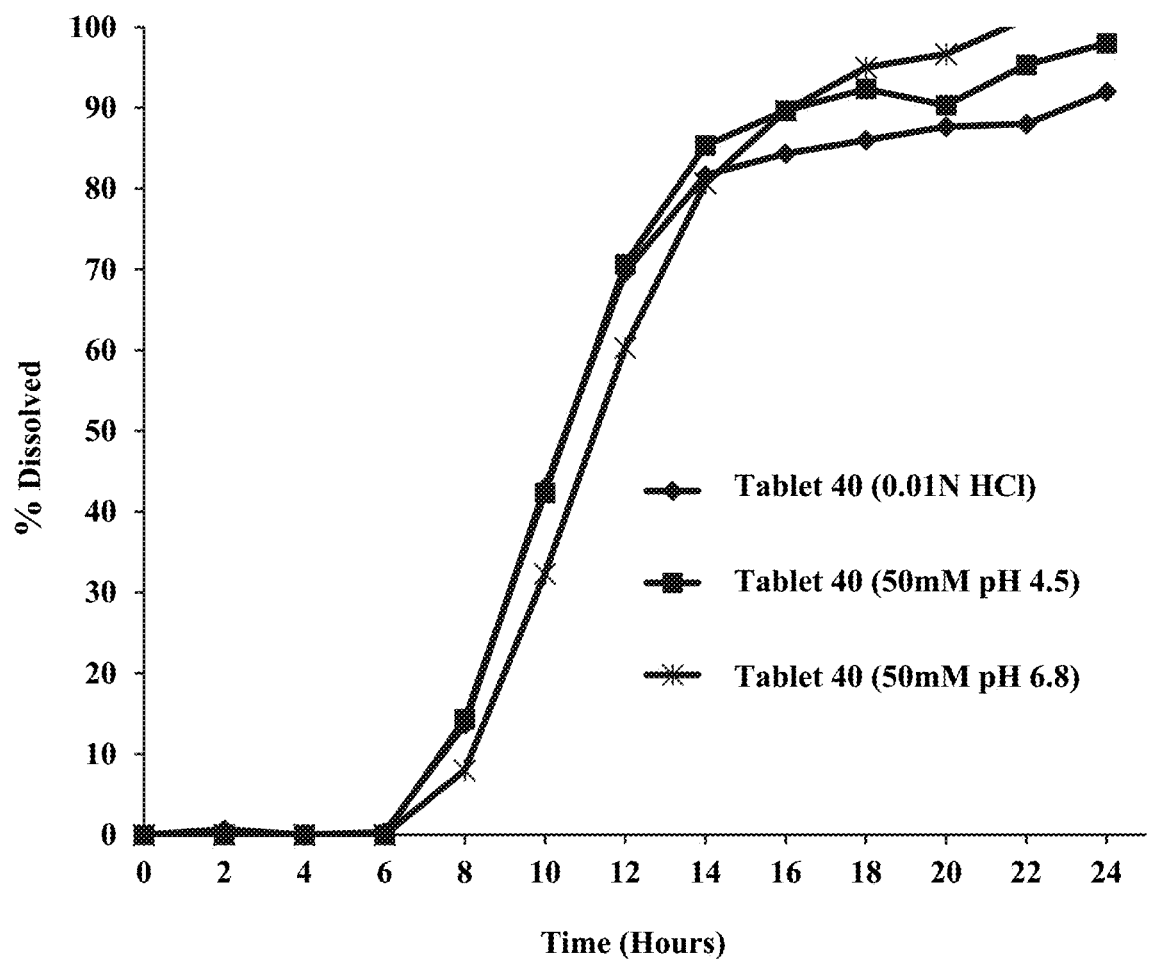

FIG. 16 compares the lag time and dissolution profiles of a composition of the disclosure (Tablet 40) in about 900 ml of about 0.01N HCl, pH 4.5 acetate buffer, and pH 6.8 phosphate buffer. Percent dissolved is plotted over time (hours). The Figure demonstrates that lag time is independent of the pH of the dissolution medium.

Figure 17:
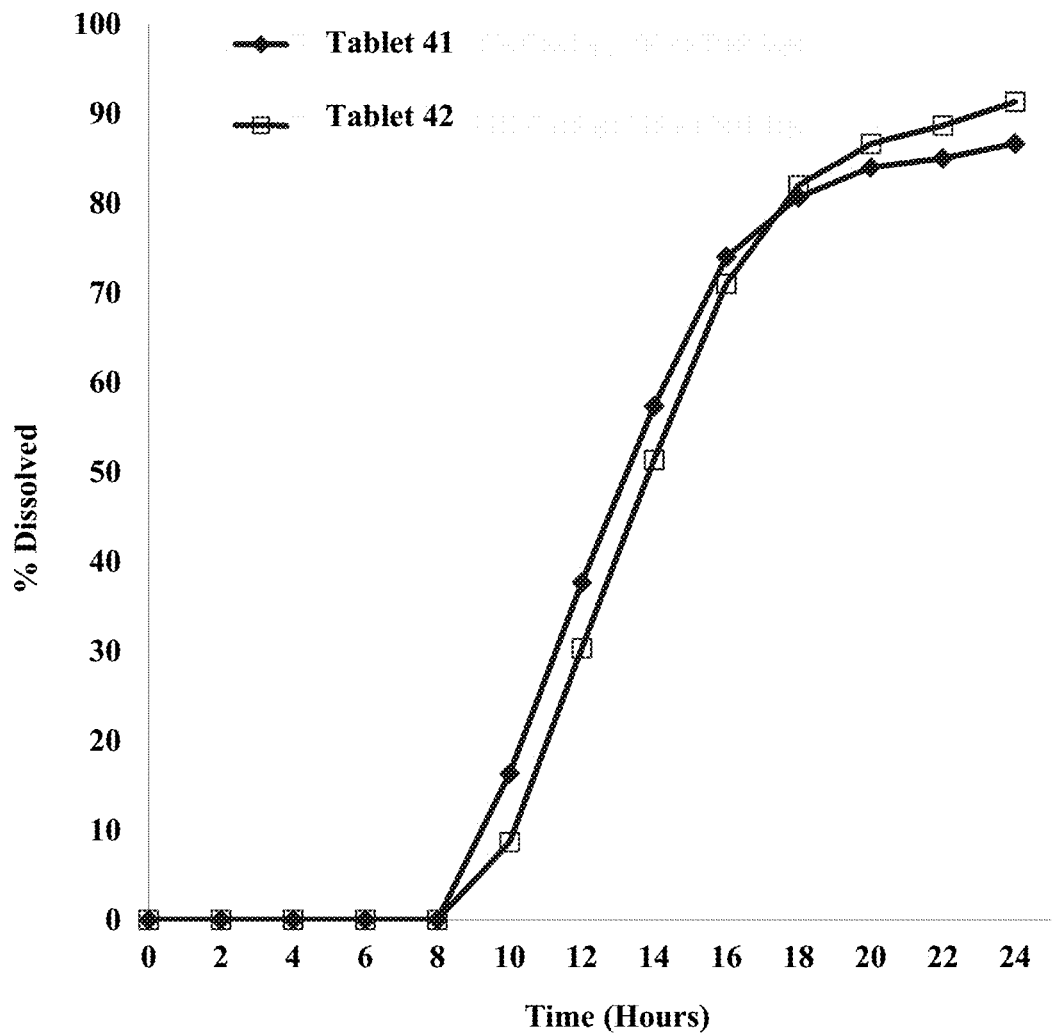

FIG. 17 compares dissolution profiles in about 900 ml of about 0.01N HCl of tablets with a drug to polymer weight ratio of about 40:60 in the push layer (Tablet 41 and Tablet 42). Percent dissolved is plotted over time (hours). The Figure demonstrates that compositions containing a drug to polymer weight ratio of about 40:60 do not show any change in lag time, and improve drug recovery, with increasing amount of push layer.

Figure 18:
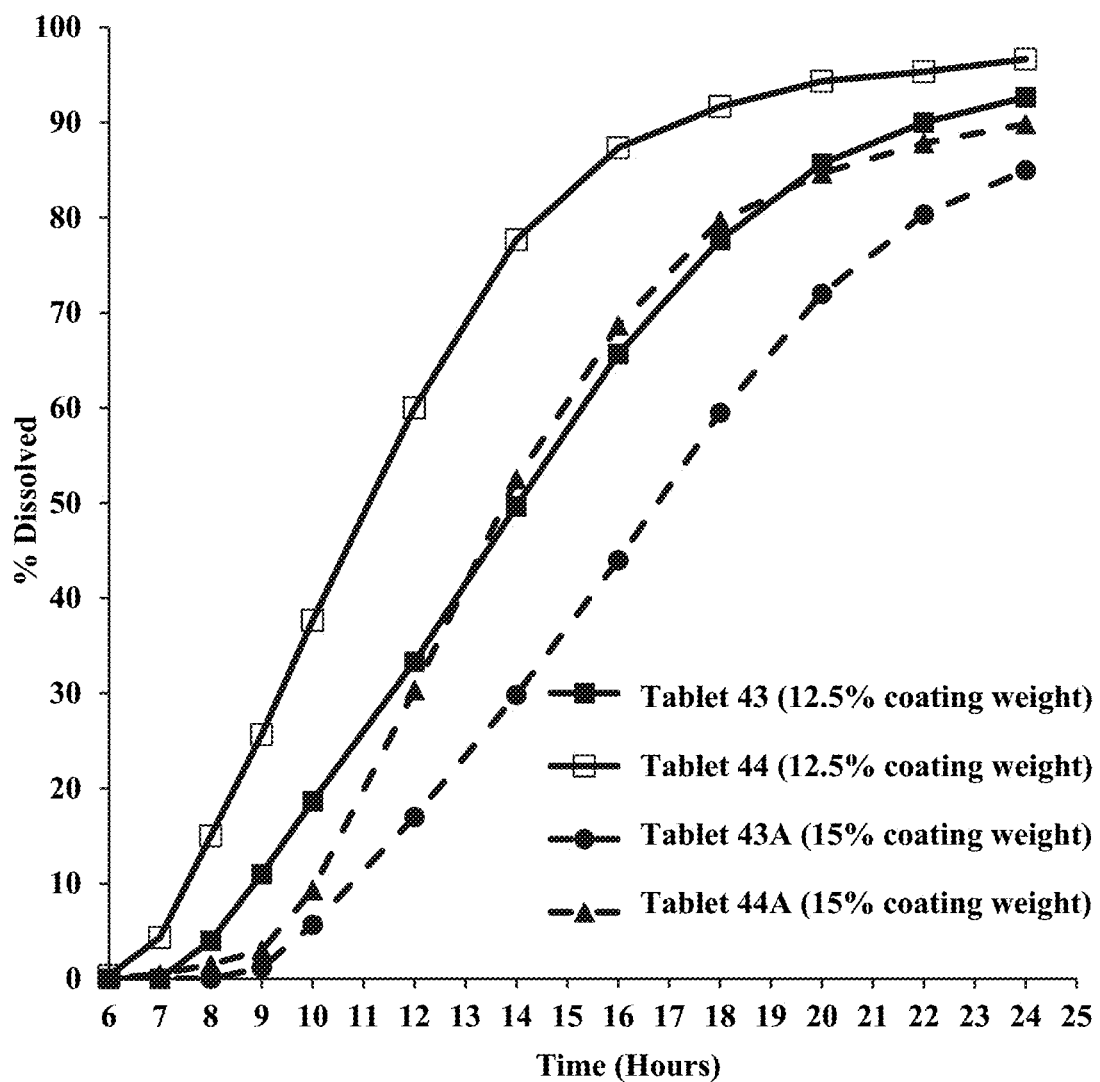

FIG. 18 dissolution profiles in about 900 ml of about 0.01N HCl of tablets with about 12.5% and about 15% coating weight gain and varying amounts of POLYOX® 1105 in the placebo layer (Tablet 43 and Tablet 44). Percent dissolved is plotted over time (hours). FIG. 18 demonstrates that lag time increases and drug recovery decreases with an increase in the coating weight gain from about 12.5% to about 15%.

Figure 19:
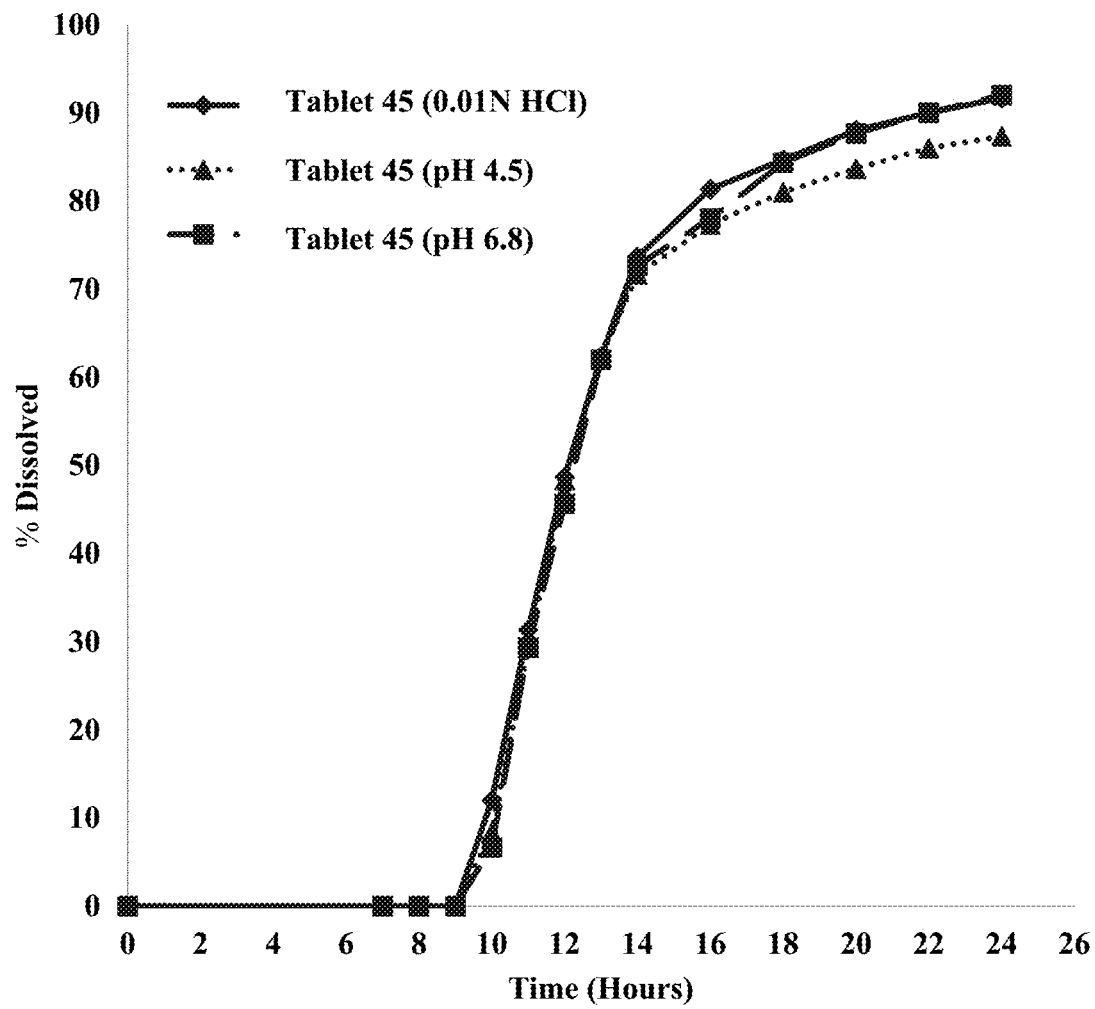

FIG. 19 compares the dissolution rates of a composition of the disclosure (Tablet 45) at pH 2 (about 0.01 N HCl), pH 4.5 acetate buffer, and pH 6.8 phosphate buffer. Percent dissolved is plotted over time (hours).

Figure 20:
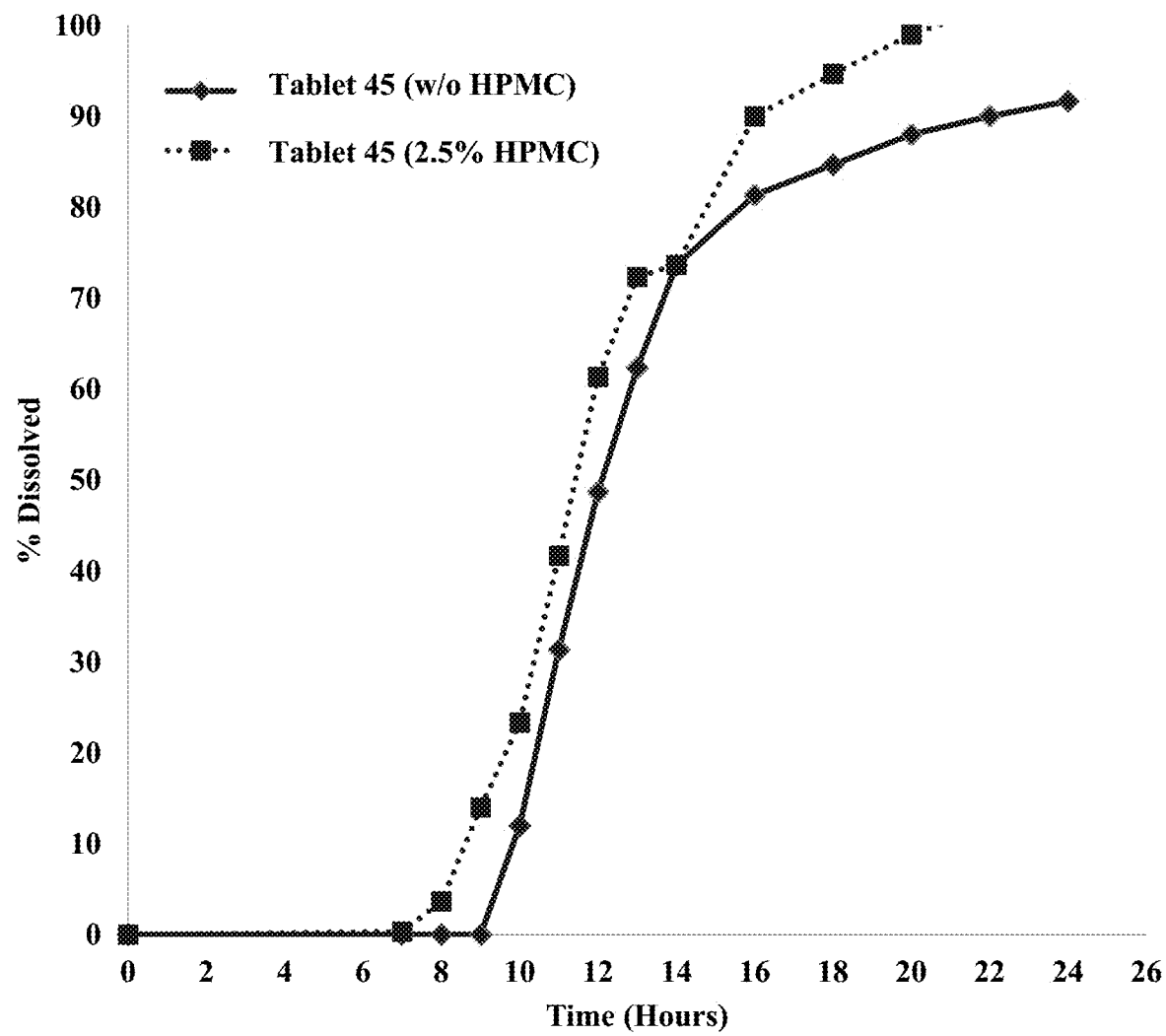

FIG. 20 provides the dissolution rates of a composition of the disclosure (Tablet 45) in dissolution mediums with different viscosities, e.g., with and without HPMC. Percent dissolved is plotted over time (hours).

Figure 21:
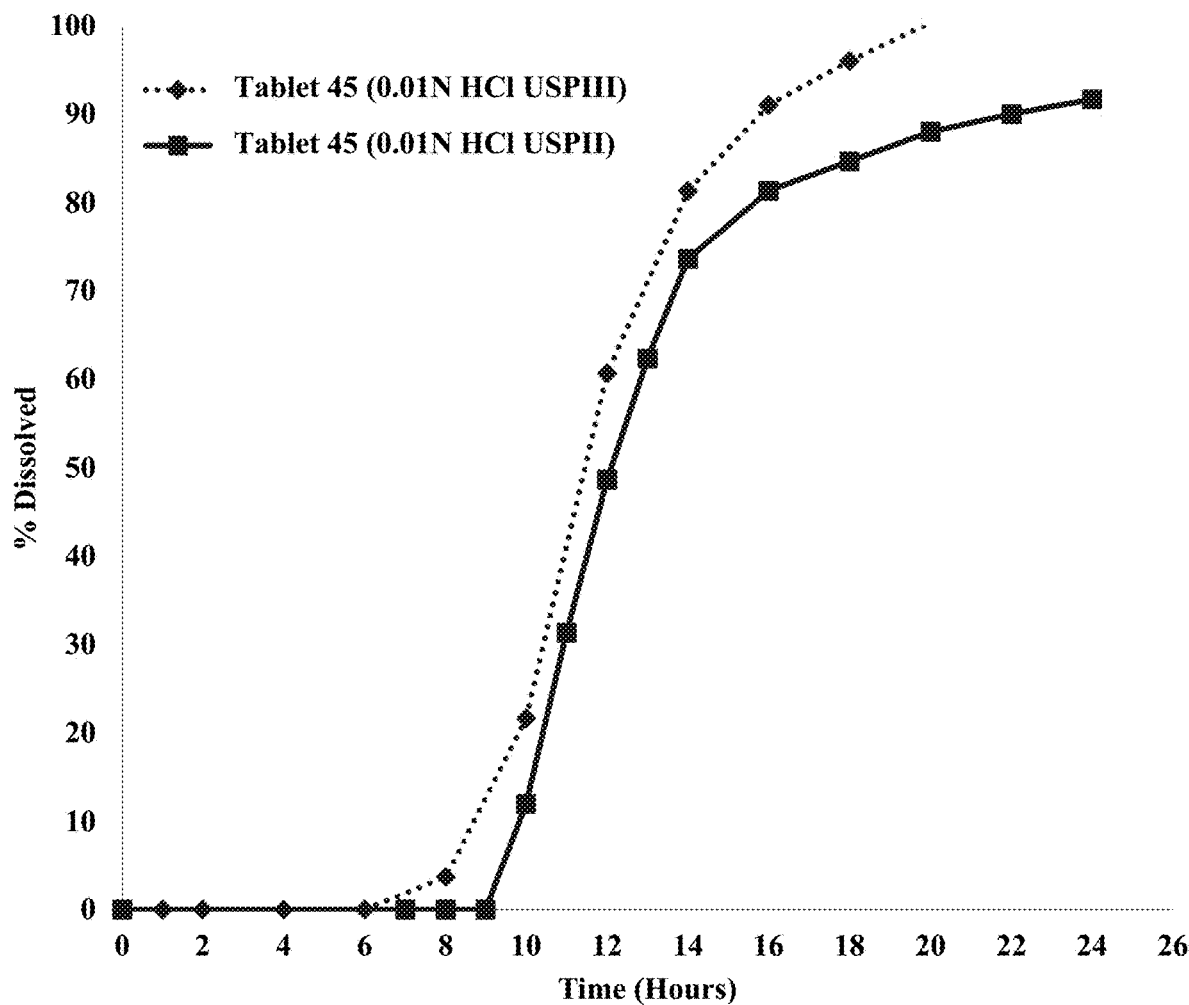

FIG. 21 compares the dissolution profiles in about 900 ml of about 0.01N HCl of tablets of a composition of the disclosure (Tablet 45), with a drug to polymer weight ratio of about 40:60, using USP Apparatus II and USP Apparatus III. Percent dissolved is plotted over time (hours).

Figure 22:
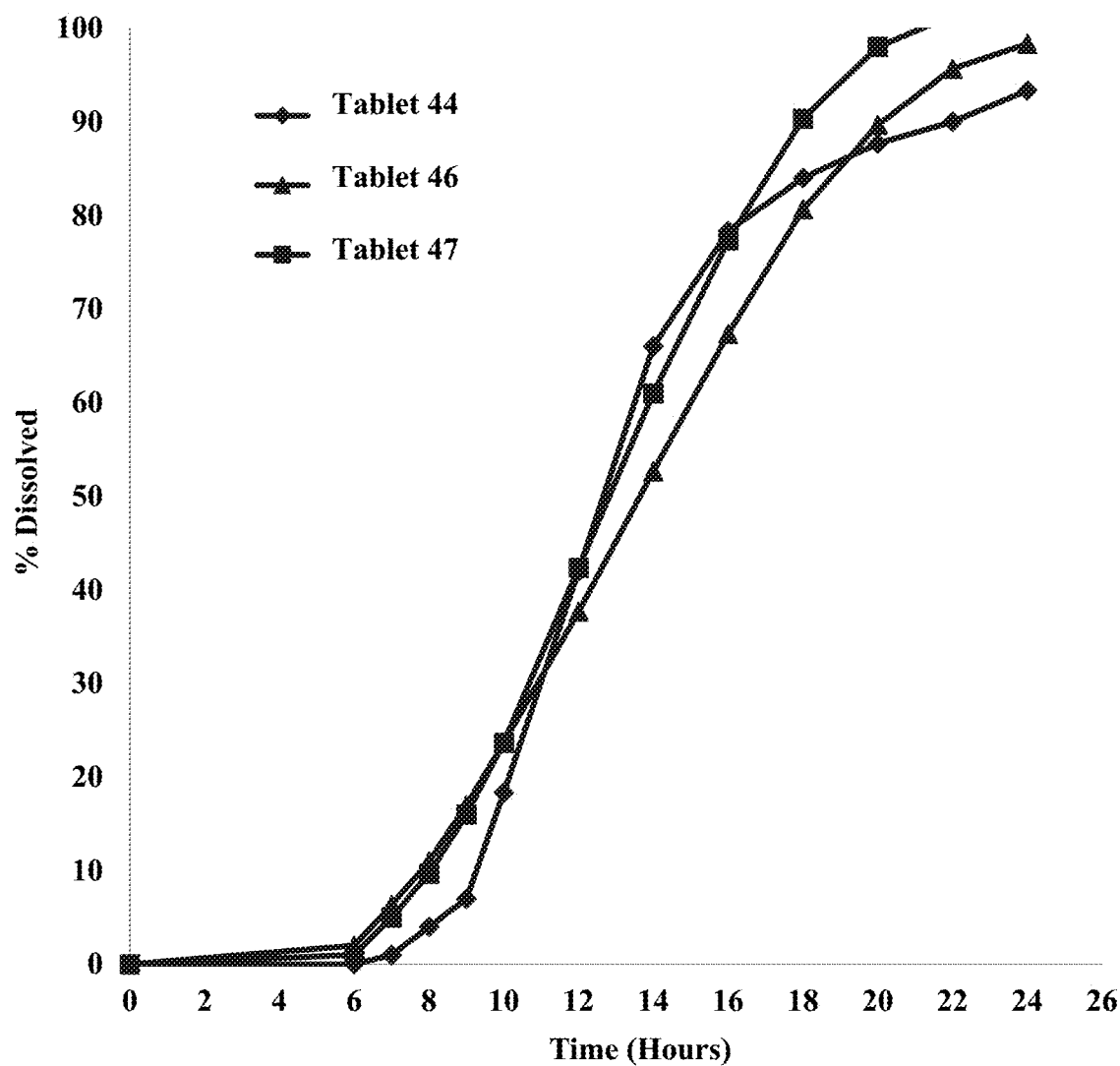

FIG. 22 compares the dissolution profiles in about 900 ml of about 0.01N HCl of tablets containing about 0% sodium chloride (Tablet 44), about 5% sodium chloride (Tablet 46), and about 10% sodium chloride (Tablet 47) in the placebo layer. Percent dissolved is plotted over time (hours).

Figure 23:
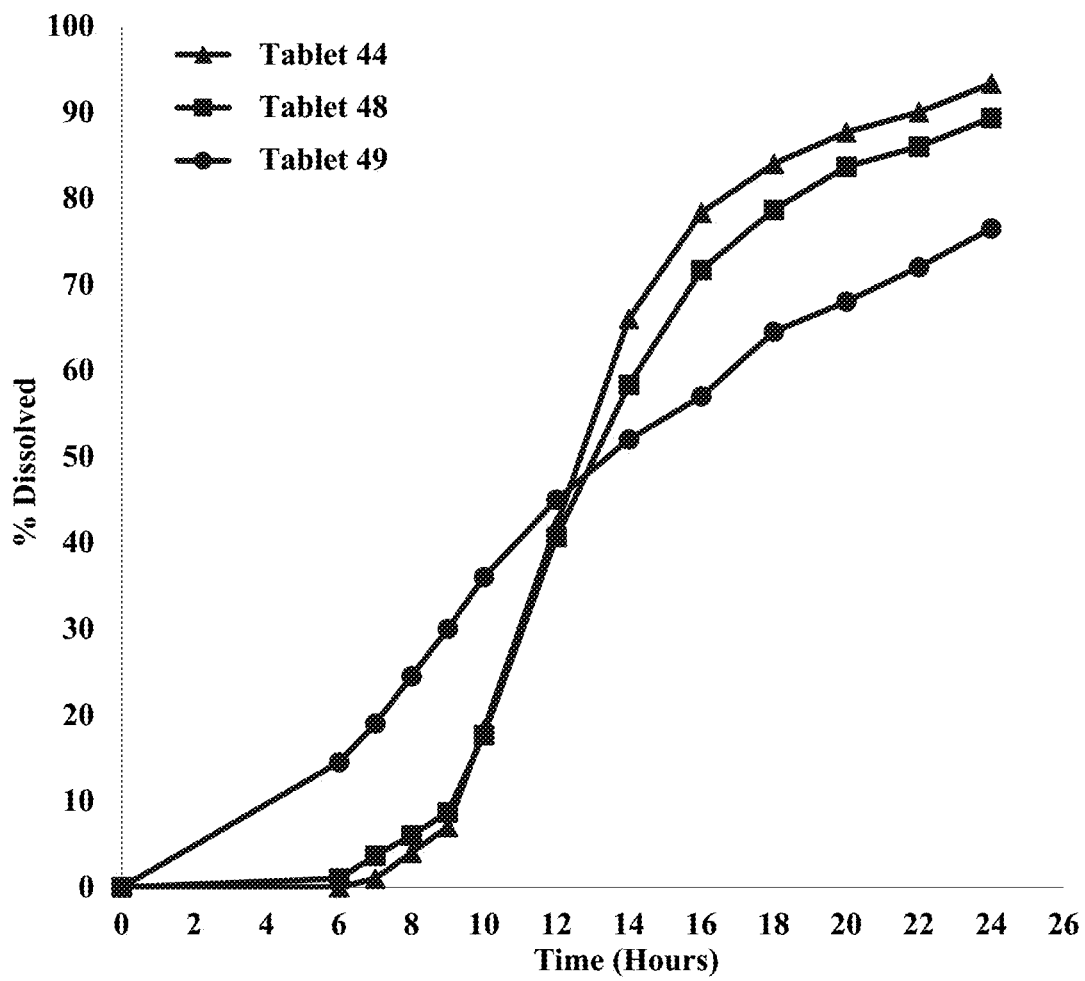

FIG. 23 compares the dissolution profiles in about 900 ml of about 0.01N HCl of tablets containing POLYOX® 1105 (Tablet 44), POLYOX® 750 (Tablet 48), POLYOX® N80 (Tablet 49), in the placebo layer. Percent dissolved is plotted over time (hours).

Figure 24:
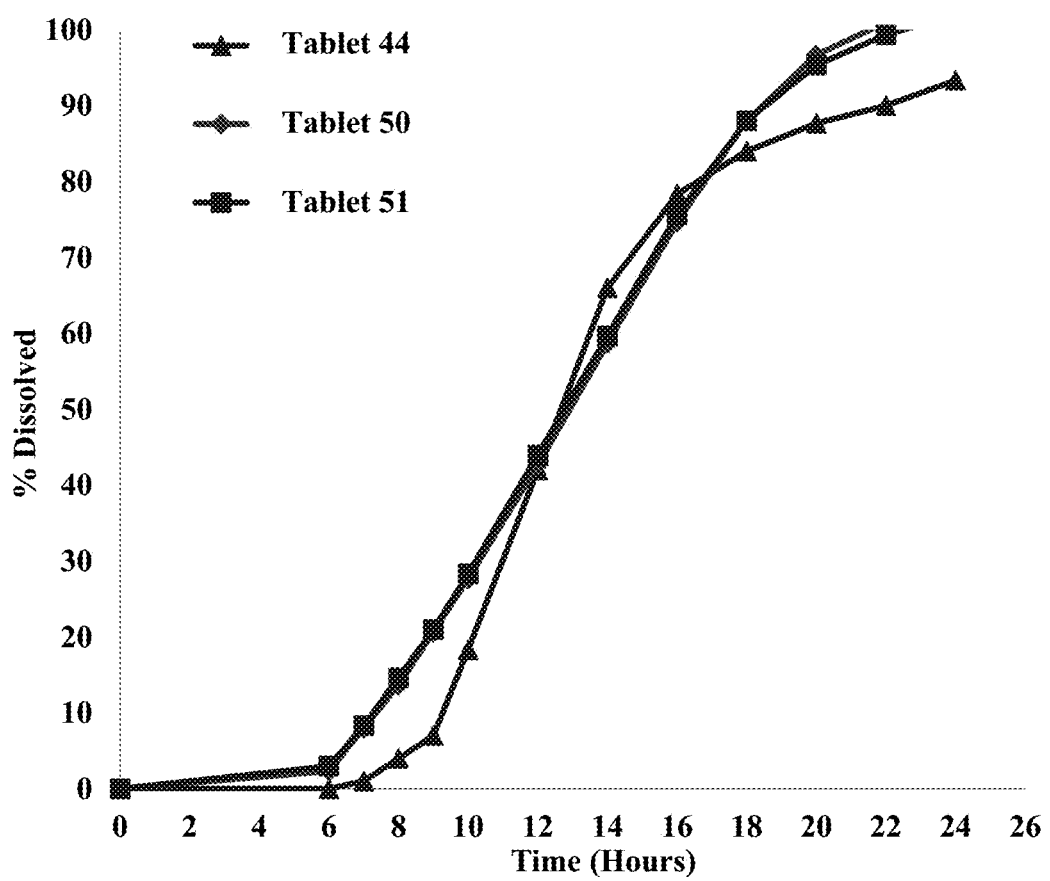

FIG. 24 compares the dissolution profiles in about 900 ml of about 0.01N HCl of tablets containing POLYOX® 303 (Tablet 44), POLYOX® 301 (Tablet 50), POLYOX® coagulant (Tablet 51) in the push layer. Percent dissolved is plotted over time (hours).

Figure 25:
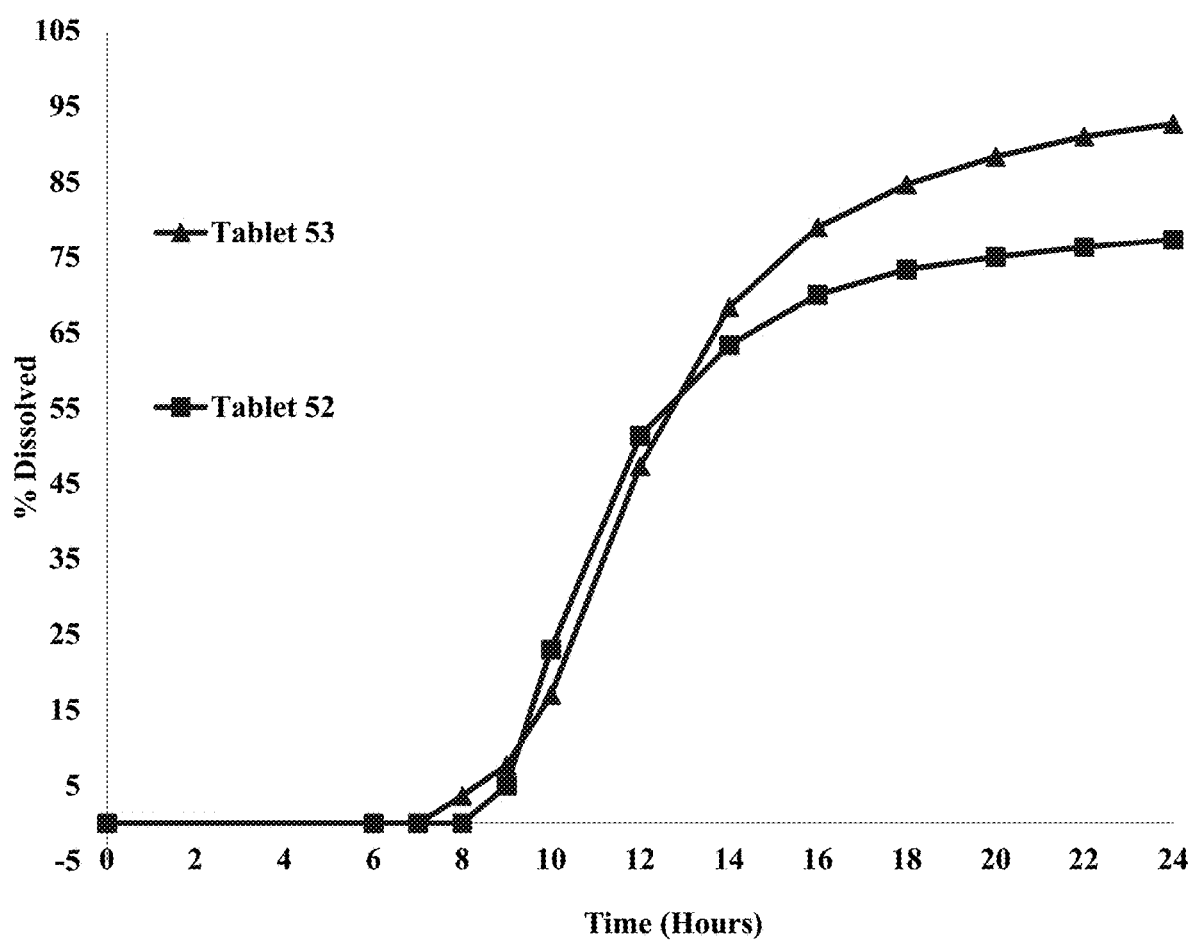

FIG. 25 compares dissolution profiles in about 900 ml of about 0.01N HCl of Tablet 52 and Tablet 53. Percent dissolved is plotted over time (hours). The Figure demonstrates that addition of a super-disintegrant and sodium chloride in the placebo layer reduces the drug recovery without substantially affecting lag time.

6. DETAILED DESCRIPTION

6.1. Definitions

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

The terminology used in the present disclosure is for the purpose of describing particular embodiments only and is not intended to be limiting.

As used herein, the use of the word "a" or "an" when used in conjunction with the term "comprising" in the claims and/or when used in the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 15%, up to 10%, up to 5%, up to 1%, up to 0.5%, or even up to 0.1% of a given value. Unless otherwise defined, all terms, including technical and scientific terms used in the description, have the same meaning as commonly understood by one of ordinary skill in the art to which this disclosure belongs. As used herein, "about" will be understood by persons of ordinary skill in the art and will vary to some extent on the context in which it is used. If there are uses of the term which are not clear to person of ordinary skill in the art given the context in which it is used, "about" will mean up to ±10% of the particular term.

As used herein, a "therapeutically effective," "therapeutic," or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject. In some embodiments, the subject is a mammal. In some embodiments, the subject is a human.

As used herein, the term "drug recovery" refers to percentage of the total amount of drug present in the dosage form that is released in a dissolution medium. The term "complete drug recovery" refers to release of about 90% to about 105% of the drug present in the dosage form.

The term "bioavailability" refers to the fraction of an administered dose of unchanged drug that reaches the systemic circulation.

As used herein, the terms "treatment," "treat," and "treating" refer to reversing, alleviating, delaying the onset of, and/or inhibiting the progress of a disease or disorder as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

The term "chrono release" refers to drug release in a sequential order of time. In particular, the term "chrono release" means timed or programmed release of one or more drugs at a rhythm that matches the human circadian rhythm of a condition's symptoms and/or of the individual being treated in the application of the therapy to optimize the therapeutic outcome and minimize side effects. In certain embodiments, the term "chrono release" comprises immediate release of a drug followed by an extended release of the same or different drug.

The term "pulsatile release" means rapid release of discrete portions of drug in pulses that are separated by a well-defined lag time(s).

The term "lag time" means the time for which release of a drug is delayed from the time of administration/ingestion of the composition. Not more than about 10% of the maximum plasma concentration (Cmax) of the drug is released during the lag time.

The term "release rate" refers to the quantity of drug released per unit time, e.g., mg of drug released per hour (mg/hour), from a dosage form. Drug release rates are calculated under in vitro dosage form dissolution testing conditions known in the art.

The term "delayed release" means release of a discrete portion(s) of a drug at a time(s) other than immediately after administration/ingestion.

The term "immediate release" means substantially complete release of a drug within a time period of about 1 hour or less, preferably within 30 minutes or less, post-administration.

The term "immediate release drug layer" means an immediate release coating layer comprising a drug and at least one pharmaceutically acceptable carrier. The immediate release drug layer dissolves rapidly upon administration and provides an immediate release dose of the drug.

The term "controlled release" means drug release that is controlled to alter the timing and/or rate of release of the drug substance from that of a conventional immediate release dosage form. The controlled release dosage forms of the disclosure can include modified release dosage forms providing delayed release (DR), extended release (ER), target release (TR), pulsatile release, chrono release, or any combination thereof, of drug substance.

The term "extended release" refers to modified release dosage forms or compositions that are formulated to allow the drug to be available over an extended period of time after administration, thereby allowing a reduction in dosing frequency, as compared to a drug presented as an immediate release dosage form.

The term "solubility" is defined in terms of ability to dissolve in water. The term "highly soluble" includes drugs with a solubility of greater than 100 mg/ml of water; the term "moderately soluble" includes drugs with a solubility of between 100 mg/ml and 1 mg/ml of water; the term "sparingly soluble" includes drugs with a solubility of between 1 mg/ml and 0.1 mg/ml of water; and the term "insoluble" includes drugs with a solubility of less than 0.1 mg/ml of water.

The term "osmosis" is defined as spontaneous movement of a solvent from a solution of lower solute concentration to a solute or a solution of higher solute concentration through a semipermeable membrane, wherein the membrane is permeable to the solvent and impermeable to the solute.

The term "osmotic pressure" is defined as pressure exerted on a higher solvent concentration side of the dosage form to inhibit solvent flow into the dosage form.

The term "substantially free" is defined as excluding any functional (e.g., noncontaminating) amount, which refers to any amount that contributes or has an effect on release profile or lag time of the composition.

The term "semipermeable membrane" is defined as a polymeric membrane or film that is substantially impermeable to the passage of solutes, e.g., a drug and other excipients, and substantially permeable to passage of fluids (e.g., water). As used herein, the terms functional coat and semipermeable membrane are used interchangeably.

The term "coating weight gain" refers to weight gain due to coating, with respect to the uncoated tablet. For example, a coating weight gain of about 15% refers to an about 15 wt % increase in tablet weight during coating with respect to the uncoated tablet weight.

The terms "pore former" and the like, as used herein, refer to water-soluble polymers and/or water-soluble small molecules that will form pores or channels (i.e., behave as a channeling agent) in a semipermeable membrane to improve permeability of the membrane.

The terms "shear" and "shear effect," as used interchangeably herein, refer to peristaltic waves, particularly under fed conditions, moving from the mid-corpus of the stomach to the pylorus. Dissolution of compositions using USP Apparatus II (Sinkers) with agitation at 50 rpm at 37° C., and using USP Apparatus III (Biodis) with agitation at 25 dpm at 37° C., mimics the effects of stomach shear on the dissolution rate of the composition.

The term "orifice" includes an opening/exit means in coatings, e.g., in the semipermeable membrane coat, the seal coat, and/or the overcoat, of an osmotic-controlled composition, to provide fluid communication with, e.g., the placebo layer. The appropriate opening can be formed by any means, e.g., by manual or laser drilling of the membrane.

The term "osmotic agent" includes swellable hydrophilic polymers, and osmogens/ionic compounds consisting of inorganic salts.

The term "patient" or "subject," as used herein, refers to a human or nonhuman mammal that is in need or may be in need to receive an osmotic dosage form of the present disclosure.

The terms "drug," "active agent," "active ingredient," and "active pharmaceutical ingredient/agent" are used interchangeably herein and include compounds that will elicit a therapeutically useful response in a subject; such terms include all pharmaceutically acceptable salts, esters, and functionally equivalent chemical compounds.

As used herein, the terms "methylphenidate" and "methylphenidate hydrochloride" are used interchangeably herein. The term "methylphenidate" includes all pharmaceutically acceptable salts, esters, and functionally equivalent chemical compounds.

As used herein, the terms "clonidine" and "clonidine hydrochloride" are used interchangeably herein. The term "clonidine" includes all pharmaceutically acceptable salts, esters, and functionally equivalent chemical compounds.

6.2. Multi-Layer Osmotic Tablet

The present disclosure provides programmable osmotic-controlled oral compositions comprising a multilayer core (e.g., a multilayer tablet core) comprising a drug, wherein the core is coated with a semipermeable membrane comprising an orifice and, optionally, an immediate release coating comprising a drug for immediate release, over the semipermeable membrane. The multilayered tablet core comprises a pull layer containing the drug and a push layer. The pull layer comprises at least two layers: a placebo layer, in fluid communication with the orifice, for providing a desired lag time for drug release; and an active layer containing the drug and providing a delayed controlled release of the drug. In certain embodiments, the tablets are vertically compressed producing a capsule-shaped product. In certain embodiments, such shape ensures complete extrusion of drug from the orifice.

For any of the dosage forms, compositions, and methods of the disclosure, the push layer is present in an amount that expands in volume to a size that pushes the entire drug solution or suspension in the pull layer, e.g., the placebo and active layers, out of the tablet through a delivery port/orifice, providing, e.g., complete drug recovery from the dosage form. In certain embodiments, the pull layer and the push layer are present in a ratio of about 2:1, about 1.5:1, about 1:1, or any intermediate values therein. In certain embodiments, the weight of push layer is about 33% or more of the total weight of the trilayer core. In certain embodiments, the weight of the placebo layer or the active layer is about 33% or more of the total weight of the trilayer core. In certain embodiments, the weight of the placebo layer or the active layer is half or more of the total weight of the trilayer core. In certain embodiments, the relative weight percentages (relative to the total weight of the trilayer core) of the placebo layer, the active layer, and the push layer can be between about 25 wt % to about 40 wt %, between about 25 wt % to about 40 wt %, and between about 20 wt % to about 50 wt %, respectively. Furthermore, each of the layers, i.e., the active layer, the placebo layer, and the push layer, can comprise polyethylene oxide (e.g., POLYOX®).

In certain embodiments, the placebo layer and the push layer are free of any active pharmaceutical ingredient. In certain embodiments, the active pharmaceutical ingredient contained in the active layer does not leach/migrate into the placebo layer or the push layer during the in vitro drug release test. In certain embodiments, during the dissolution of the placebo layer, less that about 5 wt %, less than about 4 wt %, less than about 3 wt %, less than about 2 wt %, or less than about 1wt % of the total dose of the active pharmaceutical ingredient is released within about 6 hours from the time of administration of the dosage form. Similarly, less that about 5 wt %, less than about 4 wt %, less than about 3 wt %, less than about 2 wt %, or less than about 1 wt % of the total dose of the active pharmaceutical ingredient is released between about 2 hours and about 10 hours, between about 2 hours and about 8 hours, between about 2 hours and about 7 hours, or between about 2 hours and about 6 hours following administration of the dosage form.

6.2.1. Placebo Layer: In certain embodiments, the placebo layer/placebo layer blend, is located adjacent to and in fluid communication with the orifice in the semipermeable membrane. In certain embodiments, the placebo layer blend comprises a low molecular weight swellable hydrophilic polymer, e.g., low molecular weight POLYOX®, a binder, a lubricant, and a glidant. In certain embodiments, the placebo layer further comprises a color pigment. In certain embodiments, the placebo layer blend is substantially free of any active pharmaceutical ingredient. In certain embodiments, the placebo layer contains less than about 2 wt %, less than about 1 wt %, less than about 0.5 wt %, less than about 0.2 wt %, less than about 0.1 wt %, or less than about 0.01 wt % of the active pharmaceutical ingredient.

In certain embodiments, the placebo layer blend further includes a stabilizer to prevent degradation of polyethylene oxide polymer, e.g., POLYOX®. In certain embodiments, the placebo layer blend includes granules containing POLYOX®, binder, stabilizer, and color pigment. In certain embodiments, glidant and lubricant are present as extragranular excipients in the placebo layer.

In certain embodiments, the placebo layer includes low molecular weight polyethylene oxide polymer, e.g., low molecular weight POLYOX®. In certain embodiments, the molecular weight/grade of the low molecular weight POLYOX® in the placebo layer affects drug recovery, lag time, and/or release profile, of the composition. In certain embodiments, the low molecular weight POLYOX® has an average molecular weight of <about 1M, e.g., about 100K (POLYOX® N-10), about 200K (POLYOX® N-80), about 300K (POLYOXN-750), about 600K (POLYOXN-205), about 900K (POLYOXN-1105), or intermediate values thereof. In certain embodiments, the viscosity of the placebo layer can be adjusted to provide a desired and consistent lag time. In certain embodiments, the viscosity of the placebo layer depends upon the average molecular weight of the POLYOX® present in the placebo layer. In certain embodiments, the placebo layer contains POLYOX® 205 or POLYOX® 1105. In certain embodiments, the placebo layer contains POLYOX® 1105. In certain embodiments, the low molecular weight POLYOX® is present in an amount of about 50 wt % to about 99 wt % of the placebo layer. In certain embodiments, the low molecular weight POLYOX® is present in an amount of about 50 wt %, about 55 wt %, about 60 wt %, about 65 wt %, about 70 wt %, about 75 wt %, about 80 wt %, about 81 wt %, about 82 wt %, about 83 wt %, about 84 wt %, about 85 wt %, about 86 wt %, about 87 wt %, about 88 wt %, about 89 wt %, about 90 wt %, about 91 wt %, about 92 wt %, about 93 wt %, about 94 wt %, about 95 wt %, about 96 wt %, about 97 wt %, about 98 wt %, about 99 wt %, or any intermediate values therein, of the placebo layer.

In certain embodiments, the placebo layer comprises binders including povidone, hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX®), polyethylene glycol, alginates, pegylated polyvinyl alcohol, or any combination thereof. In certain embodiments, the binder is povidone. In certain embodiments, the binders are present in an amount of about 0.5 wt % to about 20 wt % of the placebo layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediates values therein, of the placebo layer.

In certain embodiments, the placebo layer includes at least one stabilizer to prevent degradation of POLYOX®. In certain embodiments, the stabilizer comprises antioxidants including ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the antioxidant is BHT. In certain embodiments, the stabilizer is present in an amount of about 0.01 wt % to about 0.5 wt % of the placebo layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.10 wt %, about 0.2 wt %, about 0.3 wt %, about 0.4 wt %, about 0.5 wt %, or any intermediate values therein, of the placebo layer.

In certain embodiments, the placebo layer comprises at least one lubricant including magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combination thereof. In certain embodiments, the lubricant is magnesium stearate. In certain embodiments, the lubricant is present in an amount of about 0.5 wt % to about 2 wt % of the placebo layer. In certain embodiments, the lubricant is present in an amount of about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, of the placebo layer.

In certain embodiments, the placebo layer comprises at least one glidant, including talc, colloidal silicon dioxide, magnesium trisilicate, powdered cellulose, starch, tribasic calcium phosphate, or any combinations thereof. In certain embodiments, the glidant is colloidal silicon dioxide. In certain embodiments, the glidant is present in an amount of about 0.1 wt % to about 5 wt % of the placebo layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, of the placebo layer.

In certain embodiments, the placebo layer includes at least one color pigment. In certain embodiments, the color pigment in the placebo layer is useful for distinguishing the placebo layer from the active layer. In certain embodiments, the color pigment comprises iron oxide or lake-based colors. In certain embodiments, the pigment is a lake-based color. In certain embodiments, the pigment is an iron oxide pigment, e.g., oxide pigment red or oxide pigment black. In certain embodiments, the pigment is present in an amount of about 0.01 wt % to about 0.5 wt % of the placebo layer.

In certain embodiments, the placebo layer is free of functional excipients such as osmogens, any disintegrants or water-entraining agents, and glidants such as SYLLOID® 244 FP. It is surprisingly observed that the programmable osmotic-controlled oral compositions of the disclosure provide a precise lag time without the presence of any osmogen and/or water-entraining agent to imbibe water, and/or any disintegrants/wetting agents.

6.2.2. Active Layer: In certain embodiments, the active layer is located between (and adjacent to) and in contact with the placebo layer and the push layer. In certain embodiments, the active layer/active layer blend includes an active agent, a swellable hydrophilic polymer, a binder, an osmogen, and a lubricant. In certain embodiments, the active layer/active layer blend further includes a glidant and/or a stabilizer. In certain embodiments, active layer blend includes granules containing an active agent, a swellable hydrophilic polymer, a binder, an osmogen, a stabilizer, and a color pigment. In certain embodiments, glidant and lubricant are present as extragranular excipients in the active layer blend. In certain embodiments, the swellable hydrophilic polymers comprise low molecular weight hydrophilic polymers. In certain embodiments, the low molecular weight hydrophilic polymer is a swellable water-entraining polymer required to hydrate the active layer and partially dissolve or suspend drug particles. In certain embodiments, the low molecular weight hydrophilic polymers include polyethylene oxide, carbopols, polyacrylamides, acrylate polymer polysaccharide composed of condensed glucose units, crospovidone, carboxymethyl cellulose, and poly(alkalicarboxymethylcellulose), Methocel™ K100LVCR (methylcellulose and hydroxypropyl methyl cellulose), and any combinations thereof. In certain embodiments, the low molecular weight hydrophilic polymers in the active layer comprise low molecular weight polyethylene oxide polymers (e.g., POLYOX®).

In certain embodiments, drug to POLYOX® ratio, in the active layer, affects the lag time, release rate, and drug recovery of the composition. In certain embodiments, release rate and drug recovery from the composition increases with increasing the drug to POLYOX® ratio. In certain embodiments, lag time decreases with increasing drug to POLYOX® ratio. In certain embodiments, the ratio of the drug and POLYOX® is between about 10:90 and about 90:10. In certain embodiments, the ratio of the drug and POLYOX® is about 10:90, about 20:80, about 30:70, about 40:60, about 50:50, about 60:40, about 70:30, about 80:20, about 90:10, or intermediate values therein.

In certain embodiments, the grade of the polyethylene oxide polymer, and the drug to polymer ratio in the active layer, affects drug recovery, lag time, and/or release profile, of the composition. In certain embodiments, the low molecular weight POLYOX® has an average molecular weight of <1M, e.g., about 100K (POLYOX® N-10), about 200K (POLYOX® N-80), about 300K (POLYOX™ N-750), about 600K (POLYOX™ N-205), about 900K (POLYOX™ N-1105), or intermediate values thereof. In certain embodiments, the average molecular weight of POLYOX® is about 200K. In certain embodiments, the viscosity of the active layer is adjusted to provide a desired and consistent release profile. In certain embodiments, the viscosity of active layer depends upon the average molecular weight/grade of the POLYOX® present in the active layer. In certain embodiments, the active layer contains POLYOX® N-80 (200K). In certain embodiments, the low molecular weight POLYOX® is present in an amount of about 50 wt % to about 80 wt % of the active layer. In certain embodiments, the low molecular weight POLYOX® is present in an amount of about 50 wt %, about 55 wt %, about 60 wt %, about 65 wt %, about 70 wt %, about 71 wt %, about 72 wt %, about 73 wt %, about 74 wt %, about 75 wt %, about 76 wt %, about 77 wt %, about 78 wt %, about 79 wt %, about 80 wt %, or intermediate values therein, of the placebo layer.

In certain embodiments, the active layer further includes low viscosity hypromellose or hypromellose acetate succinate as a wetting agent to enhance wettability of drugs with low aqueous solubility. In certain embodiments, the low viscosity hypromellose or povidone are used as binders, and stearic acid is used as a lubricant.

In certain embodiments, the active layer comprises binders including povidone, hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX®), polyethylene glycol, alginates, pegylated polyvinyl alcohol, or any combination thereof. In certain embodiments, the binder is povidone. In certain embodiments, the binders are present in an amount of about 0.5 wt % to about 20 wt % of the active layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediates values therein, of the active layer.

In certain embodiments, the active layer comprises at least one osmogen. In certain embodiments, the osmogen includes ionic compounds of inorganic salts that provide a concentration differential for osmotic flow of liquid into the composition. In certain embodiments, the osmogen comprises an ionic compound including sodium chloride, potassium chloride, potassium sulfate, lithium sulfate, sodium sulfate, a lactose and sucrose combination, a lactose and dextrose combination, sucrose, dextrose, mannitol, dibasic sodium phosphate, and any combination thereof. In certain embodiments, the osmogen is sodium chloride. In certain embodiments, the osmogen is present in an amount of about 2 wt % to about 20 wt % of the active layer. In certain embodiments, the osmogen is present in an amount of about 2 wt %, about 3 wt %, about 4 wt %, about 5 wt %, about 6 wt %, about 7 wt %, about 8 wt %, about 9 wt %, about 10 wt %, about 15 wt %, about 20 wt %, or any intermediate values therein, of the active layer.

In certain embodiments, the active layer includes at least one stabilizer to prevent degradation of POLYOX®. In certain embodiments, the stabilizer comprises an antioxidant including one or more of ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, and propyl gallate. In certain embodiments, the antioxidant is BHT. In certain embodiments, the stabilizer is present in an amount of about 0.01 wt % to about 0.5 wt % of the active layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, or any intermediate values therein, of the active layer.

In certain embodiments, the active layer further includes surfactants to modulate the solubility of the active agent. In certain embodiments, the surfactant comprises one or more of esters of fatty acids; sorbitan fatty acid esters ethoxylated with from about 2 to about 30 moles of ethylene oxide; polyethylene glycol fatty acid esters; polyethylene glycol esters and polyethylene glycol ethers; and polyethoxylated carboxylic acids, PEG-7 hydrogenated castor oil, and PEG-30 dipolyhydroxystearate; block copolymers based on ethylene oxide and propylene oxide; dioctyl sodium sulfosuccinate (docusate sodium); sodium lauryl sulfate; PEG-32 glyceryl laurate; PEG-32 glyceryl palmitostearate; PEG-8 glyceryl caprylate/caprate; PEG-6 glyceryl caprylate/caprate; macrogol 15 hydroxystearate; polyoxyethylene 20 sorbitan monolaurate (polysorbate 20); polyoxyethylene 20 sorbitan monooleate (polysorbate 80); sorbitan monolaurate; sorbitan monooleate; and polyoxyl 40 stearate.

In certain embodiments, active layer can comprise a superdisintegrant including carmellose calcium, carboxymethylstarch sodium, croscarmellose sodium, crospovidone (crosslinked homopolymer of N-vinyl-2-pyrrolidone), low-substituted hydroxypropyl celluloses, sodium starch glycolate, colloidal silicon dioxide, alginic acid and alginates, acrylic acid derivatives, and various starches, or any combinations thereof.

In certain embodiments, the active layer comprises lubricants including magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, or any combination thereof. In certain embodiments, the lubricant is magnesium stearate. In certain embodiments, the lubricant is present in an amount of about 0.01 wt % to about 2 wt % of the active layer. In certain embodiments, the lubricant is present in an amount of about 0.01 wt %, about 0.02 wt %, about 0.03 wt %, about 0.04 wt %, about 0.05 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, of the active layer.

In certain embodiments, the active layer comprises glidants including talc, colloidal silicon dioxide, magnesium trisilicate, powdered cellulose, starch, tribasic calcium phosphate, or a mixture thereof. In certain embodiments, the glidant is colloidal silicon dioxide. In certain embodiments, the glidant is present in an amount of about 0.1 wt % to about 5 wt % of the placebo layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, of the active layer.

6.2.3. Push Layer: In certain embodiments, the push layer is located adjacent to the active layer. In certain embodiments, the push layer/push layer blend includes a swellable hydrophilic polymer, a binder, an osmogen, a lubricant, and a color pigment. In certain embodiments, the push layer/push layer blend further includes a glidant and/or a stabilizer. In certain embodiments, the push layer does not include any drug. In certain embodiments, the swellable hydrophilic polymer is a high molecular weight polyethylene oxide polymer (e.g., high molecular weight POLYOX®). In certain embodiments, the push layer blend includes granules containing one or more of high molecular weight POLYOX®, binder, osmogen, stabilizer, and color pigment. In certain embodiments, the glidant and lubricant are present as extragranular excipients in the push layer blend. In certain embodiments, the osmogen provides a concentration gradient for osmotic flow of liquid into the composition. The rate at which the high molecular weight water-soluble polymer in the push layer absorbs water depends on the osmotic pressure generated by the osmogen in the push layer and the permeability of the membrane coating. As the water-soluble polymer in the push layer absorbs water, it expands in volume, which pushes the drug solution or suspension in the pull layer out of the tablet through a delivery port/orifice. The compositions release drug at a rate that is independent of pH and the hydrodynamics of the dissolution medium.

In certain embodiments, the presence of osmotic agents, e.g., POLYOX® and ionic osmogens, e.g., sodium chloride, in the push layer of tablet core, is critical to produce uniform swelling of the tablet core. In certain embodiments, the osmotic agents in the push layer comprise high molecular weight POLYOX® and milled sodium chloride.

In certain embodiments, the high molecular weight POLYOX® in the push layer has an average molecular weight of ≥1M, e.g., about 1M (POLYOX® WSR N 12K), about 2M (POLYOX® WSR N 60K), about 4M (POLYOX® WSR 301), about 5M (POLYOX® coagulant), about 7M (POLYOX® WSR 303), or any intermediate values thereof. In certain embodiments, swelling of POLYOX® coagulant (5M) can be enhanced by mixing with a portion of POLYOX® WSR 303 (7M). In certain embodiments, swelling of POLYOX® coagulant can be reduced by mixing with a portion of POLYOX® WSR 301 (4M). In certain embodiments, the high molecular weight POLYOX® is present in an amount of about 50 wt % to about 80 wt % of the push layer. In certain embodiments, the high molecular weight POLYOX® is present in an amount of about 50 wt %, about 55 wt %, about 60 wt %, about 65 wt %, about 70 wt %, about 75 wt %, about 80 wt %, or any intermediate values therein, of the push layer.

In certain embodiments, the amount and grade of the high molecular weight POLYOX® in the push layer affects the drug release profile from the dosage form, i.e., an increase in the molecular weight or amount of the high molecular weight POLYOX® in the push layer will increase the volume of the push layer and the force exerted on the pull layer for fast and complete drug recovery. In certain embodiments, the grade of the high molecular weight POLYOX® in the push layer is selected to provide rapid expansion and complete drug recovery in about 22 hours from the time of administration of the dosage form. In certain embodiments, the grade of the high molecular weight POLYOX® in the push layer is selected to provide rapid expansion without tearing of the semipermeable membrane.

In certain embodiments, the push layer comprises binders including povidone, hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX®), polyethylene glycol, alginates, pegylated polyvinyl alcohol, or any combination thereof. In certain embodiments, the binder is povidone.

In certain embodiments, the binders are present in an amount of about 0.5 wt % to about 20 wt % of the push layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, or any intermediates values therein, of the push layer.

In certain embodiments, the push layer includes at least one stabilizer to prevent degradation of POLYOX®. In certain embodiments, the stabilizer comprises antioxidants including ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, or any combination thereof. In certain embodiments, the antioxidant is BHT. In certain embodiments, the stabilizer is present in an amount of about 0.01 wt % to about 0.5 wt % of the push layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, or any intermediate values therein, of the push layer.

In certain embodiments, the push layer comprises lubricants including magnesium stearate, glyceryl monostearates, palmitic acid, talc, carnauba wax, calcium stearate sodium, sodium or magnesium lauryl sulfate, calcium soaps, zinc stearate, polyethylene oxide, polyethylene glycols, polyoxyethylene monostearates, calcium silicate, silicon dioxide, hydrogenated vegetable oils and fats, stearic acid, or any combination thereof. In certain embodiments, the lubricant is stearic acid.

In certain embodiments, the lubricant is present in an amount of about 0.1 wt % to about 2 wt % of the push layer. In certain embodiments, the lubricant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, of the push layer.

In certain embodiments, the push layer comprises at least one glidant including talc, colloidal silicon dioxide, magnesium trisilicate, powdered cellulose, starch, and tribasic calcium phosphate. In certain embodiments, the glidant is colloidal silicon dioxide. In certain embodiments, the glidant is present in an amount of about 0.1 wt % to about 5 wt % of the push layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, or any intermediate valued therein, of the push layer.

In certain embodiments, the push layer comprises at least one osmogen. In certain embodiments, the osmogen comprises ionic compounds of inorganic salts that provide a concentration differential for osmotic flow of liquid into the composition. The rate at which the high molecular weight water-soluble polymer in the push layer absorbs water depends on the osmotic pressure generated by the push layer and the permeability of the semipermeable membrane coating. As the water-soluble polymer in the push layer absorbs water, it expands in volume, which pushes the drug solution or suspension present in the active layer out of the tablet core through a delivery port/orifice in the membrane. In certain embodiments, the osmogen is an ionic compound comprising sodium chloride, potassium chloride, potassium sulfate, lithium sulfate, sodium sulfate, a lactose and sucrose combination, a lactose and dextrose combination, sucrose, dextrose, mannitol, dibasic sodium phosphate, and combinations thereof. In certain embodiments, the osmogen is sodium chloride. In certain embodiments, the osmogen is present in an amount of about 5 wt % to about 30 wt % of the push layer. In certain embodiments, the osmogen is present in an amount of about 5 wt %, about 6 wt %, about 7 wt %, about 8 wt %, about 9 wt %, about 10 wt %, about 15 wt %, about 20 wt %, about 25 wt %, about 30 wt %, or any intermediate values therein, of the push layer.

In certain embodiments, the push layer includes at least one color pigment for identifying the push layer in the multilayered tablet core. In certain embodiments, the push layer and the placebo layer include the same color pigment. In certain embodiments, the placebo layer contains less amount of color pigment than the push layer. In certain embodiments, the push layer is darker in color than the placebo layer, which helps in identifying the placebo layer side while drilling a delivery orifice in the membrane that is in fluid communication with the placebo layer. In certain embodiments, the push layer comprises at least one pigment including iron oxide or lake-based colors. In certain embodiments, the pigment is a lake-based color. In certain embodiments, the pigment is an iron oxide pigment, e.g., oxide pigment red or oxide pigment black. In certain embodiments, the pigment is present in an amount of about 0.5 wt % to about 2 wt % of the push layer.

6.2.4. Semipermeable Membrane: In certain embodiments, the trilayer tablet core is coated with a semipermeable membrane. In certain embodiments, the semipermeable membrane is a polymeric film coating containing at least one orifice in fluid communication with placebo layer.

In certain embodiments, the perforation of a semipermeable membrane is achieved through manual or laser drilling. In certain embodiments, the orifice size is less than about 1000 μm. In certain embodiments, the orifice size is about 950 μm, about 900 μm, about 850 μm, about 800 μm, about 750 μm, about 700 μm, about 650 μm, about 600 μm, about 550 μm, about 500 μm, about 450 μm, about 400 μm, about 350 μm, about 300 μm, about 250 μm, or about 200 μm. In certain embodiments, it is important that the semipermeable membrane is adequately perforated with an orifice without compromising the integrity of the tablet core.

In certain embodiments, the coating composition and/or coating weight gain of the semipermeable membrane determines the lag time provided by the composition. In certain embodiments, the coating weight gain of the semipermeable membrane ranges from about 1 wt % to about 50 wt %, about 5 wt % to about 45 wt %, about 5 wt % to about 40 wt %, about 5 wt % to about 35 wt %, about 5 wt % to about 30 wt %, from about 5 wt % to about 25 wt %, from about 5 wt % to about 20 wt %, from about 5 wt % to about 15 wt %, from about 5 wt % to about 10 wt %, or any intermediate ranges therein, of the tablet core weight.

In certain embodiments, the semipermeable membrane coat over the multilayered tablet core is substantially impermeable to drugs and excipients present in the programmable osmotic-controlled oral composition. In certain embodiments, the semipermeable membrane is inert and maintains its integrity to provide constant osmotic pressure during drug delivery. In certain embodiments, the semipermeable membrane comprises one or more pH-independent water-insoluble polymers that are permeable to water and substantially impermeable to solutes, e.g., drugs and excipients. Polymers suitable for inclusion in the semipermeable membrane comprise cellulose esters, e.g., cellulose acetate, cellulose acetate butyrate, and cellulose triacetate. In certain embodiments, the semipermeable membrane comprises cellulose acetate. In certain embodiments, the permeability of the semipermeable membrane can be enhanced by increasing the acetyl content in cellulose acetate. In certain embodiments, the semipermeable membrane comprises cellulose acetate with at least about 35% acetyl content. In certain embodiments, the semipermeable membrane comprises cellulose acetate with about 39.8% acetyl content. In certain embodiments, permeability of the semipermeable membrane is enhanced by addition of water-soluble pore formers to the membrane composition. In certain embodiments, the water-soluble pore formers comprise polyethylene glycol (PEG 400, PEG 1000, PEG 1450, PEG 3350), hydroxypropyl cellulose, polyvinyl pyrolidone (PVP), KOLLIDON® 30, KOLLICOAT® IR, mannitol, and methyl cellulose (METHOCEL™ E3, METHOCEL™ E5, METHOCEL™ E6), poloxamers, e.g., poloxamer 188, triethyl citrate, triacetin, hydroxypropyl methylcellulose, glycerol, and combination thereof. In certain embodiments, the semipermeable membrane comprises cellulose acetate and a pore-forming copolymer such as polypropylene glycol and/or poloxamers, e.g., poloxamer 188. In certain embodiments, the ratio of cellulose acetate to polyethylene glycol is between about 80:20 and about 99.5:0.5. In certain embodiments, the ratio of cellulose acetate to poloxamer is between about 80:20 and about 99.5:0.5. In certain embodiments, ratio of cellulose acetate and pore former affects variability in lag time. In certain embodiments, variability in lag time decreases with increasing the amount of pore former in the membrane. In certain embodiments, lag time decreases with increasing the amount of pore former in the membrane. In certain embodiments, the ratio of cellulose acetate and pore former is optimized to obtain a desired lag time with minimal variability. In certain embodiments, the ratio of cellulose acetate and pore former is about 80:20, about 85:15, about 90:10, about 95:5, about 96:4, about 97:3, about 98:2, about 99:1, about 99.5:0.5, or any intermediate values therein.

In certain embodiments, the semipermeable membranes include one or more plasticizers. Plasticizers play a significant role in adjusting flexibility and permeability of the semipermeable membrane. Plasticizers change the viscoelastic behavior and permeability of the polymer present in the semipermeable membrane. Plasticizers used in the semipermeable membranes comprise polyethylene glycols, triethyl citrate, triacetin, diethyl tartrate, and combinations thereof. In certain embodiments, the pore former comprises polyethylene glycol (PEG 400, PEG 1000, PEG 1450, PEG 3350), hydroxypropyl cellulose, polyvinyl pyrolidone (PVP), KOLLIDON® 30, KOLLICOAT® IR, mannitol, and methyl cellulose (METHOCEL™ E3, METHOCEL™ E5, METHOCEL™ E6).

In certain embodiments, solvents for coating comprise water, acetone, and/or any mixtures thereof. In certain embodiments, the programmable osmotic-controlled oral compositions of the disclosure include an aesthetic coat over the semipermeable membrane. In certain embodiments, the aesthetic coat comprises colors, flavors, and sweeteners. In certain embodiments, the aesthetic coat is the outermost coat comprising OPADRY® II for pigmentation or OPADRY® clear for final glossiness. In certain embodiments, the aesthetic coat further comprises wax to improve flow for packaging.

6.2.5. Active Pharmaceutical Agents: In certain embodiments, the programmable osmotic-controlled oral compositions of the disclosure are suitable for drugs/active pharmaceutical agents comprising any level of aqueous solubilities.

In certain embodiments, drugs suitable for the programmable osmotic-controlled composition of the disclosure include CNS-acting drugs, cardiovascular-acting drugs, anti-infectives, analgesics, anesthetics, antiarthritics, antiasthmatics, anticonvulsants, antidepressants, antidiabetics, antidiarrheals, antihistamines, anti-inflammatories, antimigraines, antineoplastics, antiparkinson drugs, antipruritics, antipsychotics, antipyretics, antispasmodics, anticholinergics, sympathomimetics, calcium channel blockers, beta blockers, antiarrhythmics, antihypertensives, ACE inhibitors, diuretics, vasodilators, decongestants, hormones, hypnotics, immunosuppresives, parasympathomimetics, prostaglandins, proteins, peptides, sedatives and tranquilizers.

In certain embodiments, drugs suitable for delayed release include amphetamines, methylphenidate, diltiazem, carbamazepine, metoprolol, oxprenolol, nifedipine, albuterol, phenylpropanolamine, pseudoephedrine, chlorpheniramine maleate, prazosin, doxazosin, verapamil, oxybutynin chloride, isradipine, hydromorphone, paliperidone, modafinil, armodafinil, liothyronine, oseltamivir (Tamiflu), rifamycin, and glipzide.

In certain embodiments, compositions of the disclosure provide chrono drug release and are designed to treat, e.g., diseases in which biological rhythm(s) play a vital role in the pathophysiology of such diseases to avoid degradation of bioactive agents. In certain embodiments, the compositions of the disclosure are used to treat conditions that require chrono drug release, e.g., attention disorders, asthma, arthritis, congestive heart failure, myocardial infarction, stroke, cancer, peptic ulcer, epilepsy, migraine, pain, etc., wherein the risk and symptoms of the disease vary predictably over time.

In certain embodiments, chrono release compositions of the disclosure include antibiotics such as gentamycin, tobramycin, and amikacin; antihypertensives such as nifedipine, oral nitrates, propranolol, and atenolol; antiepileptic drugs such as valproic acid; anti-inflammatory drugs such as indomethacin and ketoprofen; anti-asthmatic drugs such as theophylline and beta sympathomimetics; anti-ulcer drugs such as ranitidine, cimetidine, and famotidine; anticancer drugs; NSAIDs for treating arthritis; antihyperlipidemic drugs, such as statins; opioid analgesics such as tramadol; antimigraine drugs such as sumatriptan; immunosuppressants such as cyclosporine; local anesthetics such as lidocaine, ropivacaine, mepivacaine, and betoxycaine; and general anesthetics such as barbiturates.

In certain embodiments, immediate release sedatives suitable for the programmable osmotic-controlled compositions of the disclosure include clonidine, diphenhydramine, guanfacine, and/or melatonin.

6.3. Embodiments of the Dosage Form: In certain embodiments, additional programmable osmotic-controlled compositions containing additional pull layers, IR coatings, etc. are contemplated. A nonlimiting set of exemplary osmotic-controlled compositions follows.

In certain embodiments, the programmable osmotic-controlled composition of the disclosure comprises a combination composition providing an immediate release of a sedative and a delayed extended release of a stimulant. In certain embodiments, the programmable osmotic-controlled composition of the disclosure comprises a multilayer tablet core coated with a semipermeable membrane containing an orifice, and a coating of a sedative for immediate release, over the semipermeable membrane. In certain embodiments, the tablet core comprises multiple layers in the following order: a placebo layer in fluid communication with orifice in the semipermeable membrane, a delayed extended release layer containing a stimulant, and a push layer, wherein the push layer is away (e.g., furthest away) from the orifice in the semipermeable membrane.

In certain embodiments, the programmable osmotic-controlled composition of the disclosure is a combination composition providing an extended release of a sedative and a delayed extended release of a stimulant. In certain embodiments, the programmable osmotic-controlled composition of the disclosure comprises an IR coat containing a sedative, a seal coat below the IR sedative coat, an ER coat containing a sedative and below the seal coat, a cellulose acetate coat containing an orifice below the ER sedative coat, a "placebo" layer in fluid communication with the orifice, a delayed extended release layer containing a stimulant and placed below the placebo layer, and a push layer placed below the delayed extended release layer and facing away from the orifice.

In certain embodiments, the programmable osmotic-controlled composition of the disclosure comprises a combination composition providing immediate release of a sedative and a chrono release of a stimulant. In certain embodiments, the composition comprises a multilayer tablet core coated with a semipermeable membrane containing an orifice, and a coating of a drug for immediate release over the semipermeable membrane.

In certain embodiments, the multilayered tablet core comprises a push layer, and a pull layer comprising a placebo layer and an active layer containing a stimulant, wherein the active layer comprises an immediate release layer and an extended release layer for providing chrono release of the stimulant. In certain embodiments, the tablet core comprises multiple layers in the following order: a placebo layer in fluid communication with the orifice in the semipermeable membrane, a delayed immediate release layer containing a stimulant, a delayed extended release layer containing a stimulant, and a push layer, wherein the push layer is furthest away from the orifice in the semipermeable membrane. In certain embodiments, the delayed immediate release layer and the delayed extended release layer contain the same stimulant.

In certain embodiments, the programmable osmotic-controlled composition of the disclosure comprises a combination composition providing an immediate release of a sedative and a delayed chrono release of a stimulant, wherein the immediate release sedative is present as an immediate release layer in the tablet core. In certain embodiments, the tablet core comprises multiple layers in the following order: an immediate release layer containing a sedative and in fluid communication with the orifice in the semipermeable membrane, a placebo layer, a delayed immediate release layer, containing a stimulant, a delayed extended release layer containing a stimulant, and a push layer facing away from the orifice. In certain embodiments, the delayed immediate release layer and the delayed extended release layer contain the same stimulant.

In certain embodiments, the programmable osmotic-controlled composition of the disclosure provides pulsatile release of a drug. In certain embodiments, the composition comprises a multilayer tablet core coated with an IR coat comprising a drug, and a coating of a semipermeable membrane containing an orifice below the IR coat. In certain embodiments, the tablet core comprises multiple layers in the following order: a placebo layer in fluid communication with the orifice in the semipermeable membrane, a delayed immediate release layer comprising the drug, and a push layer, to provide pulsatile release of a drug in two pulses. In certain embodiments, the tablet core comprises a first placebo layer in fluid communication with the orifice in the semipermeable membrane, a first delayed immediate release layer comprising a stimulant, a second placebo layer, a second delayed immediate release layer, and a push layer, to provide a pulsatile release of a drug in three pulses.

In certain embodiments, the programmable osmotic-controlled composition of the disclosure comprises a combination composition providing an immediate release of a sedative and a delayed increasing (gradient) release of a stimulant. In certain embodiments, the composition comprises a multilayer tablet core coated with a semipermeable membrane containing an orifice. In certain embodiments, the tablet core comprises multiple layers in the following order: a placebo layer in fluid communication with the orifice in the semipermeable membrane, at least two delayed release layers comprising a stimulant for delayed release, and a push layer, wherein the at least two delayed release layers releases the stimulant over a period of at least two successive intervals, wherein more stimulant is released in the second interval compared to the first interval.

In certain embodiments, the viscosity of the placebo layer, the active layer, and the push layer, and the drug to polymer ratio in the active layer determine the release rate of the drug as an immediate release portion or an extended release portion. In certain embodiments, an immediate release layer will comprise a higher drug to polymer ratio compared to an extended release layer containing the same drug and the polymer.

In certain embodiments, the dosage form of the disclosure comprises an immediate release coat and an extended release coat of the sedative, and the two coats are separated by a seal coat.

In certain embodiments, the seal coat comprises hydroxypropyl methyl cellulose (HPMC), hydroxypropyl cellulose, hydroxyethyl cellulose, or povidone. In certain embodiments, the seal coat is present in an amount of between about 1 wt % to about 20 wt %, about 5 wt % to about 20 wt %, or about 5 wt % to about 15 wt % of the tablet core weight without seal coat.

In certain embodiments, the exemplary clinical situation described herein involves treatment of ADHD/ADD with an immediate release sedative and delayed release stimulant therapy. Accordingly, the present disclosure also pertains to making oral methylphenidate delayed release dosage forms that provide an immediate release of a sedative and delayed release of methylphenidate over an extended time period.

6.4. Features of the Dosage Form

The present disclosure provides programmable osmotic-controlled oral compositions that provide delayed controlled release of a drug, and can be programmed to release drug at a desired time and for a desired duration, e.g., at a rhythm that matches the requirements for treatment in a sleep/wake cycle, or at a rhythm that matches the human circadian rhythm of a condition's symptom and/or of the individual being treated in the application of the therapy, with complete drug recovery. The osmotic-controlled oral compositions of the disclosure can be programmed to control lag time during the delay period and release drug at a desired rate after the delay period. In certain embodiments, the osmotic-controlled oral compositions are programmed to provide a precise lag time of at least about 4, 5, 6, 7, 8, 9, 10, 11, 12 hours, or intermediate time periods within the range. In certain embodiments, the programmable osmotic-controlled oral compositions of the disclosure provide delayed extended release, delayed chrono release, delayed pulsatile release, and pulsatile release of drugs with various doses and solubilities, and can be programmed to release drug at a rate that matches the human circadian rhythm of a condition's symptom and/or of the individual being treated in the application of the therapy. The programmable osmotic-controlled oral compositions of the disclosure provide pH-independent drug release at an osmotically determined rate for an extended time period, even as the dosage form transits the GI tract and encounters variable hydrodynamic environments of the GI tract, as well as microenvironments with significantly different pH values. In certain embodiments, the programmable osmotic-controlled oral compositions of the disclosure provide delayed controlled release of a drug, with minimum variability in lag time in response to varying pH and hydrodynamic conditions of a dissolution medium or the human GI tract.

In certain embodiments, the programmable osmotic-controlled oral compositions of the disclosure provide an immediate release of a sedative and delayed extended release of methylphenidate hydrochloride. In certain embodiments, the timing of administration of the composition (e.g., in the evening) is titrated to optimize the tolerability and efficacy of the dose, as seen during, e.g., the next morning and throughout the day. In certain embodiments, the osmotic-controlled oral compositions of the active agent (e.g., methylphenidate) are programmed to provide drug release as follows: a lag time of at least about, e.g., 6-8 hours, a controlled release comprising about 20% of drug release in about 1-4 hours after the lag time, and an extended release of the drug with about 100% drug recovery in about 10-15 hours after the lag time (or about 22 hours from the time of administration of the composition). In certain embodiments, the disclosure provides programmable osmotic-controlled oral compositions of, e.g., methylphenidate that can be programmed to limit the amount of methylphenidate in plasma to less than about 10% of the maximum concentration (Cmax) during the lag time to avoid side effects, e.g., insomnia; in addition, the programmable osmotic-controlled oral compositions limit the amount of methylphenidate in plasma to less than about 10% of the Cmax beginning about 22 hours after the time of administration, to avoid side effects, e.g., insomnia.

The programmable osmotic-controlled oral compositions of the disclosure can comprise a multilayer tablet core comprising a drug, wherein the core is coated with a semipermeable membrane comprising an orifice and, optionally, an immediate release drug layer coating/immediate release drug layer, comprising a drug for immediate release, over the semipermeable membrane. In certain embodiments, the immediate release drug layer coating includes therapeutically effective doses of two or more pharmaceutically active ingredients or pharmaceutically effective salts thereof. In certain embodiments, the multilayered tablet core comprises a push layer and a pull layer. In certain embodiments, the pull layer comprises a placebo layer and an active layer. In certain embodiments, the active layer comprises a drug for delayed extended release. In certain embodiments, the drug in the immediate release drug layer coating and the drug in the active layer are different. In certain embodiments, the delayed extended release is a delayed chrono release comprising a delayed immediate release and a delayed extended release. In certain embodiments, the placebo layer is in fluid communication with the orifice.

In certain embodiments, the disclosure provides programmable osmotic-controlled oral compositions providing pulsatile release of a drug. In certain embodiments, the programmable osmotic-controlled oral compositions of the disclosure comprise a multilayered tablet core comprising layers in the following order: a placebo layer in fluid communication with the orifice in the semipermeable membrane, an active layer, a (second) placebo layer, an (second) active layer, and a push layer, wherein the push layer is away (e.g., furthest away) from the orifice in the semipermeable membrane. In certain embodiments, the pulsatile release comprises pulses of drug release separated by a well-defined lag time(s). In certain embodiments, the pulsatile release is a delayed pulsatile release.

In certain embodiments, the programmable osmotic-controlled oral compositions of the disclosure are programmed to obtain a desired lag time by adjusting the composition of the placebo layer and/or the push layer, e.g., the amount and/or molecular weight/grade of the polyethylene oxide polymer (e.g., POLYOX®) in the placebo layer and/or the push layer, the coating composition of the semipermeable membrane, and/or the coating level of the semipermeable membrane.

In certain embodiments, the amount and/or molecular weight of the POLYOX® in the placebo layer can affect lag time. In certain embodiments, the placebo layer provides a desired lag time by delaying the release of the active pharmaceutical ingredient/drug in the environment of use. In certain embodiments, the lag time depends upon the amount/volume of the placebo layer that must be displaced by the expanding push layer. In certain embodiments, the lag time depends upon the molecular weight/grade of the POLYOX® (e.g., POLYOX® grade) present in the placebo layer. In certain embodiments, the lag time increases with increasing the molecular weight/grade of the POLYOX® present in the placebo layer. In certain embodiments, the volume of the placebo layer depends upon the amount of POLYOX® present in the placebo layer. In certain embodiments, the lag time increases as the amount of POLYOX® in the placebo layer increases. FIG. 23 demonstrates that compositions with placebo layers containing POLYOX®, with an average molecular weight of at least about 300K, provide a lag time of at least about 6 hours. FIG. 14 compares lag times of compositions of the disclosure containing POLYOX® 1105 (MW of 900K) and POLYOX® 205 (MW of 600K) in the placebo layer. The Figure demonstrates that compositions containing POLYOX® 1105 in the placebo layer exhibit a longer lag time compared to compositions containing POLYOX® 205. In certain embodiments, compositions containing POLYOX® 1105 in the placebo layer do not exhibit a change in lag time with increasing the amount of POLYOX® in the placebo layer. FIG. 7 shows that the programmable osmotic-controlled oral compositions of the disclosure, containing POLYOX® 1105 in the placebo layer, and having a drug to polymer weight ratio of about 28:72, do not show any change in lag time with change in the amount of the POLYOX® in the placebo layer. FIG. 8 shows that the programmable osmotic-controlled compositions of the disclosure do not show any change in lag time with POLYOX® 1105 or POLYOX® 205.

In certain embodiments, the amount and/or molecular weight of the POLYOX® in the push layer can affect lag time. FIG. 15 shows a decrease in lag time with an increase in amount of POLYOX® in push layer. In certain embodiments, the variation in lag time with the volume/amount of push layer is minimized when the drug layer comprises a drug to polymer weight ratio of about 40:60 and/or the placebo layer comprises POLYOX® having a molecular weight of at least about 600K, e.g., POLYOX® 205 or POLYOX® 1105. FIG. 17 shows that programmable osmotic-controlled oral compositions of the disclosure containing POLYOX® 1105 in the placebo layer, and having a drug to polymer weight ratio of about 40:60, do not show any change in lag time, with a change in the volume/amount of the push layer. In certain embodiments, the amount/volume of the push layer can be changed by changing the amount of sodium chloride and/or the POLYOX® in the push layer.

In certain embodiments, the amount of osmogen, e.g., sodium chloride, in the active layer can affect lag time. FIG. 14 demonstrates that programmable osmotic-controlled oral compositions of the disclosure containing POLYOX® 205 in the placebo layer show a decrease in lag time with an increase in the amount of sodium chloride in the active layer. In certain embodiments, the presence of sodium chloride in the active layer increases the rate of hydration of POLYOX® in the active layer and improves drug recovery without changing the lag time. FIG. 10 demonstrates that programmable osmotic-controlled oral compositions of the disclosure containing POLYOX® 1105 in the placebo layer show no change in lag time with the presence of sodium chloride in the active layer. FIG. 10 demonstrates that the presence of sodium chloride in the active layer improves drug recovery without affecting lag time.

In certain embodiments, the presence of sodium chloride in the push layer affects lag time, release rate, and/or drug recovery of the composition. In certain embodiments, the presence of sodium chloride in the push layer increases hydration and gelling of POLYOX® present in the push layer, which increases the release rate and drug recovery from the composition. FIG. 11 shows the effect of the presence of sodium chloride in the push layer on drug recovery and lag time. FIG. 11 demonstrates that programmable osmotic-controlled oral compositions of the disclosure containing POLYOX® 205 in the placebo layer and having a drug to polymer ratio of about 30:70, show a decrease in lag time with the addition of sodium chloride into the push layer. FIG. 11 further demonstrates that a lag time of at least about 6 hours is obtained with the presence of about 10% to about 18% of sodium chloride in the push layer; and the lag time remains unchanged thereafter with any further increase in sodium chloride amount in the push layer.

In certain embodiments, the drug to polymer weight ratio in the active layer affects lag time and drug recovery at 24 hours. In certain embodiments, an increase in drug to polymer weight ratio in the active layer decreases lag time while providing higher drug recovery compared to corresponding compositions with lower drug to polymer weight ratio in the active layer. In certain embodiments, a drug to polymer weight ratio of about 28:72 improves drug recovery at 24 hours, without affecting the lag time, when compared with compositions having a drug to polymer weight ratio of about 20:80. In certain embodiments, the presence of sodium chloride in the active layer improves drug recovery at 24 hours without affecting lag time. In certain embodiments, an active layer containing a drug to polymer weight ratio of 40:60 requires sodium chloride in an amount of at least about 3 wt % of the active layer to provide a lag time of at least 6 hours.

In certain embodiments, the placebo layer is substantially free of osmogen and disintegrant/wicking agent. It was surprisingly observed that the programmable osmotic-controlled oral compositions of the disclosure provide a lag time of at least 6 hours in the absence of an osmogen/water entraining agent and/or in the absence of a disintegrant/wicking agent in the placebo layer. FIG. 25 compares dissolution rate of Tablet 52 and Tablet 53. The Figure demonstrates that addition of superdisintegrant and sodium chloride in placebo layer reduces the drug recovery without affecting lag time.

In certain embodiments, the lag time and drug recovery depend upon the membrane composition and coating weight gain/coating level of the membrane. In certain embodiments, the membrane is a semipermeable membrane comprising at least one water-insoluble polymer and a pore former. In certain embodiments, the membrane comprises cellulose acetate (CA) and polyethylene glycol (PEG) with a CA to PEG ratio of between about 80:20 and about 99.5:0.5. In certain embodiments, the membrane comprises OPADRY® CA with CA to PEG ratio of about 95:5 or about 98:2. In certain embodiments, increasing the amount of cellulose acetate in the membrane reduces drug recovery and increases lag time. FIG. 12 compares drug recovery and lag time between compositions of the disclosure comprising OPADRY® CA (CA:PEG ratio of 95:5) and OPADRY® CA (98:2). FIG. 12 demonstrates that compositions containing OPADRY® CA (95:5) provide better drug recovery compared to compositions containing OPADRY® CA (98:2). In certain embodiments, the lag time increases with increasing the coating weight gain/coating level of the semipermeable membrane. In certain embodiments, drug recovery is reduced, and lag time is increased with increasing coating weight gain of the semipermeable membrane. FIG. 18 demonstrates that lag time increases and drug recovery decreases with an increase in the coating weight gain from about 12.5% to about 15%.

In certain embodiments, the compositions of the disclosure do not exhibit any change in lag time with changing hydrodynamics and viscosity of the dissolution medium. FIG. 21 compares in vitro release profiles of compositions as determined in USP Apparatus II with a paddle speed of 50 rpm in 0.01 N HCl at 37° C., and in USP Apparatus III with agitation at 25 dpm in 0.01 N HCl at 37° C., conditions simulating hydrodynamics of the GI tract. FIG. 21 demonstrates that there is no substantial change in lag time with hydrodynamics of the dissolution medium simulating GI conditions. FIG. 20 compares dissolution rates of compositions in dissolution mediums with different viscosities. FIG. 20 demonstrates that there is no change in lag time with changing viscosity of the dissolution medium simulating GI medium.

In certain embodiments, the POLYOX® grade in the push layer affects drug recovery and release profile of the composition. FIG. 24 compares the release rate and drug recovery of compositions containing POLYOX® WSR 303 (7M), POLYOX® WSR 301 (3M), and POLYOX® WSR Coagulant (5M) in the push layer. FIG. 24 demonstrates that compositions containing POLYOX® 303 in the push layer provide faster release profiles and lower drug recovery, compared to compositions containing POLYOX® WSR 301 or POLYOX® WSR Coagulant in the push layer. This can be due to reduced standard deviation in POLYOX® WSR 301 or POLYOX® WSR Coagulant compared to POLYOX® 303.

In certain embodiments, the compositions of the disclosure release no more than about 10% of the active pharmaceutical ingredient followed by extended release for about 10-16 hours, when the composition is placed in a dissolution medium comprising about 900 ml of aqueous solution of about 0.01N HCl, pH about 2.0, for up to 24 hours, as measured in USP Apparatus II, at 37° C. and agitation at 50 rpm. In certain embodiments, the compositions of the disclosure release no more than about 9%, no more than about 8%, no more than about 7%, no more than about 6%, no more than about 5%, no more than about 4%, no more than about 3%, no more than about 2%, and no more than about 1% of the active pharmaceutical ingredient followed by extended release for about 10-16 hours, when the composition is placed in a dissolution medium comprising about 900 ml of aqueous solution of about 0.01N HCl, pH about 2.0, for up to 24 hours, as measured in USP Apparatus II, at 37° C. and agitation at 50 rpm.

6.5. Methods of Treating

In certain embodiments, the programmable osmotic-controlled compositions of the disclosure delay the release of a drug and/or release drug at a rhythm that matches the human circadian rhythm of a condition's symptoms and/or of the individual being treated in the application of the therapy to optimize therapeutic outcome and minimize side effects. In certain embodiments, the programmable osmotic-controlled compositions of the disclosure can be used for treating conditions that require release of drug following circadian rhythm of the conditions, e.g., central nervous system (CNS) disorders, asthma, arthritis, congestive heart failure, myocardial infarction, stroke, cancer, peptic ulcer, narcolepsy, epilepsy, migraine, pain, etc., wherein the risks and symptoms of the disease vary predictably over time. In certain embodiments, the composition can be administered at night (e.g., before bedtime, e.g., about 8.00 pm) and the drug release is delayed for about 4 to about 10 hours or longer, followed by an extended release, pulsatile release, or a chrono drug release.

In certain embodiments, the programmable osmotic-controlled compositions of the disclosure provide delayed release of a stimulant used for the treatment of ADHD/ADD. Treatment of ADHD/ADD with stimulants helps to improve symptoms of ADHD, as well as to improve self-esteem, cognition, and social and family interactions of the patient. The most commonly prescribed medications for ADHD include mixed amphetamines and methylphenidate. These medications have calming and focusing effects on an individual suffering from ADHD. Mixed amphetamines suitable for use in the programmable osmotic-controlled compositions of the disclosure include dextroamphetamine, d,l amphetamines, and pharmaceutically acceptable salts thereof, for example a mixture of amphetamine aspartate, amphetamine sulfate, dextroamphetamine sulfate, and dextroamphetamine saccharate.

Methylphenidate is a CNS stimulant approved by the FDA in 1955 for hyperactivity. Methylphenidate can be prescribed in a racemic mixture of dextro and levo conformations or as a pure dextro isomer. The use of pharmaceutically acceptable salts of methylphenidate, such as methylphenidate hydrochloride, is also contemplated in the present disclosure.

In certain embodiments, the programmable osmotic-controlled compositions of methylphenidate comprise a multi-layered tablet core coated with a semipermeable membrane containing an orifice. In certain embodiments, the multilayered tablet core comprises a push layer, and a pull layer containing methylphenidate hydrochloride. In certain embodiments, the pull layer comprises a placebo layer, and an active layer, wherein the active layer contains methylphenidate hydrochloride. In certain embodiments, the placebo layer provides a lag time for the delay in release of methylphenidate hydrochloride. In certain embodiments, the placebo layer does not include any drug. In certain embodiments, the placebo layer can include a small amount of a drug for immediate release. In certain embodiments, drug for IR in placebo layer is not methylphenidate or a pharmaceutically acceptable salt thereof. In certain embodiments, the disclosure provides programmable osmotic-controlled compositions of methylphenidate that are administered at night, e.g., before bedtime, and deliver a therapeutic amount of methylphenidate hydrochloride in a delayed extended release pattern in order to maintain a constant release of a therapeutic amount of methylphenidate hydrochloride throughout the active periods of the day, including upon waking. In certain embodiments, the composition provides a delayed chrono release of methylphenidate hydrochloride.

In certain embodiments, the disclosure provides therapeutic compositions and methods for treatment of attention deficit disorder (ADD), attention deficit hyperactive disorder (ADHD), or other attention disorder conditions responsive to central nervous system (CNS) stimulants. In certain embodiments, the disclosure provides a method of treating attention disorders in children, comprising administering to a child in need thereof a programmable osmotic-controlled composition of the disclosure providing an immediate release of a sedative, and a delayed release of a CNS stimulant, e.g., methylphenidate. The immediate release of a therapeutic amount of sedative helps the child sleep during the night, and a delayed and extended release of a therapeutic amount of a CNS stimulant keeps the child alert throughout the active periods of the day, including when the child is waking up. In certain embodiments, the release of stimulant is delayed for at least about 6 hours followed by an extended release or a chrono release of the stimulant. In certain embodiments, the delayed release of the stimulant is delayed chrono release. In certain embodiments, the delayed chrono release is delayed immediate release and a delayed extended release of the stimulant. In certain embodiments, the sedative is clonidine, diphenhydramine, guanfacine, or melatonin. In certain embodiments, the CNS stimulant is methylphenidate hydrochloride. In certain embodiments, the composition is administered before the child goes to bed. In particular, for pediatric patients with ADHD/ADD, once daily doses of such osmotic-controlled oral compositions of the disclosure at bedtime providing an immediate release of a sedative, e.g., clonidine, guanfacine, diphenhydramine, melatonin, for promoting sedation during nighttime, followed by delayed extended release or chrono release of a CNS stimulant, e.g., methylphenidate, that starts working in the morning and lasts during the daytime, addresses problems of insomnia during night, while keeping the child alert and attentive during the day when the child is in school or engaged in activities. In certain embodiments, the release of methylphenidate is delayed for at least about 4 hours, at least about 5 hours, at least about 6 hours, at least about 7 hours, at least about 8 hours, at least about 9 hours, at least about 10 hours, at least about 11 hours, at least about 12 hours, or any intermediate periods. The composition provides a suitable lag time such that the sedative is effective during the sleep time of the patient, and the stimulant is effective during the day.

In certain embodiments, the disclosure provides programmable osmotic-controlled methylphenidate compositions providing improved patient compliance and convenience. The compositions provide clinical benefits of delivering methylphenidate hydrochloride in a delayed and extended manner, independent of drug chemical properties, patient physiological factors, and food. In certain embodiments, the disclosed compositions provide a timed, prolonged therapeutic effect when taken once a day. The programmable osmotic-controlled methylphenidate compositions of the disclosure provide food-independent delayed release that can avoid early morning dosing of methylphenidate hydrochloride stimulant to children suffering from ADHD/ADD.

The compositions can be administered, with or without food, at night, before bedtime, e.g., about 8:00 pm (although other dosing times are contemplated), and provide delayed controlled release of a stimulant, e.g., methylphenidate. In certain embodiments, the osmotic-controlled compositions of methylphenidate avoid insomnia by limiting residual amount of methylphenidate hydrochloride in plasma to less than about 10% of the maximum concentration (Cmax) during the lag time (e.g., the daily lag time).

In certain embodiments, the disclosure provides programmable osmotic-controlled compositions for treating diseases or conditions comprising attention deficit disorder (ADD), attention deficit hyperactive disorder (ADHD), narcolepsy, excessive daytime sleepiness, adrenal insufficiency, major depressive disorder, bipolar disorder, bipolar depression, negative symptoms in schizophrenia, chronic fatigue, or a binge-eating disorder. Typically, stimulant-based medications for ADHD/ADD are dosed two hours prior to beginning an early morning routine, with an onset of treatment effect usually about two hours after administration. Such medications require twice-daily administration and cause compliance issues. The compositions of the disclosure avoid the need of early morning dosing that requires an onset time of about two hours and improve the symptoms of a condition in the early morning and throughout the day. Early morning symptom control, including getting the children ready for school, is a major challenge for parents and caregivers of children suffering from ADHD/ADD. The programmable osmotic-controlled compositions of the disclosure provide a convenient method of administration in that a single dose can be taken (typically in the evening prior to going to bed, or at whatever time of the day one retires for an extended period of sleep) and the release of drug is delayed for at least about 4 hours, e.g., about 6-12 hours.

The present disclosure provides compositions that can improve the symptoms of a condition in the early morning and throughout the day, without the need for early morning dosing that requires an onset time of about two hours. The present disclosure provides programmable osmotic-controlled oral compositions comprising methylphenidate hydrochloride or mixed amphetamines. Such compositions address the long-felt need of providing food-independent delayed release that can avoid burdensome early morning dosing of methylphenidate/mixed amphetamine stimulants to children suffering from ADHD/ADD. The compositions of the disclosure provide a desired lag time that is independent of the presence or absence of food, type of food, pH, gastric emptying, and volume of fluid in the GI tract. The compositions can be administered, with or without food, at night, before bedtime (e.g., at about 8 pm), and provide delayed controlled release of the active stimulant, e.g., methylphenidate/mixed amphetamines.

In certain embodiments, the methylphenidate/mixed amphetamine compositions of the disclosure provide an immediate release of a sedative, e.g., clonidine, diphenhydramine, guanfacine or melatonin, and a delayed controlled release of a CNS stimulant, e.g., methylphenidate or mixed amphetamine salts. In certain embodiments, the compositions of the disclosure do not include any sedative. The compositions can be administered, with or without food, at night, before bedtime and provide a delayed release of the stimulant. In certain embodiments, the compositions of the disclosure provide minimal variability in lag time in various hydrodynamic conditions and pH (both conditions and regions) of the GI tract. In certain embodiments, the timing of administration is titrated to optimize the tolerability and efficacy the next morning and throughout the day. In certain embodiments, the compositions of the disclosure avoid insomnia by limiting the residual amount of methylphenidate in plasma to less than about 10% of the maximum concentration (Cmax) during the determined/planned lag time. In certain embodiments, the compositions of the disclosure limit the residual amount of methylphenidate in plasma to less than about 9%, less than about 8%, less than about 7%, less than about 6%, less than about 5%, less than about 4%, less than about 3%, less than about 2%, and less than about 1% of the maximum concentration (Cmax).

In certain embodiments, the disclosure provides programmable osmotic-controlled compositions providing delayed pulsatile release of a drug, e.g., osmotic-controlled pulsatile release compositions. In certain embodiments, the osmotic-controlled pulsatile release compositions of the disclosure contain drugs that undergo rapid first-pass metabolism and/or require colonic drug delivery. In certain embodiments, the compositions of the disclosure provide plasma peak concentration at an optimal time, based on circadian rhythm of a condition, and reduce the number of required doses per day by saturating the first-pass metabolism.

6.6. Methods of Making

In certain embodiments, the disclosure provides methods for preparing programmable osmotic-controlled compositions providing delayed release of a drug. In certain embodiments, the delayed release of the drug is at a rhythm that matches the human circadian rhythm of a condition's symptoms and/or of the individual being treated in the application of the therapy.

Depending on the physiochemical properties, e.g., solubility, stability, particle size, and compaction properties of the drug, the osmotic-controlled compositions of the disclosure are made by wet granulation, dry granulation, or direct compression.

In certain embodiments, the multilayered programmable osmotic-controlled compositions of the disclosure are made by wet granulation, wherein the wet granules comprising drug, swellable hydrophilic polymer, and other excipients are dried, milled, blended with extragranular excipients, and compressed into multilayered tablet cores. The resulting tablet cores are coated with a semipermeable membrane coat followed by laser drilling of an orifice in the coating, and, optionally, coating of an immediate release drug layer/coat over the semipermeable membrane layer/coat. In certain embodiments, the semipermeable membrane coat includes a water-soluble pore former. In certain embodiments, the water-soluble pore former is a water-soluble plasticizer. In certain embodiments, the immediate release layer is further coated with an over coat. In certain embodiments, there is a seal coat between the semipermeable membrane and the immediate release drug layer comprising drug for immediate release.

In certain embodiments, wet granulation comprises mixing of active drug, swellable hydrophilic polymer, and other excipients into a pre-blend, addition of liquid to the pre-blend for wetting of the pre-blend and formation of granules, milling for deagglomeration of granules, and drying and screening of the resulting granules.

For water-sensitive drugs, wet granulation is performed using organic solvents including methylene chloride, ethanol, isopropyl alcohol, butyl alcohol, ethyl acetate, cyclohexane, and carbon tetrachloride. In certain embodiments, wet granulation can be low shear, high shear, or fluid bed granulation. In certain embodiments, the fluid bed granulation comprises top spray granulation or rotor granulation.

In certain embodiments, the programmable osmotic-controlled compositions of the disclosure comprising active drugs with low drug loading, good flow, and compressibility are made by dry granulation comprising roller compaction or slugging. In such embodiments, it is important to match particle size of the drug and the swellable hydrophilic polymer, e.g. POLYOX®. In certain embodiments, compositions containing water-sensitive active drugs are made by a dry granulation process.

In certain embodiments, the dry granulation process includes slugging. In certain embodiments, slugging comprises blending of active drug and excipients into a uniform blend, optional milling of the resulting blend to break down agglomerates and disperse the active drug, compacting the blend into large slugs, milling of the slugs into granules with desired particle size, and compressing the granules with extragranular excipients into tablets.

In certain embodiments, dry granulation includes roller compaction, wherein densification of dry powder comprising active drug and excipients into a compact is obtained by controlled feeding of the powder through a set of directly opposed counter rotating rollers.

In certain embodiments, the disclosure provides making a multilayered tablet core for providing delayed controlled release of a drug. The multilayered tablet core comprises a push layer and a pull layer. The pull layer comprises granules made by roller compaction or wet granulation, and the push layer comprises granules made by direct compaction/slugging. In certain embodiments, the pull layer comprises an active layer and a placebo layer.

In certain embodiments, the solvents used for coating the semipermeable membrane include a mixture of acetone and water, wherein the film porosity increases with increasing water content.

In certain embodiments, the programmable osmotic-controlled compositions of the disclosure provide delayed extended release of methylphenidate hydrochloride. Such salt forms of methylphenidate are prone to degradation and often have stability and shelf-life problems. Addition of a stabilizing agent, e.g., a pH-adjusting agent, to the composition decreases undesired degradation and improves product stability. In certain embodiments, the programmable osmotic-controlled methylphenidate compositions of the disclosure include a stabilizing agent to minimize the degradation of methylphenidate. In certain embodiments, the stabilizing agent comprises succinic acid, potassium phosphate, sodium phosphate, fumaric acid, citric acid, tartaric acid, malic acid, hydrochloric acid, aspartic acid, glutamic acid, oxalic acid, lactic acid, malonic acid, glyceric acid, ascorbic acid, and any combination thereof. In certain embodiments, methylphenidate hydrochloride is stable without the presence of a stabilizing agent.

7. EXAMPLES

The following examples illustrate the disclosure in a nonlimiting manner. Unless indicated to the contrary, the numerical parameters set forth herein can vary depending upon the desired properties sought to be obtained by the present disclosure.

Example 1

Preparation of Delayed Release Methylphenidate Tablet Compositions

The present Example provides various formulations for delayed release methylphenidate tablets as outlined in Table 1 and Table 2. Six different tablets were prepared.

TABLE 1

| Composition | Tablet 1 mg/dose | Tablet 2 mg/dose | Tablet 3 mg/dose |
|---|---|---|---|
| Placebo layer | | | |
| Polyethylene oxide (POLYOX ® N80) | NA | 75.00 | NA |
| Polyethylene oxide (POLYOX ® 750) | 75.00 | NA | 75.00 |
| Povidone (KOLLIDON ® 30 LP) | 8.00 | 8.00 | 8.00 |
| Succinic acid | 3.00 | 3.00 | 3.00 |
| Stearic acid | 0.90 | 0.90 | 0.90 |
| Butylated hydroxytoluene | 0.10 | 0.10 | 0.10 |
| Active layer 1 | | | |
| Methylphenidate HCl | 10.80 | 10.80 | NA |
| Polyethylene oxide (POLYOX ® N80) | 54.00 | 54.00 | NA |
| Povidone (KOLLIDON ® 30 LP) | 4.00 | 4.00 | NA |
| Succinic acid | 1.10 | 1.10 | NA |
| Stearic acid | 0.05 | 0.05 | NA |
| Butylated hydroxytoluene | 0.05 | 0.05 | NA |
| Active layer 2 | | | |
| Methylphenidate HCl | 43.20 | 43.20 | 54.00 |
| Polyethylene oxide (POLYOX ® N80) | 149.0 | 149.0 | 207.0 |
| Povidone (KOLLIDON ® 30 LP) | 7.00 | 7.00 | 8.00 |
| Succinic acid | 3.00 | 3.00 | 3.00 |
| Stearic acid | 0.75 | 0.75 | 0.90 |
| Butylated hydroxytoluene | 0.05 | 0.05 | 0.10 |
| Push Layer | | | |
| Polyethylene oxide (POLYOX ® 303) | 135.0 | 135.0 | 135.0 |
| Povidone (KOLLIDON ® 30 LP) | 36.50 | 36.50 | 36.50 |
| Sodium chloride | 9.15 | 9.15 | 9.15 |
| Stearic acid | 0.45 | 0.45 | 0.45 |
| Butylated hydroxytoluene | 0.10 | 0.10 | 0.10 |
| Red pigment blend | 1.80 | 1.80 | 1.80 |
| Functional Coating Layer | | | |
| Cellulose acetate | 40.70 | 40.70 | 40.70 |
| Polyethylene glycol 3350 | 0.40 | 0.40 | 0.40 |
| Acetone* | NA | NA | NA |
| Purified water* | NA | NA | NA |
| Total Weight | 583.70 | 583.70 | 583.70 |

*Removed during process

TABLE 2

| Composition | Tablet 4 mg/dose | Tablet 5 mg/dose | Tablet 6 mg/dose |
|---|---|---|---|
| Placebo layer | | | |
| Polyethylene oxide (POLYOX ® N80) | NA | 75.00 | NA |
| Polyethylene oxide (POLYOX ® 750) | 75.00 | NA | 75.00 |
| Povidone (KOLLIDON ® 30 LP) | 8.00 | 8.00 | 8.00 |
| Succinic acid | 3.00 | 3.00 | 3.00 |
| Stearic acid | 0.90 | 0.90 | 0.90 |
| Butylated hydroxytoluene | 0.10 | 0.10 | 0.10 |
| Active layer 1 | | | |
| Methylphenidate HCl | 10.80 | 10.80 | NA |
| Polyethylene oxide (POLYOX ® N80) | 37.24 | 37.24 | NA |
| Povidone (KOLLIDON ® 30 LP) | 4.00 | 4.00 | NA |
| Succinic acid | 1.10 | 1.10 | NA |
| Stearic acid | 0.05 | 0.05 | NA |
| Butylated hydroxytoluene | 0.05 | 0.05 | NA |
| Active layer 2 | | | |
| Methylphenidate HCl | 43.20 | 43.20 | 54.0 |
| Polyethylene oxide (POLYOX ® N80) | 216.0 | 216.0 | 270.0 |
| Povidone (KOLLIDON ® 30 LP) | 7.0 | 7.0 | 8.0 |
| Succinic acid | 3.0 | 3.0 | 3.0 |
| Stearic acid | 0.75 | 0.75 | 0.90 |
| Butylated hydroxytoluene | 0.05 | 0.05 | 0.10 |

TABLE 2-continued

| Composition | Tablet 4 mg/dose | Tablet 5 mg/dose | Tablet 6 mg/dose |
|---|---|---|---|
| Push Layer | | | |
| Polyethylene oxide (POLYOX ® 303) | 135.0 | 135.0 | 135.0 |
| Povidone (KOLLIDON ® 30 LP) | 36.50 | 36.50 | 36.50 |
| Sodium chloride | 9.15 | 9.15 | 9.15 |
| Stearic acid | 0.45 | 0.45 | 0.45 |
| Butylated hydroxytoluene | 0.10 | 0.10 | 0.10 |
| Red pigment blend | 1.80 | 1.80 | 1.80 |
| Functional Coating Layer | | | |
| Cellulose acetate | 40.70 | 40.70 | 40.70 |
| Polyethylene glycol 3350 | 0.40 | 0.40 | 0.40 |
| Acetone* | NA | NA | NA |
| Purified water* | NA | NA | NA |
| Total Weight | 687.58 | 687.58 | 647.1 |

*Removed during process

Tablets 1, 2, 4, and 5 contain two active layers, whereas Tablet 3 and Tablet 6 contain only one active layer. Tablets 1 and 2, and Tablets 4 and 5, differ in the grades of POLYOX® in the placebo layer. The tablets were made according to the following manufacturing procedure.

Manufacturing Procedure:

Tablets 1-6 comprise two active layers, Active layer 1 and Active layer 2, to provide chrono drug release or extended release with increasing drug concentration. Separate blends of placebo layer, Active layer 1, Active layer 2, and push layer were made as per Tablets 1-6.

1. Preparation of placebo blend: Povidone and BHT were added to dehydrated alcohol in a suitable stainless steel container and mixed to obtain a clear solution; the resulting solution was sprayed onto polyethylene oxide taken in a high shear mixer; the resulting granules were dried at about 40° C. in a forced air oven, and screened through screen #20; the resulting screened granules were taken in a V-blender containing succinic acid (prescreened through screen #30) and mixed for about 7 minutes at 25 RPM, followed by addition of stearic acid (prescreened through screen #30) and mixed for about 3 minutes at 25 RPM.
2. Preparation of active layer 1 and active layer 2 blend: Povidone and BHT were added to dehydrated alcohol in a suitable stainless steel container and mixed to obtain a clear solution; the resulting solution was sprayed onto a blend of methylphenidate and polyethylene oxide taken in a high shear mixer; the resulting granules were dried at about 40° C. in a forced air oven, and screened through screen #20; the resulting screened granules were taken in a V-blender containing succinic acid (prescreened through screen #30) and mixed for about 7 minutes at 25 RPM, followed by addition of stearic acid (prescreened through screen #30) and mixed for about 3 minutes at 25 RPM.
3. Preparation of push layer blend: Povidone and BHT were added to dehydrated alcohol in a suitable stainless steel container and mixed to obtain a clear solution; the resulting solution was sprayed onto a blend of polyethylene oxide, sodium chloride, and red pigment blend taken in a high shear mixer; the resulting granules were dried at about 40° C. in a forced air oven, and screened through screen #20; the resulting screened granules were taken in a V-blender containing stearic acid (prescreened through screen #30) and mixed for about 3 minutes at 25 RPM.
4. Required amount of each blend (as per Tablets 1-3) was filled into the die and then compressed into tetra-layer tablet compositions.
5. Cellulose acetate was added to a stainless steel container charged with acetone and mixed to obtain a clear solution.
6. Polyethylene glycol 3350 was added to the solution from step #5, followed by the addition of water, and mixed for about 30 minutes.
7. The tablets from step #4 were taken in a coating pan and coated with the solution from step #6 until the target % weight gain is attained, and then cured at a product temperature of 40° C. for one hour.
8. A hole of about 0.3 mm is drilled into the coating at the center of the placebo end of the tablet.

Example 2

Preparation of Composition Providing IR of Clonidine and Delayed Release of Methylphenidate The present Example provides various formulations for delayed release methylphenidate tablets that comprise clonidine HCl IR coating. The components of the clonidine HCl IR coating are provided in Table 3 below.

TABLE 3

| Clonidine HCl IR coating | |
|---|---|
| Composition | Tablets 7-12 mg/dose |
| Clonidine HCl | 0.3 |
| Hypromellose (METHOCEL ™ E5 LV) | 2.5 |
| Talc | 0.5 |
| Ethanol* | NA |
| Purified water* | NA |

*Removed during process

The Clonidine HCl IR coating is added to Tablets 1-6 of the Example 1 according to the procedure detailed below.

Manufacturing Procedure:

1. Hypromellose is added to ethanol taken in a stainless steel container and mixed until it is uniformly dispersed. Purified water is slowly added and mixed until a clear solution is formed.
2. To the solution from step #1, clonidine HCl is added and mixed until dissolved.
3. Talc is added to the solution from step #2 and mixed until it is uniformly dispersed.
4. Methylphenidate HCl tablets (Tablets 1-6) are taken in a coating pan and coated with the dispersion from step #3.

Example 3

Preparation of Delayed Release Amphetamine Tablet Compositions

The present Example provides three different delayed release amphetamine tablet compositions. The components of the different tablets are outlined below in Table 4.

TABLE 4

| Composition | Tablet 13 mg/dose | Tablet 14 mg/dose | Tablet 15 mg/dose |
|---|---|---|---|
| Placebo Layer | | | |
| Polyethylene oxide (POLYOX ® N80) | NA | 6.750 | NA |
| Polyethylene oxide (POLYOX ® 750) | 6.750 | NA | 6.750 |

TABLE 4-continued

| Composition | Tablet 13 mg/dose | Tablet 14 mg/dose | Tablet 15 mg/dose |
|---|---|---|---|
| Povidone (KOLLIDON ® 30 LP) | 0.720 | 0.720 | 0.720 |
| Succinic acid | 0.270 | 0.270 | 0.270 |
| Stearic acid | 0.081 | 0.081 | 0.081 |
| Butylated hydroxytoluene | 0.009 | 0.009 | 0.009 |
| Active Layer 1 | | | |
| Mixed amphetamine salts (base equivalence) | 1.000 | 1.000 | NA |
| Polyethylene oxide (POLYOX ® N80) | 3.35 | 3.35 | NA |
| Povidone (KOLLIDON ® 30 LP) | 0.360 | 0.360 | NA |
| Succinic acid | 0.099 | 0.099 | NA |
| Stearic acid | 0.004 | 0.004 | NA |
| Butylated hydroxytoluene | 0.0045 | 0.0045 | NA |
| Active Layer 2 | | | |
| Mixed amphetamine salts (base equivalence) | 4.000 | 4.000 | 5.000 |
| Polyethylene oxide (POLYOX ® N80) | 19.44 | 19.44 | 24.3 |
| Povidone (KOLLIDON ® 30 LP) | 0.630 | 0.630 | 0.720 |
| Succinic acid | 0.270 | 0.270 | 0.270 |
| Stearic acid | 0.0675 | 0.0675 | 0.081 |
| Butylated hydroxytoluene | 0.0045 | 0.0045 | 0.009 |
| Push Layer | | | |
| Polyethylene oxide (POLYOX ® 303) | 12.150 | 12.150 | 12.150 |
| Povidone (KOLLIDON ® 30 LP) | 3.285 | 3.285 | 3.285 |
| Sodium chloride | 0.823 | 0.823 | 0.823 |
| Stearic acid | 0.45 | 0.45 | 0.45 |
| Butylated hydroxytoluene | 0.0405 | 0.0405 | 0.0405 |
| Red pigment blend | 0.162 | 0.162 | 0.162 |
| Functional Coating Layer | | | |
| Cellulose acetate | 3.663 | 3.663 | 3.663 |
| Polyethylene glycol 3350 | 0.036 | 0.036 | 0.036 |
| Acetone* | NA | NA | NA |
| Purified water* | NA | NA | NA |
| Total Weight | 53.149 | 53.149 | 53.149 |

*Removed during process

Tablet 13 and Tablet 14 differ in the grades of POLYOX® in the placebo layer. Both Tablet 13 and Tablet 14 include two active layers, whereas Tablet 15 includes one active layer. The tablets are made according to the following manufacturing procedure.

Manufacturing Procedure:

Separate blends of placebo layer, active layer 1, active layer 2, and push layer are made as per Tablets 13-15.

1. Preparation of placebo blend: Povidone and BHT are added to dehydrated alcohol in a suitable stainless steel container and mixed to obtain a clear solution; the resulting solution is sprayed onto polyethylene oxide taken in a high shear mixer; the resulting granules are dried at about 40° C. in a forced air oven, and screened through screen #20; the resulting screened granules were taken in a V-blender containing succinic acid (prescreened through screen #30) and mixed for about 7 minutes at 25 RPM, followed by addition of stearic acid (prescreened through screen #30) and mixed for about 3 minutes at 25 RPM.
2. Preparation of active layer 1 and active layer 2 blend: Povidone and BHT are added to dehydrated alcohol in a suitable stainless steel container and mixed to obtain a clear solution; the resulting solution is sprayed onto a blend of mixed amphetamine base, and polyethylene oxide taken in a high shear mixer; the resulting granules are dried at about 40° C. in a forced air oven, and screened through screen #20; the resulting screened granules are taken in a V-blender containing succinic acid (prescreened through screen #30) and mixed for 7 minutes at 25 RPM, followed by addition of stearic acid (prescreened through screen #30) and mixed for about 3 minutes at 25 RPM.
3. Preparation of push layer blend: Povidone and BHT are added to dehydrated alcohol in a suitable stainless steel container and mixed to obtain a clear solution; the resulting solution is sprayed onto a blend of polyethylene oxide, sodium chloride, and red pigment blend taken in a high shear mixer; the resulting granules are dried at about 40° C. in a forced air oven, and screened through screen #20; the resulting screened granules are taken in a V-blender containing stearic acid (prescreened through screen #30) and mixed for about 3 minutes at 25 RPM.
4. Required amount of each blend (as per Tablets 13-15) is filled into the die and then compressed as tetra-layer tablet compositions.
5. Cellulose acetate is added to a stainless steel container charged with acetone and mixed to obtain a clear solution.
6. Polyethylene glycol 3350 is added to the solution from step #5, followed by the addition of water, and mixed for about 30 minutes.
7. The tablets from step #4 are taken in a coating pan and coated with the solution from step #6 until the target % weight gain is attained and then cured at a product temperature of about 40° C. for one hour.
8. A hole of about 0.3 mm is drilled into the coating at the center of placebo end of the tablet.

Example 4

Preparation of Pulsatile Release Methylphenidate HCl

The present Example provides a formulation for pulsatile release methylphenidate HCl tablet. The components of the tablet are outlined below in Table 5.

TABLE 5

| Composition | Tablet 16 mg/dose |
|---|---|
| Placebo Layer | |
| Polyethylene oxide (POLYOX ® N80) | 75.00 |
| Povidone (KOLLIDON ® 30 LP) | 8.00 |
| Stearic acid | 0.90 |
| Butylated hydroxytoluene | 0.10 |
| Active Layer 1 | |
| Methylphenidate HCl | 27.00 |
| Polyethylene oxide (POLYOX ® N80) | 81.00 |
| Povidone (KOLLIDON ® 30 LP) | 4.00 |
| Stearic acid | 0.05 |
| Butylated hydroxytoluene | 0.05 |
| Placebo Layer | |
| Polyethylene oxide (POLYOX ® N80) | 75.00 |
| Povidone (KOLLIDON ® 30 LP) | 8.00 |
| Stearic acid | 0.90 |
| Butylated hydroxytoluene | 0.10 |

TABLE 5-continued

| Composition | Tablet 16 mg/dose |
|---|---|
| Active Layer 2 | |
| Methylphenidate HCl | 27.00 |
| Polyethylene oxide (POLYOX ® N80) | 81.0 |
| Povidone (KOLLIDON ® 30 LP) | 4.00 |
| Stearic acid | 0.05 |
| Butylated hydroxytoluene | 0.05 |
| Push Layer | |
| Polyethylene oxide (POLYOX ® 303) | 135.0 |
| Povidone (KOLLIDON ® 30 LP) | 36.50 |
| Sodium chloride | 9.15 |
| Stearic acid | 0.45 |
| Butylated hydroxytoluene | 0.10 |
| Red pigment blend | 1.80 |
| Functional Coating Layer | |
| Cellulose acetate | 40.70 |
| Polyethylene glycol 3350 | 0.40 |
| Acetone* | NA |
| Purified water* | NA |
| Total Weight | 616.30 |

*Removed during Process

Tablet 16 contains two placebo layers and two active layers disposed alternately. The composition further includes a push layer and a functional coating layer. Tablet 16 is made according to the procedure detailed below.

Manufacturing Procedure:

Separate blends of placebo layer, active layer 1, active layer 2, and push layer are made as per Tablet 16.
1. Preparation of placebo blend: Povidone and BHT are added to dehydrated alcohol in a suitable stainless steel container and mixed to obtain a clear solution; the resulting solution is sprayed onto polyethylene oxide taken in a high shear mixer; the resulting granules are dried at about 40° C. in a forced air oven, and screened through screen #20; the resulting screened granules are taken in a V-blender containing stearic acid (prescreened through screen #30) and mixed for about 3 minutes at 25 RPM.
2. Preparation of active layer 1 and active layer 2 blend: Povidone and BHT are added to dehydrated alcohol in a suitable stainless steel container and mixed to obtain a clear solution; the resulting solution is sprayed onto a blend of methylphenidate, and polyethylene oxide taken in a high shear mixer; the resulting granules are dried at about 40° C. in a forced air oven, and screened through screen #20; the resulting screened granules are taken in a V-blender containing stearic acid (prescreened through screen #30) and mixed for about 3 minutes at 25 RPM.
3. Preparation of push layer blend: Povidone and BHT are added to dehydrated alcohol in a suitable stainless steel container and mixed to obtain a clear solution; the resulting solution is sprayed onto a blend of polyethylene oxide, sodium chloride, and red pigment blend taken in a high shear mixer; the resulting granules are dried at about 40° C. in a forced air oven, and screened through screen #20; the resulting screened granules are taken in a V-blender containing stearic acid (prescreened through screen #30) and mixed for about 3 minutes at 25 RPM.
4. Required amount of each blend (as per Tablet 16) is filled into the die and then compressed into penta-layer tablet compositions.
5. Cellulose acetate is added to a stainless steel container charged with acetone and mixed to obtain a clear solution.
6. Polyethylene glycol 3350 is added to the solution from step #5, followed by the addition of water, and mixed for about 30 minutes.
7. The tablets from step #4 are taken in a coating pan and coated with the solution from step #6 until the target % weight gain is attained and then cured at a product temperature of about 40° C. for one hour.
8. A hole of about 0.3 mm is drilled into the coating at the center of placebo end of the tablet.

Clonidine HCl IR Coating

The present Example provides a formulation for pulsatile release methylphenidate HCl tablet that comprises clonidine HCl IR coating. The components of the clonidine HCl IR coating are provided in Table 6 below.

TABLE 6

| Composition | Tablet 17 mg/dose |
|---|---|
| Clonidine Hydrochloride | 0.3 |
| Hypromellose (METHOCEL E5LV) | 2.5 |
| Talc | 0.5 |
| Ethanol* | NA |
| Purified water* | NA |

*Removed during Process

The clonidine HCl IR coating is added to Tablet 16 of the Example 4 according to the procedure detailed below.

Manufacturing Procedure:
1. Hypromellose is added to ethanol taken in a stainless steel container and mixed until it is uniformly dispersed. Purified water is slowly added and mixed until a clear solution is formed.
2. To the solution from step #1, clonidine hydrochloride is added and mixed until dissolved.
3. Talc is added to the solution from step #2 and mixed until it is uniformly dispersed.
4. The methylphenidate HCl tablets (Tablet 16) are taken in a coating pan and coated with the dispersion from step #3.

Example 5

Preparation of Delayed Release Methylphenidate Tablet Compositions

The present Example provides two different delayed release methylphenidate tablet compositions. The components of the different tablets are outlined below in Table 7.

TABLE 7

| Composition | Tablet 18 mg/dose | Tablet 19 mg/dose |
|---|---|---|
| Placebo Layer | | |
| Polyethylene oxide (POLYOX ® WSR 1105) | 100.31 | 100.31 |
| Povidone (KOLLIDON ® 30 LP) | 5.22 | 5.22 |
| Stearic acid | 1.00 | 1.00 |
| Butylated hydroxytoluene | 0.13 | 0.13 |
| Red pigment blend | 0.07 | 0.07 |
| Cab-O-Sil ® (fumed silica) | 0.27 | 0.27 |
| Dehydrated alcohol* | q.s. | q.s. |
| Active Layer | | |
| Methylphenidate HCl | 54.00 | 54.00 |
| Polyethylene oxide (POLYOX ® N80) | 81.00 | 81.00 |

TABLE 7-continued

| Composition | Tablet 18 mg/dose | Tablet 19 mg/dose |
|---|---|---|
| Sodium chloride | 10.00 | 10.00 |
| Povidone (KOLLIDON ® 30 LP) | 7.60 | 7.60 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 88.00 | 88.00 |
| Sodium chloride | 22.00 | 22.00 |
| Povidone (KOLLIDON ® 30 LP) | 11.50 | 11.50 |
| Stearic acid | 0.50 | 0.50 |
| Butylated hydroxytoluene (BHT) | 0.20 | 0.20 |
| Red pigment blend | 1.50 | 1.50 |
| Cab-O-Sil ® | 0.30 | 0.30 |
| Dehydrated alcohol* | q.s. | q.s. |
| Total Core Weight | 385.00 | 385.00 |
| Functional Coating Layer | | |
| OPADRY ® CA clear (95:5) | 48.13 | 57.75 |
| Total Tablet Weight | 433.13 | 442.75 |

*Removed during process

Tablet 18 and Tablet 19 include different amounts of OPADRY® CA with CA:PEG ratio of about 95:5. The tablets were made according to the following manufacturing procedure.

Manufacturing Procedure

Separate blends of placebo layer, drug layer, and push layer were made as per Tablets 18 and 19.

1. Preparation of placebo blend: Povidone and BHT were added to dehydrated alcohol in a suitable stainless steel container and mixed to obtain a clear solution; the resulting solution was sprayed on to a blend of polyethylene oxide and red pigment blend taken in a high shear mixer; the resulting granules were dried at about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and mixed for about 3 minutes.
2. Preparation of active layer blend: Povidone and BHT were added to dehydrated alcohol in a suitable stainless steel container and mixed to obtain a clear solution; the resulting solution was sprayed on to a blend of methylphenidate, polyethylene oxide and sodium chloride taken in a high shear mixer; the resulting granules were dried at about 40° C. in a forced air oven, and screened through screen #20; the resulting screened granules are taken in a V-blender containing stearic acid (prescreened through screen #30) and mixed for about 3 minutes at 25 RPM.
3. Preparation of push layer blend: Povidone and BHT were added to dehydrated alcohol in a suitable stainless steel container and mixed to obtain a clear solution; the resulting solution was sprayed on to a blend of polyethylene oxide, sodium chloride, and red pigment blend taken in a high shear mixer; the resulting granules were dried at about 40° C. in a forced air oven, and screened through screen #20; the resulting screened granules were taken in a V-blender containing Cab-O-Sil® (prescreened through screen #30) and mixed for about 5 minutes at 25 RPM, followed by addition of stearic acid and mixed for about 3 minutes.
4. Required amount of each blend (as per Tablets 18 and 19) was filled into the die and then compressed as tri-layer tablet composition.
5. OPADRY® CA was added to a stainless steel container charged with acetone and water (about 92:8) and mixed for not less than about 60 minutes to obtain a clear solution.
6. The tablets from step #4 were taken in a coating pan and coated with the solution from step #5 until the target % weight gain was obtained and cured at a product temperature of about 40° C. for one hour.
7. A hole of about 0.3 mm was drilled into the coating at the center of placebo end of the tablet.

Example 6

Effect of POLYOX® Amount Present in Placebo Layer on Release Rate Profile of the Composition The present Example provides two different delayed release methylphenidate tablets with various amounts of POLYOX® in the placebo layer. The components of the two tablets are outlined below in Table 8.

TABLE 8

| Composition | Tablet 20 mg/dose | Tablet 21 mg/dose |
|---|---|---|
| Placebo Layer | | |
| Polyethylene oxide (POLYOX ® WSR 1105) | 150.0 | 75.0 |
| Povidone (KOLLIDON ® 30 LP) | 8.0 | 4.0 |
| Stearic acid | 1.6 | 0.8 |
| Butylated hydroxytoluene | 0.20 | 0.10 |
| Dehydrated alcohol* | q.s. | q.s. |
| Active Layer | | |
| Methylphenidate HCl | 54.0 | 54.0 |
| Polyethylene oxide (POLYOX ® N80) | 135.0 | 135.0 |
| Povidone (KOLLIDON ® 30 LP) | 4.0 | 4.0 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 88.00 | 88.00 |
| Sodium chloride | 22.00 | 22.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total Core Weight | 478.0 | 398.0 |
| Functional Coating Layer | | |
| OPADRY ® CA clear (95:5) | 71.7 | 59.7 |
| Total Weight | 549.7 | 457.7 |

*Removed during process

Trilayer methylphenidate tablets were made according to the procedure as per Example 5. Tablets 20 and 21 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 7 shows the effect of POLYOX® amount present in placebo layer on dissolution rate of the tablet. The Figure demonstrates that dissolution rate of the tablet is improved with increasing the amount of POLYOX® in the placebo layer. The Figure further demonstrates that the tablet, with placebo layer containing POLYOX® 1105, does not show any change in lag time with increasing POLYOX® amount in placebo layer.

Example 7

Effect of Average Molecular Weight of POLYOX® Present in Placebo Layer on Lag Time, Release Rate, and Drug Recovery The present Example provides two delayed release methylphenidate tablets comprising different grades of POLYOX® in the placebo layer. The components of the two tablets are outlined below in Table 9.

TABLE 9

| Composition | Tablet 22 mg/dose | Tablet 20 mg/dose |
|---|---|---|
| Placebo Layer | | |
| Polyethylene oxide (POLYOX ® 205) | 150.0 | — |
| Polyethylene oxide (POLYOX ® 1105) | — | 150.0 |
| Povidone (KOLLIDON ® 30 LP) | 8.0 | 8.0 |
| Stearic acid | 1.6 | 1.6 |
| Butylated hydroxytoluene | 0.20 | 0.10 |
| Dehydrated alcohol* | q.s. | q.s. |
| Active Layer | | |
| Methylphenidate HCl | 54.0 | 54.0 |
| Polyethylene oxide (POLYOX ® N80) | 135.0 | 135.0 |
| Povidone (KOLLIDON ® 30 LP) | 4.0 | 4.0 |
| Stearic acid | 0.90 | 0.90 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 88.00 | 88.00 |
| Sodium chloride | 22.00 | 22.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total Core Weight | 478.0 | 478.0 |
| Functional Coating Layer | | |
| OPADRY ® CA clear (95:5) | 71.7 | 71.7 |
| Total Weight | 549.7 | 549.7 |

*Removed during process

Trilayer methylphenidate tablets were made according to the procedure as per Example 5. Tablets 20 and 22 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 8 shows the effect of average molecular weight of the POLYOX®, present in the placebo layer, on dissolution rate of the tablet. The Figure demonstrates an improvement in dissolution rate and reduction in drug recovery, with no change in lag time, with increasing the average molecular weight of POLYOX®, present in the placebo layer, from about 600K (POLYOX® 205) to about 900K (POLYOX® 1105).

Example 8

Effect of Drug to Polymer Ratio in the Active Layer on Lag Time of the Dosage Form The present Example provides two delayed release methylphenidate tablets comprising active layers with varying drug to polymer ratios. The components of the two tablets are outlined below in Table 10.

TABLE 10

| Composition | Tablet 23 mg/dose | Tablet 24 mg/dose |
|---|---|---|
| Placebo Layer | | |
| Polyethylene oxide (POLYOX ® WSR 1105) | 150.0 | 150.0 |
| Povidone (KOLLIDON ® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 207.0 (20:80) | 135.0 (28:72) |
| Povidone (KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 98.00 | 98.00 |
| Sodium chloride | 12.00 | 12.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total core Weight | 550.0 | 478.0 |
| Functional Coating Layer | | |
| OPADRY ® CA clear (95:5) | 82.5 | 71.7 |
| Total Weight | 632.5 | 549.7 |

*Removed during process

Trilayer methylphenidate tablets were made according to the procedure as per Example 5. Tablets 23 and 24 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 9 shows the effect of drug to polymer ratio in the active layer on lag time of the tablet. The Figure demonstrates that a drug to polymer ratio of about 28:72 provides a lag time of about 9 hours and a drug to polymer ratio of 20:80 provides a lag time of about 10 hours.

Example 9

Effect of Sodium Chloride Amount in the Active Layer on Drug Recovery

The present Example provides two delayed release methylphenidate tablets. Tablet 25 contains sodium chloride in the active layer, whereas Tablet 26 does not. The components of the two tablets are outlined below in Table 11.

TABLE 11

| Composition | Tablet 25 mg/dose | Tablet 26 mg/dose |
|---|---|---|
| Placebo Layer | | |
| Polyethylene oxide (POLYOX ® WSR 1105) | 150.0 | 150.0 |
| Povidone (KOLLIDON ® 30 LP) | 8.0 | 8.0 |
| Stearic acid | 1.6 | 1.6 |

TABLE 11-continued

| Composition | Tablet 25 mg/dose | Tablet 26 mg/dose |
|---|---|---|
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 125.0 | 135.0 |
| Sodium chloride | 10.0 | — |
| Povidone (KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 98.00 | 98.00 |
| Sodium chloride | 22.00 | 22.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Total Core Weight | 478.0 | 478.0 |
| Functional Coating Layer | | |
| OPADRY ® CA clear (95:5) | 71.7 | 71.7 |
| Total Weight | 549.7 | 549.7 |

*Removed during process

Trilayer methylphenidate tablets were made according to the procedure as per Example 5. Tablets 25 and 26 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 10 compares drug recovery from tablets with and without sodium chloride in drug layer. The Figure demonstrates that presence of sodium chloride in active layer improves drug recovery by about 5%, in comparison to tablets without sodium chloride in drug layer.

Example 10

Effect of Sodium Chloride Amount in the Push Layer on Drug Recovery

The present Example provides four delayed release methylphenidate tablets comprising various amounts of sodium chloride in the push layer. The components of the two tablets are outlined below in Table 12.

TABLE 12

| Composition | Tablet 24 mg/dose | Tablet 27 mg/dose | Tablet 28 mg/dose | Tablet 29 mg/dose |
|---|---|---|---|---|
| Placebo Layer | | | | |
| Polyethylene oxide (POLYOX ® WSR 1105) | 150.0 | 150.0 | 150.0 | 150.0 |
| Povidone (KOLLIDON ® 30 LP) | 8.0 | 8.0 | 8.0 | 8.0 |
| Stearic acid | 1.6 | 1.6 | 1.6 | 1.6 |
| Butylated hydroxytoluene | 0.20 | 0.20 | 0.2 | 0.2 |
| Dehydrated alcohol* | q.s. | q.s. | q.s. | q.s. |

TABLE 12-continued

| Composition | Tablet 24 mg/dose | Tablet 27 mg/dose | Tablet 28 mg/dose | Tablet 29 mg/dose |
|---|---|---|---|---|
| Active Layer | | | | |
| Methylphenidate HCl | 54.0 | 54.0 | 54.0 | 54.0 |
| Polyethylene oxide (POLYOX ® N80) | 135.0 | 135.0 | 135.0 | 135.0 |
| Povidone (KOLLIDON ® 30 LP) | 4.0 | 4.0 | 4.0 | 4.0 |
| Stearic acid | 0.9 | 0.9 | 0.9 | 0.9 |
| Butylated hydroxytoluene | 0.10 | 0.10 | 0.10 | 0.10 |
| Dehydrated alcohol* | q.s. | q.s. | q.s. | q.s. |
| Push Layer | | | | |
| Polyethylene oxide (POLYOX ® WSR 303) | 98.00 | 80.00 | 88.0 | 110.0 |
| Sodium chloride | 12.00 | 30.00 | 22.0 | NA |
| Povidone (KOLLIDON ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.50 | 1.50 |
| Dehydrated alcohol* | q.s. | q.s. | q.s. | q.s. |
| Total Core Weight | 478.0 | 478.0 | 478.0 | 478.0 |
| Functional Coating Layer | | | | |
| OPADRY ® CA clear (95:5) | 71.7 | 71.7 | 71.7 | 71.7 |
| Total Weight | 549.7 | 549.7 | 549.7 | 549.7 |

*Removed during process

Trilayer methylphenidate tablets were made according to the procedure as per Example 5. Tablets 24, 27, 28, and 29, were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 11 shows the effect of sodium chloride in push layer on drug recovery from the tablet. The Figure demonstrates that presence of sodium chloride in push layer improves release rate and drug recovery at 24 hours. The Figure further demonstrates that increasing the amount of sodium chloride in the push layer improves release rate and drug recovery at 24 hours.

Example 11

Effect of Membrane Composition on Lag Time and Drug Recovery

The present Example provides two delayed release methylphenidate tablets. Tablet 30 contains OPADRY® CA with CA:PEG ratio of about 95:5 in the functional coating layer, while Tablet 31 contains OPADRY® CA with CA:PEG ratio of about 98:2 in the functional coating layer. The components of the two tablets are outlined below in Table 13.

TABLE 13

| Composition | Tablet 30 mg/dose | Tablet 31 mg/dose |
|---|---|---|
| Placebo Layer | | |
| Polyethylene oxide (POLYOX ® N205) | 150.0 | 150.0 |
| Povidone (KOLLIDON ® 30 LP) | 8.0 | 8.0 |
| Stearic acid | 1.6 | 1.6 |

TABLE 13-continued

| Composition | Tablet 30 mg/dose | Tablet 31 mg/dose |
| --- | --- | --- |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 135.0 | 135.0 |
| Povidone (KOLLIDON ® 30 LP) | 4.0 | 4.0 |
| Stearic acid | 0.9 | 0.9 |
| Butylated hydroxytoluene | 0.10 | 0.10 |
| Dehydrated alcohol* | q.s. | q.s. |
| Push Layer | | |
| Polyethylene oxide (POLYOX ® WSR 303) | 80.00 | 80.00 |
| Sodium chloride | 30.00 | 30.00 |
| Povidone (KOLLIDON ® 30 LP) | 12.0 | 12.0 |
| Stearic acid | 0.50 | 0.50 |
| Butylated hydroxytoluene (BHT) | 0.20 | 0.20 |
| Red pigment blend | 1.50 | 1.50 |
| Dehydrated alcohol* | q.s. | q.s. |
| Core Tablet Weight | 478.0 | 478.0 |
| Functional Coated Layer | | |
| OPADRY ® CA clear | 71.7 | 71.7 |
| CA:PEG Ratio | 95:5 | 98:2 |
| Total Weight | 549.7 | 549.7 |

*Removed during process

Trilayer methylphenidate tablets were made according to the procedure described as per Example 5. Tablets 30 and 31 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 12 shows effect of CA to PEG ratio in the membrane on lag time and drug recovery of the tablets with 15% coating weight gain of the membrane. The Figure demonstrates that increasing amount of cellulose acetate in the membrane increases lag time and reduces drug recovery from the membrane coated tablets.

Example 12

Effect of Coating Level and Presence of Sodium Chloride in Active Layer on Lag Time and Drug Recovery The present Example provides four delayed release methylphenidate tablets. Tablets 32 and 32A include sodium chloride in the active layer and Tablets 33 and 34 do not. Tablets 32 and 32A differ in the amount of OPADRY® CA clear (95:5) in the functional coating layer. Tablet 32 comprises a 15% coating weight gain of the functional coat layer and Tablet 32A comprises a 17.5% coating weight gain of the functional coat layer. The components of the four tablets are outlined below in Table 14.

TABLE 14

| Composition | Tablet 32 mg/dose | Tablet 33 mg/dose | Tablet 34 mg/dose | Tablet 32A mg/dose |
| --- | --- | --- | --- | --- |
| Placebo Layer | | | | |
| Polyethylene oxide (POLYOX ® N205) | 150.0 | 150.0 | 75.0 | 150.0 |
| Povidone (KOLLIDON ® 30 LP) | 8.0 | 8.0 | 4.0 | 8.0 |
| Stearic acid | 1.6 | 1.6 | 0.8 | 1.6 |
| Butylated hydroxytoluene | 0.20 | 0.20 | 0.1 | 0.2 |
| Dehydrated alcohol* | q.s. | q.s. | q.s. | q.s. |
| Active Layer | | | | |
| Methylphenidate HCl | 54.0 | 54.0 | 54.0 | 54.0 |
| Polyethylene oxide (POLYOX ® N80) | 125.0 | 135.0 | 135.0 | 125.0 |
| Povidone (KOLLIDON ® 30 LP) | 4.0 | 4.0 | 4.0 | 4.0 |
| Stearic acid | 0.9 | 0.9 | 0.9 | 0.9 |
| Sodium chloride | 10.0 | NA | NA | 10.0 |
| Butylated hydroxytoluene | 0.10 | 0.10 | 0.1 | 0.10 |
| Dehydrated alcohol* | q.s. | q.s. | q.s. | q.s. |
| Push Layer | | | | |
| Polyethylene oxide (POLYOX ® WSR 303) | 88.0 | 88.0 | 88.0 | 88.0 |
| Sodium chloride | 22.0 | 22.0 | 22.0 | 22.0 |
| Povidone (KOLLIDON ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.50 | 1.50 | 1.5 | 1.5 |
| Dehydrated alcohol* | q.s. | q.s. | q.s. | q.s. |
| Core Tablet Weight | 478.0 | 478.0 | 398.0 | 478.0 |
| Functional Coating Layer | | | | |
| OPADRY ® CA clear (95:5) | 71.7 | 71.7 | 59.7 | 83.65 |
| Total Weight | 549.0 | 549.0 | 457.7 | 561.65 |

*Removed during process

Trilayer methylphenidate tablets were made according to the procedure as per Example 5. Tablets 32, 32A, the 33, and 34 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 13 shows effect of coating weight gain/coating level of the semipermeable membrane on drug recovery and lag time. The Figure demonstrates that the tablet with a higher coating level (Tablet 32A) exhibits reduced drug recovery and increased lag time. The Figure further compares drug recovery between coated tablets with and without sodium chloride in active layer. The Figure demonstrates that tablets containing sodium chloride in active layer exhibit improved drug recovery. The Figure further shows that a decrease in amount of polyethylene oxide polymer in placebo layer improves drug recovery.

Example 13

Effect of Presence of Sodium Chloride in Active Layer on Lag Time and Drug Recovery The present Example provides three delayed release methylphenidate tablets comprising different amounts of sodium chloride in the active layer and/or different grades of POLYOX® in the placebo layer. The components of the three tablets are outlined below in Table 15.

TABLE 15

| Composition | Tablet 35 mg/dose | Tablet 36 mg/dose | Tablet 37 mg/dose |
|---|---|---|---|
| Placebo Layer | | | |
| Polyethylene oxide (POLYOX® N205) | 150.0 | 150.0 | — |
| Polyethylene oxide (POLYOX® 1105) | — | — | 150.0 |
| Povidone (KOLLIDON® 30 LP) | 8.0 | 8.0 | 8.0 |
| Stearic acid | 1.6 | 1.6 | 1.6 |
| Butylated hydroxytoluene | 0.20 | 0.20 | 0.2 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX® N80) | 187.0 | 197.0 | 125.0 |
| Povidone (KOLLIDON® 30 LP) | 4.0 | 4.0 | 4.0 |
| Stearic acid | 0.9 | 0.9 | 0.9 |
| Sodium chloride | 20.0 | 10.0 | 10.0 |
| Butylated hydroxytoluene | 0.10 | 0.10 | 0.1 |
| Dehydrated alcohol* | q.s. | q.s. | q.s. |
| Push Layer | | | |
| Polyethylene oxide (POLYOX® WSR 303) | 88.0 | 88.0 | 88.0 |
| Sodium chloride | 22.0 | 22.0 | 22.0 |
| Povidone (KOLLIDON® 30 LP) | 12.0 | 12.0 | 12.0 |
| Stearic acid | 0.50 | 0.50 | 0.5 |
| Butylated hydroxytoluene (BHT) | 0.20 | 0.20 | 0.2 |
| Red pigment blend | 1.50 | 1.50 | 1.5 |
| Dehydrated alcohol* | q.s. | q.s. | q.s. |
| Core Tablet Weight | 550.0 | 550.0 | 478.0 |
| Functional Coating Layer | | | |
| OPADRY® CA clear (95:5) | 82.5 | 96.3 | 83.7 |
| Total Weight | 632.5 | 646.3 | 561.7 |

*Removed during process

Trilayer methylphenidate tablets were made according to the procedure as per Example 5. Tablets 35, 36, and 37 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 14 compares drug recovery between Tablets 35 and 36 containing different amounts of sodium chloride in the active layer. Tablet 35, containing about 20 mg of sodium chloride in the active layer, provides reduced lag time and higher drug recovery compared to tablet 36, containing about 10 mg of sodium chloride, in the active layer. The Figure demonstrates that presence of sodium chloride in active layer improves drug recovery. The Figure further compares results between Tablets 35 and 37 containing POLYOX® 205 in the placebo layer and about 20 mg of sodium chloride in the active layer; and POLYOX® 1105 in the placebo layer and about 10 mg of sodium chloride in the active layer respectively. Tablet 35 containing POLYOX® 205 and about 20 mg of sodium chloride provides reduced lag time and higher drug recovery compared to Tablet 37 containing POLYOXO® 1105 and about 10 mg of sodium chloride.

Example 14

Effect of POLYOX® Amount in Push Layer on Lag Time

The present Example provides two delayed release methylphenidate tablets comprising different amounts of POLYOX® in the push layer. The components of the two tablets are outlined below in Table 16.

TABLE 16

| Composition | Tablet 38 mg/dose | Tablet 39 mg/dose |
|---|---|---|
| Placebo Layer | | |
| Polyethylene oxide (POLYOX® N205) | 150.0 | 150.0 |
| Povidone (KOLLIDON® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX® N80) | 187.0 | 187.0 |
| Povidone (KOLLIDON® 30 LP) | 4.0 | 4.0 |
| Stearic acid | 0.9 | 0.9 |
| Butylated hydroxytoluene | 0.10 | 0.10 |
| Sodium chloride | 20.0 | 20.0 |
| Dehydrated alcohol* | q.s. | q.s. |
| Push Layer | | |
| Polyethylene oxide (POLYOX® WSR 303) | 80.00 | 62.00 |
| Sodium chloride | 22.00 | 15.5 |
| Povidone (KOLLIDON® 30 LP) | 12.0 | 8.4 |
| Stearic acid | 0.50 | 0.40 |
| Butylated hydroxytoluene (BHT) | 0.20 | 0.10 |
| Red pigment blend | 1.50 | 1.10 |
| Dehydrated alcohol* | q.s. | q.s. |
| Core Tablet Weight | 550.0 | 514.0 |
| Functional Coating Layer | | |
| OPADRY® CA clear (95:5) | 82.50 | 77.1 |
| Total Weight | 632.5 | 591.1 |

*Removed during process

Trilayer methylphenidate tablets were made according to the procedure described per Example 5. Tablets 38 and 39 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 15 shows effect of POLYOX® amount in push layer on lag time in a composition with a drug:polymer weight ratio in the active layer of about 20:80. The Figure demonstrates that the lag time decreases with increasing the amount of POLYOX® in push layer.

Example 15

Effect of pH on Lag Time

The present Example provides a delayed release methylphenidate tablet comprising a placebo layer, a single active layer, a push layer, and a functional coating layer. The components of the tablet are outlined below in Table 17.

TABLE 17

| Composition | Tablet 40 mg/dose |
|---|---|
| Placebo layer | |
| Polyethylene oxide (POLYOX® N205) | 150.0 |
| Povidone (KOLLIDON® 30 LP) | 8.0 |
| Stearic acid | 1.6 |
| Butylated hydroxytoluene | 0.20 |
| Dehydrated alcohol* | q.s. |

TABLE 17-continued

| Composition | Tablet 40 mg/dose |
|---|---|
| Active layer | |
| Methylphenidate HCl | 54.0 |
| Polyethylene oxide (POLYOX ® N80) | 125.0 |
| Povidone (KOLLIDON ® 30 LP) | 4.0 |
| Stearic acid | 0.9 |
| Butylated hydroxytoluene | 0.10 |
| Sodium chloride | 10.0 |
| Dehydrated alcohol* | q.s. |
| Push layer | |
| Polyethylene oxide (POLYOX ® WSR 303) | 88.0 |
| Sodium chloride | 22.00 |
| Povidone (KOLLIDON ® 30 LP) | 12.0 |
| Stearic acid | 0.50 |
| Butylated hydroxytoluene (BHT) | 0.10 |
| Red pigment blend | 1.60 |
| Dehydrated alcohol* | q.s. |
| Core Tablet Weight | 478.0 |
| Functional Coating Layer | |
| OPADRY ® CA clear (95:5) | 71.7 |
| Total Weight | 549.7 |

*Removed during process

Trilayer methylphenidate tablets were made according to the procedure as per Example 5. Tablet 40 was tested for dissolution in about 900 ml of about 0.01N HCl, pH 4.5 acetate buffer, and pH 6.8 phosphate buffer, for up to 24 hours, using USP Apparatus II (Sinkers), with agitation at 50 rpm and 37° C. Percentage dissolution of the tablet was measured at 2, 4, 6, 8, 10, 12, 14, 16, 18, 20, 22, and 24 hours. FIG. 16 shows effect of pH on lag time in a tablet with a drug to polymer ratio of about 30:70. The Figure demonstrates that the lag time does not change under different pH conditions.

Example 16

Effect of Push Layer Amount on Lag Time

The present Example provides two delayed release methylphenidate tablets with different amounts of components in the push layer and the functional coating layer. The components of the two tablets are outlined below in Table 18.

TABLE 18

| Composition | Tablet 41 mg/dose | Tablet 42 mg/dose |
|---|---|---|
| Placebo Layer | | |
| Polyethylene oxide (POLYOX ® 1105) | 150.0 | 150.0 |
| Povidone (KOLLIDON ® 30 LP) | 8.0 | 8.0 |
| Stearic acid | 1.6 | 1.6 |
| Butylated hydroxytoluene | 0.20 | 0.20 |
| Dehydrated alcohol* | q.s. | q.s. |
| Active Layer | | |
| Methylphenidate HCl | 54.0 | 54.0 |
| Polyethylene oxide (POLYOX ® N80) | 81.0 | 81.0 |
| Povidone (KOLLIDON ® 30 LP) | 4.0 | 4.0 |
| Stearic acid | 0.9 | 0.9 |
| Butylated hydroxytoluene | 0.10 | 0.10 |
| Sodium chloride | 10.0 | 10.0 |
| Dehydrated alcohol* | q.s. | q.s. |

TABLE 18-continued

| Composition | Tablet 41 mg/dose | Tablet 42 mg/dose |
|---|---|---|
| Push Layer | | |
| Polyethylene oxide (POLYOX ® WSR 303) | 71.00 | 88.00 |
| Sodium chloride | 17.7 | 22.0 |
| Povidone (KOLLIDON ® 30 LP) | 12.0 | 8.4 |
| Stearic acid | 0.40 | 0.50 |
| Butylated hydroxytoluene (BHT) | 0.10 | 0.10 |
| Red pigment blend | 1.3 | 1.6 |
| Dehydrated alcohol* | q.s. | q.s. |
| Core Tablet Weight | 550.0 | 514.0 |
| Functional Coating Layer | | |
| OPADRY ® CA clear (95:5) | 61.5 | 65.1 |
| Total Weight | 471.5 | 499.1 |

*Removed during process

Trilayer methylphenidate tablets were made according to the procedure as per Example 5. Tablets 41 and 42 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 17 shows effect of push layer amount on lag time in tablets with drug to polymer ratio of about 40:60. The Figure demonstrates that an increase in push layer amount, from about 108.5 mg to about 120.6 mg, improves drug recovery to up to about 93%, without affecting the lag time.

Example 17

Effect of Coating Level and Polymer Amount in Placebo Layer on Lag Time

The present Example provides four delayed release methylphenidate tablets. Tablets 43 and 43A, and Tablets 44 and 44A comprise different amounts of POLYOX® 1105 in the placebo layer. Tablets 43 and 44 include 12.5% coating weight gain, whereas Tablets 43A and 44A comprise 15% coating weight gain. The components of the four tablets are outlined below in Table 19.

TABLE 19

| Composition | Tablet 43 mg/dose | Tablet 44 mg/dose | Tablet 43A mg/dose | Tablet 44A mg/dose |
|---|---|---|---|---|
| Placebo Layer | | | | |
| POLYOX ® 1105 | 150.0 | 100.0 | 150.0 | 100.0 |
| Povidone (Kollidon ® 30 LP) | 7.8 | 5.2 | 7.8 | 5.2 |
| Stearic acid | 1.5 | 1.0 | 1.5 | 1.0 |
| Butylated hydroxytoluene | 0.20 | 0.20 | 0.20 | 0.20 |
| Cab-O-Sil ® | 0.3 | 0.2 | 0.3 | 0.2 |
| Red pigment blend | 0.2 | 0.1 | 0.2 | 0.1 |
| Dehydrated alcohol* | q.s. | q.s. | q.s. | q.s. |
| Active Layer | | | | |
| Methylphenidate HCl | 54.0 | 54.0 | 54.0 | 54.0 |
| POLYOX ® N80 | 81.0 | 81.0 | 81.0 | 81.0 |
| Povidone (Kollidon ® 30 LP) | 8.0 | 8.0 | 8.0 | 8.0 |
| Stearic acid | 0.9 | 0.9 | 0.9 | 0.9 |
| Cab-O-Sil ® | 0.4 | 0.4 | 0.4 | 0.4 |
| Butylated hydroxytoluene | 0.10 | 0.10 | 0.10 | 0.10 |
| Sodium chloride | 10.0 | 10.0 | 10.0 | 10.0 |
| Dehydrated alcohol* | q.s. | q.s. | q.s. | q.s. |
| Push Layer | | | | |
| POLYOX ® WSR 303 | 88.00 | 88.00 | 88.00 | 88.00 |
| Sodium chloride | 22.0 | 22.0 | 22.0 | 22.0 |

TABLE 19-continued

| Composition | Tablet 43 mg/dose | Tablet 44 mg/dose | Tablet 43A mg/dose | Tablet 44A mg/dose |
|---|---|---|---|---|
| Povidone (Kollidon ® 30 LP) | 12.0 | 12.0 | 12.0 | 12.0 |
| Stearic acid | 0.50 | 0.50 | 0.50 | 0.50 |
| Butylated hydroxytoluene (BHT) | 0.20 | 0.20 | 0.20 | 0.20 |
| Red pigment blend | 1.5 | 1.5 | 1.5 | 1.5 |
| Cab-O-Sil ® | 0.3 | 0.3 | 0.3 | 0.3 |
| Dehydrated alcohol* | q.s. | q.s. | q.s. | q.s. |
| Core Tablet Weight | 439.0.0 | 385.3 | 439.0.0 | 385.3 |
| Functional Coating Layer | | | | |
| Opadry CA clear (95:5) | 54.87 | 48.16 | 65.85 | 57.75 |
| Total Weight | 493.87 | 433.46 | 504.80 | 443.05 |

*Removed during process

Trilayer methylphenidate tablets were made according to the procedure as per Example 5. All tablets were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 18 shows effect of polymer amount in the placebo layer and coating weight gain/coating level of the tablet, containing a drug:polymer weight ratio of about 40:60, on lag time. The Figure demonstrates that higher polymer amounts in placebo layer and higher coating level on tablet increases lag time.

Example 18

Effect of pH and Viscosity of Dissolution Medium on Lag Time

The present Example provides a delayed release methylphenidate tablet comprising a placebo layer, a single active layer, a push layer and a functional coating layer. The components of the tablet are outlined below in Table 20.

TABLE 20

| Composition | Tablet 45 mg/dose |
|---|---|
| Placebo Layer | |
| Polyethylene oxide (POLYOX ® 1105) | 100.0 |
| Povidone (KOLLIDON ® 30 LP) | 5.2 |
| Stearic acid | 1.0 |
| Butylated hydroxytoluene | 0.20 |
| Cab-O-Sil ® | 0.3 |
| Dehydrated alcohol* | q.s. |
| Active layer | |
| Methylphenidate HCl | 54.0 |
| Polyethylene oxide (POLYOX ® N80) | 81.0 |
| Povidone (KOLLIDON ® 30 LP) | 8.0 |
| Stearic acid | 0.9 |
| Cab-O-Sil ® | 0.4 |
| Butylated hydroxytoluene | 0.10 |
| Sodium chloride | 10.0 |
| Dehydrated alcohol* | q.s. |
| Push layer | |
| Polyethylene oxide (POLYOX ® WSR 303) | 88.00 |
| Sodium chloride | 22.0 |
| Povidone (KOLLIDON ® 30 LP) | 12.0 |
| Stearic acid | 0.50 |
| Butylated hydroxytoluene (BHT) | 0.20 |

TABLE 20-continued

| Composition | Tablet 45 mg/dose |
|---|---|
| Red pigment blend | 1.5 |
| Cab-O-Sil ® | 0.3 |
| Dehydrated alcohol* | q.s. |
| Core Tablet Weight | 385.3 |
| Functional Coated Layer | |
| OPADRY ® CA (95:5) | 48.16 |
| Total Weight | 433.46 |

*Removed during process

Trilayer methylphenidate tablets were made according to the procedure as per Example 5. Tablet 45 was tested for dissolution in about 900 ml of about 0.01N HCl, about 900 ml of pH 4.5 acetate buffer, and about 900 ml of pH 6.8 phosphate buffer, for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 19 compares dissolution rate of Tablet 45 at pH about 2, pH about 4.5, and pH about 6.8. The Figure demonstrates that lag time does not change with pH of the dissolution medium. FIG. 20 provides dissolution rate of Tablet 45 in dissolution mediums with different viscosities. The Figure demonstrates that there is no change in lag time with changes in viscosity of the dissolution medium.

Example 19

Effect of Discrimination Methods on Lag Time

Dissolution rates of Tablet 45 were compared using USP Apparatus II (Sinkers) with agitation at 50 rpm and temperature of 37° C., and using USP Apparatus III (Biodis) with agitation at 25 dpm and a temperature of 37° C., mimicking effect of stomach shear on dissolution rate of the composition. Tablets 45 were placed individually in about 900 ml of about 0.01N HCl for up to 24 hours, in USP Apparatus II (Sinkers) with agitation at 50 rpm and a temperature of 37° C., and in about 250 ml of about 0.01 N HCl for up to 24 hours, in USP Apparatus III (Biodis) with agitation at 25 dpm and a temperature of 37° C. Percentage dissolution of the tablets was measured at 2, 4, 6, 8, 10, 12, 14, 16, 18, 20, 22, and 24 hours using the two methods. FIG. 21 compares dissolution rate of Tablet 45, containing a drug:polymer weight ratio of about 40:60, using the above two methods. The Figure demonstrates that there is no substantial change in lag time with changing hydrodynamics of the dissolution medium.

Example 20

Effect of Sodium Chloride Amount in the Placebo Layer on Lag Time and Release Rate The present Example provides three delayed release methylphenidate tablets comprising different amounts of sodium chloride in the placebo layer. The components of the three tablets are outlined below in Table 21.

TABLE 21

| Composition | Tablet 44 mg/dose | Tablet 46 mg/dose | Tablet 47 mg/dose |
|---|---|---|---|
| Placebo Layer | | | |
| Polyethylene oxide (POLYOX ® 1105) | 100.0 | 100.0 | 100.0 |
| Povidone (KOLLIDON ® 30 LP) | 5.2 | 5.2 | 5.2 |
| Stearic acid | 1.0 | 1.0 | 1.0 |
| Sodium chloride | — | 5.33 | 10.67 |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | 88.00 | 88.00 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.7 | 390.93 | 396.27 |
| Functional Coating Layer | | | |
| OPADRY ® CA (95:5) | 48.16 | 48.83 | 49.49 |
| Total Weight | 433.86 | 439.76 | 445.76 |

*Removed during process

Trilayer methylphenidate tablets were made according to the procedure as per Example 5. Tablets 44, 46, and 47 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 22 shows effect of sodium chloride in placebo layer on lag time and release rate. The Figure demonstrates that presence of sodium chloride in placebo layer has negligible effect on lag time and release rate.

Example 21

Effect of POLYOX® Grade in Placebo Layer on Lag Time

The present Example provides three delayed release methylphenidate tablets comprising different grades of POLYOX® in the placebo layer. The components of the three tablets are outlined below in Table 22.

TABLE 22

| Composition | Tablet 44 mg/dose | Tablet 48 mg/dose | Tablet 49 mg/dose |
|---|---|---|---|
| Placebo Layer | | | |
| Polyethylene oxide (POLYOX ® 1105) | 100.0 | — | — |
| Polyethylene oxide (POLYOX ® N750) | — | 100.0 | — |
| Polyethylene oxide (POLYOX ® N80) | — | — | 100.0 |
| Povidone (KOLLIDON ® 30 LP) | 5.2 | 5.2 | 5.2 |
| Stearic acid | 1.0 | 1.0 | 1.0 |
| Sodium chloride | — | — | — |
| Butylated hydroxytoluene | 0.20 | 0.20 | 0.2 |
| Cab-O-Sil ® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX ® N80) | 81.0 | 81.0 | 81.0 |
| Povidone (KOLLIDON ® 30 LP) | 8.0 | 8.0 | 8.0 |
| Stearic acid | 0.9 | 0.9 | 0.9 |
| Cab-O-Sil ® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX ® WSR 303) | 88.00 | 88.00 | 88.00 |
| Sodium chloride | 22.0 | 22.0 | 22.0 |
| Povidone (KOLLIDON ® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil ® | 0.3 | 0.3 | 0.3 |
| Dehydrated alcohol* | q.s.. | q.s. | q.s. |
| Core Tablet Weight | 385.7 | 385.7 | 385.7 |
| Functional Coating Layer | | | |
| OPADRY ® CA (95:5) | 48.16 | 48.16 | 48.16 |
| Total Weight | 433.86 | 433.86 | 433.86 |

*Removed during process

Trilayer methylphenidate tablets were made according to the procedure as per Example 5. Tablets 44, 48, and 49 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 23 shows the effect of POLYOX® grade in placebo layer on lag time. The Figure compares lag time in compositions containing POLYOX® 80 (200K), POLYOX® 750 (300K), and POLYOX® 1105 (900K) in placebo layer. The Figure demonstrates that the average molecular weight of POLYOX® in the placebo layer should be at least about 300K to provide a lag time of at least about 6 hours.

Example 22

Effect of POLYOX® Grade in Push Layer on Lag Time

The present Example provides three delayed release methylphenidate tablets comprising different grades of POLYOX® in the push layer. The components of the three tablets are outlined below in Table 23.

TABLE 23

| Composition | Tablet 44 mg/dose | Tablet 50 mg/dose | Tablet 51 mg/dose |
|---|---|---|---|
| Placebo Layer | | | |
| Polyethylene oxide (POLYOX® 1105) | 100.0 | — | — |
| Polyethylene oxide (POLYOX® N750) | — | 100.0 | — |
| Polyethylene oxide (POLYOX® N80) | — | — | 100.0 |
| Povidone (KOLLIDON® 30 LP) | 5.2 | 5.2 | 5.2 |
| Stearic acid | 1.0 | 1.0 | 1.0 |
| Sodium chloride | — | — | — |
| Butylated hydroxytoluene | 0.20 | 0.20 | 0.2 |
| Cab-O-Sil® | 0.3 | 0.2 | 0.2 |
| Red pigment blend | 0.1 | 0.1 | 0.1 |
| Dehydrated alcohol* | q.s. | q.s. | q.s. |
| Active Layer | | | |
| Methylphenidate HCl | 54.0 | 54.0 | 54.0 |
| Polyethylene oxide (POLYOX® N80) | 81.0 | 81.0 | 81.0 |
| Povidone (KOLLIDON® 30 LP) | 8.0 | 8.0 | 8.0 |
| Stearic acid | 0.9 | 0.9 | 0.9 |
| Cab-O-Sil® | 0.4 | 0.4 | 0.4 |
| Butylated hydroxytoluene | 0.10 | 0.10 | 0.10 |
| Sodium chloride | 10.0 | 10.0 | 10.0 |
| Dehydrated alcohol* | q.s. | q.s. | q.s |
| Push Layer | | | |
| Polyethylene oxide (POLYOX® WSR 303) | 88.00 | — | — |
| Polyethylene oxide (POLYOX® WSR 301) | — | 88.0 | — |
| Polyethylene oxide (POLYOX® WSR Coagulant) | — | — | 88.0 |
| Sodium chloride | 22.0 | 22.0 | 22.0 |
| Povidone (KOLLIDON® 30 LP) | 12.0 | 12.0 | 12.0 |
| Stearic acid | 0.50 | 0.50 | 0.50 |
| Butylated hydroxytoluene (BHT) | 0.20 | 0.20 | 0.20 |
| Red pigment blend | 1.5 | 1.5 | 1.5 |
| Cab-O-Sil® | 0.3 | 0.3 | 0.3 |
| Dehydrated alcohol* | q.s. | q.s. | q.s. |
| Core Tablet Weight | 385.7 | 385.7 | 385.7 |
| Functional Coating Layer | | | |
| OPADRY® CA (95:5) | 48.16 | 48.16 | 48.16 |
| Total Weight | 433.86 | 433.86 | 433.86 |

*Removed during process

Trilayer methylphenidate tablets were made according to the procedure as per Example 5. Tablets 44, 50, and 51 were tested for dissolution in about 900 ml of about 0.01N HCl for up to 24 hours, using USP Apparatus II (Sinkers), with agitation at 50 rpm and 37° C. Percentage dissolution of the tablets was measured at 2, 4, 6, 8, 10, 12, 14, 16, 18, 20, 22, and 24 hours. FIG. 24 shows the effect of POLYOX® grade in the push layer on release rate and drug recovery. The Figure compares release rate and drug recovery in compositions containing POLYOX® WSR 303 (7M), POLYOX® WSR 301 (3M), and POLYOX® WSR Coagulant (5M) in push layer. The Figure demonstrates that compositions containing POLYOX® WSR 301 or POLYOX® WSR Coagulant in the push layer provide faster release profile and lower drug recovery, compared to compositions containing POLYOX® 303 in the push layer.

Example 23

Effect of Presence of Disintegrant and Sodium Chloride in Placebo Layer

The present Example provides two delayed release methylphenidate tablets with or without sodium chloride, sylloid and croscarmellose sodium in the placebo layer. The components of the three tablets are outlined below in Table 24.

TABLE 24

| Composition | Tablet 52 mg/dose | Tablet 53 mg/dose |
|---|---|---|
| Placebo Layer | | |
| Polyethylene oxide (POLYOX® 1105) | 100.0 | 100.0 |
| Povidone (KOLLIDON® 30 LP) | 5.20 | 5.20 |
| Stearic acid | 1.00 | 1.0 |
| Butylated hydroxytoluene | 0.13 | 0.13 |
| Cab-O-Sil® | 0.27 | 0.27 |
| Red Pigment blend | 0.07 | 0.07 |
| Croscarmellose sodium | 4.00 | — |
| Sylloid | 2.60 | — |
| Sodium chloride | 19.9 | — |
| Dehydrated alcohol* | q.s. | q.s. |
| Active layer | | |
| Methylphenidate HCl | 54.0 | 54.0 |
| Polyethylene oxide (POLYOX® N80) | 81.0 | 36 |
| Povidone (KOLLIDON® 30 LP) | 7.60 | 5.1 |
| Stearic acid | 0.90 | 0.55 |
| Cab-O-Sil® | 0.40 | 0.28 |
| Butylated hydroxytoluene | 0.10 | 0.07 |
| Sodium chloride | 10.0 | 6.70 |
| Dehydrated alcohol* | q.s. | q.s. |
| Push layer | | |
| Polyethylene oxide (POLYOX® WSR Coagulant) | 88.00 | 88.0 |
| Sodium chloride | 22.0 | 22.0 |
| Povidone (KOLLIDON® 30 LP) | 12.0 | 12.0 |
| Stearic acid | 0.50 | 0.50 |
| Butylated hydroxytoluene (BHT) | 0.20 | 0.20 |
| Red pigment blend | 1.5 | 1.5 |
| Cab-O-Sil® | 0.3 | 0.30 |
| Dehydrated alcohol* | q.s. | q.s. |
| Core Tablet Weight | 411.67 | 333.87 |
| Functional Coating | | |
| OPADRY® CA (95:5) | 51.46 | 41.73 |
| Total Weight | 463.13 | 375.60 |

*Removed during process

Trilayer methylphenidate tablets were made according to the procedure as per Example 5. Tablets 52 and 53 were tested for dissolution in about 900 ml of about 0.01N HCl, using USP Apparatus II (Sinkers), with agitation at 50 rpm and 37° C. Percentage dissolution of the tablet was measured at 2, 4, 6, 8, 10, 12, 14, 16, 18, 20, 22, and 24 hours. FIG. 25 compares dissolution rate of Tablet 52 and Tablet 53. The Figure demonstrates that addition of a superdisintegrant and sodium chloride in the placebo layer, reduces drug recovery without affecting lag time.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

What is claimed is:

1. An osmotic-controlled oral pharmaceutical composition providing delayed release of a therapeutically effective amount of a drug, the composition comprising:
   a) a multilayered core comprising a placebo layer, an active layer, and a push layer, wherein:
      (i) the placebo layer comprises at least one low molecular weight polyethylene oxide polymer having an average molecular weight of from about 600K to about 900K,
      (ii) the active layer comprises a drug, and at least one low molecular weight polyethylene oxide polymer having an average molecular weight of less than or equal to 300K,
      (iii) the push layer comprises an osmogen and at least one high molecular weight polyethylene oxide polymer having an average molecular weight of greater than or equal to 1M; and
   b) a semipermeable membrane, containing an orifice and surrounding the core,
   wherein the layers in the multilayer core are placed in the following order: the placebo layer in fluid communication with the orifice in the semipermeable membrane; the active layer; and the push layer facing away from the orifice,
   wherein the composition provides a lag time of at least 4 hours.

2. The composition of claim 1, wherein the drug is selected from the group consisting of amphetamines, methylphenidate, diltiazem, carbamazepine, metoprolol, oxprenolol, nifedipine, albuterol, phenylpropanolamine, pseudoephedrine, chlorpheniramine maleate, prazosin, doxazosin, verapamil, oxybutynin chloride, isradipine, hydromorphone, paliperidone, modafinil, armodafinil, liothyronine, oseltamivir (Tamiflu), rifamycin, and glipizide.

3. The composition of claim 1, wherein the semipermeable membrane comprises a pH-independent water-insoluble polymer and a pH-independent pore former at a polymer to pore former ratio of between about 80:20 and about 99.5:0.5.

4. The composition of claim 3, wherein the pH-independent water-insoluble polymer in the semipermeable membrane comprises polymers selected from the group consisting of cellulose acetate, cellulose acetate butyrate, and cellulose triacetate.

5. The composition of claim 3, wherein the pore former is selected from the group comprising polyethylene glycol, hydroxypropyl cellulose, polyvinyl pyrolidone, polyvinyl acetate, mannitol, and methyl cellulose, poloxamer, triethyl citrate, triacetin, hydroxypropyl methylcellulose, glycerol, and combinations thereof.

6. The composition of claim 3, wherein the semipermeable membrane further comprises at least one plasticizer selected from the group consisting of polyethylene glycols, triethyl citrate, triacetin, diethyl tartrate, and combinations thereof.

7. The composition of claim 1, wherein the polyethylene oxide polymer in the placebo layer has an average molecular weight of about 600K or about 900K, and the polyethylene oxide polymer in the active layer has an average molecular weight of about 200K.

8. The composition of claim 1, wherein the polyethylene oxide polymer in the push layer has an average molecular weight of about 1M, about 2M, about 4M, about 5M, about 7M, or intermediate values therein.

9. The composition of claim 1, wherein the osmogen in the push layer is selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, or combinations thereof.

10. The composition of claim 1, wherein the osmogen in the push layer is present in an amount of between about 5 wt % and about 30 wt % of the push layer.

11. The composition of claim 1, wherein the semipermeable membrane is applied with a coating weight gain of from about 1 wt % to about 50 wt % of the multilayered core.

12. The composition of claim 1, wherein the composition provides drug recovery of at least about 90% at about 22 hours, from the time of administration into a dissolution medium.

13. An osmotic-controlled oral pharmaceutical composition providing delayed release of a therapeutically effective amount of a drug, the composition comprising:
   a) a multilayered core comprising a placebo layer, an active layer, and a push layer, wherein:
      (i) the placebo layer comprises at least one low molecular weight polyethylene oxide polymer having an average molecular weight of from about 600K to about 900K,
      (ii) the active layer comprises a drug and at least one low molecular weight polyethylene oxide polymer having an average molecular weight of less than or equal to 300K,
      (iii) the push layer comprises an osmogen and at least one high molecular weight polyethylene oxide polymer having an average molecular weight of greater than or equal to 1M; and
   b) a semipermeable membrane, containing an orifice and surrounding the core,
   wherein the layers in the multilayer core are placed in the following order: the placebo layer in fluid communication with the orifice in the semipermeable membrane; the active layer; and the push layer facing away from the orifice,
   wherein the drug:polymer ratio in the active layer is between 10:90 and 90:10,
   wherein the composition provides a lag time of at least 4 hours.

14. The composition of claim 13, wherein the osmogen in the push layer is present in an amount of between about 5 wt % and about 30 wt % of the push layer.

15. The composition of claim 13, wherein the semipermeable membrane comprises a pH-independent water-insoluble polymer and a pH-independent pore former at a polymer to pore former ratio of between about 80:20 and about 99.5:0.5.

16. The composition of claim 13, wherein the semipermeable membrane is applied with a coating weight gain of from about 1 wt % to about 50 wt % of the multilayered core.

17. An osmotic-controlled oral pharmaceutical composition providing delayed release of a therapeutically effective amount of a drug, the composition comprising:
   a) a multilayered core comprising a placebo layer, an active layer, and a push layer, wherein:
      (i) the placebo layer comprises at least one low molecular weight polyethylene oxide polymer having an average molecular weight of from about 600K to about 900K, or intermediate values thereof, (ii) the active layer comprises a drug and at least one low molecular weight polyethylene oxide polymer having an average molecular weight of less than or equal to 300K, (iii) the push layer comprises an osmogen and at least one high molecular weight polyethylene oxide polymer having an average molecular weight of greater than or equal to 1M; and b) a semipermeable membrane, containing an orifice and surrounding the core, wherein the layers in the multilayer core are placed in the following order: the placebo layer in fluid communication with the orifice in the semipermeable membrane; the active layer; and the push layer facing away from the orifice, wherein the semipermeable membrane comprises a pH-independent water-insoluble polymer and a pH-independent pore former at a polymer to pore former ratio of between about 80:20 and about 99.5:0.5, and wherein the composition provides a lag time of at least 4 hours.

18. The composition of claim 17, wherein the semipermeable membrane is applied with a coating weight gain of from about 1 wt % to about 50 wt % of the multilayered core.

19. The composition of claim 17, wherein the osmogen in the push layer is present in an amount of between about 5 wt % and about 30 wt % of the push layer.

* * * * *